(12) United States Patent
Simons

(10) Patent No.: US 8,343,720 B2
(45) Date of Patent: Jan. 1, 2013

(54) METHODS AND PROBES FOR IDENTIFYING A NUCLEOTIDE SEQUENCE

(75) Inventor: Malcolm James Simons, Victoria (AU)

(73) Assignee: Haplomic Technologies Pty Ltd, St. Kilda West (AU)

( * ) Notice: Subject to any disclaimer, the term of this patent is extended or adjusted under 35 U.S.C. 154(b) by 195 days.

(21) Appl. No.: 12/657,336

(22) Filed: Jan. 19, 2010

(65) Prior Publication Data

US 2010/0184057 A1 Jul. 22, 2010

Related U.S. Application Data

(63) Continuation of application No. 12/001,027, filed on Dec. 7, 2007, now abandoned, which is a continuation-in-part of application No. PCT/AU2006/001740, filed on Nov. 21, 2006.

(60) Provisional application No. 60/738,019, filed on Nov. 21, 2005.

(30) Foreign Application Priority Data

Nov. 21, 2005 (AU) .................................... 60738019

(51) Int. Cl.
*C12Q 1/68* (2006.01)
*C07H 21/00* (2006.01)
*C07H 21/02* (2006.01)
*C07H 21/04* (2006.01)

(52) U.S. Cl. ....... 435/6.1; 536/22.1; 536/23.1; 536/24.3

(58) Field of Classification Search ................ 435/6, 6.1; 536/22.1, 23.1, 24.3
See application file for complete search history.

(56) References Cited

U.S. PATENT DOCUMENTS

| | | | |
|---|---|---|---|
| 6,329,140 B1 * | 12/2001 | Lockhart et al. | ............. 435/6.13 |
| 6,342,355 B1 | 1/2002 | Hacia et al. | |
| 2005/0208517 A1 * | 9/2005 | Fodor et al. | ....................... 435/6 |
| 2010/0184057 A1 * | 7/2010 | Simons | ............................. 435/6 |

FOREIGN PATENT DOCUMENTS

| | | |
|---|---|---|
| WO | 95/11995 | 5/1995 |
| WO | 98/12354 | 3/1998 |

OTHER PUBLICATIONS

Guo et al. Oligonucleotide Arrays for High-Throughput SNPs Detection in the MHC Class I Genes: HLA-B as a Model System. Genome Research 12 : 447(2001).*
Olerup et al. HLA-DR and -DQ gene polymorphism in West Africans is twice as extensive as in North European Caucasians: Evolutionary implications. PNAS 88 : 8480 (1991).*
International Search Report for PCT/AU2006/001740 of Jan. 19, 2007.

* cited by examiner

*Primary Examiner* — Ethan C Whisenant
(74) *Attorney, Agent, or Firm* — Birch, Stewart, Kolasch & Birch, LLP

(57) ABSTRACT

The present invention provides a method for identifying a set of target nucleotide sequences capable of identifying a member of a group of related nucleotide sequences, the method comprising the step of dividing the nucleotide sequence of each member of the group into a plurality of subsequences, wherein at least two of the subsequences overlap. The method is useful in generating probe sets capable of assigning alleles at HLA or KIR loci.

28 Claims, 12 Drawing Sheets

FIGURE 1A

| | |
|---|---|
| ATCGATCGATCGATCGATC | Related Sequence #1 (SEQ ID NO: 16) |
| ATCGATCGA | subsequence (1)1 (SEQ ID NO: 17) |
| TCGATCGAT | subsequence (1)2 (SEQ ID NO: 18) |
| CGATCGATC | subsequence (1)3 (SEQ ID NO: 19) |
| GATCGATCG | subsequence (1)4 (SEQ ID NO: 20) |
| ATCGATCGA | subsequence (1)5 (SEQ ID NO: 21) |
| TCGATCGAT | subsequence (1)6 (SEQ ID NO: 22) |
| CGATCGATC | subsequence (1)7 (SEQ ID NO: 23) |
| GATCGATCG | subsequence (1)8 (SEQ ID NO: 24) |
| ATCGATCGA | subsequence (1)9 (SEQ ID NO: 25) |
| TCGATCGAT | subsequence (1)10 (SEQ ID NO: 26) |
| CGATCGATC | subsequence (1)11 (SEQ ID NO: 27) |

| | |
|---|---|
| ATCGATCGATGGATCGATC | Related Sequence #2 (SEQ ID No. 28) |
| ATCGATCGA | subsequence (2)1 (SEQ ID NO: 29) |
| TCGATCGAT | subsequence (2)2 (SEQ ID NO: 30) |
| CGATCGATG | subsequence (2)3 (SEQ ID NO: 31) |
| GATCGATGG | subsequence (2)4 (SEQ ID NO: 32) |
| ATCGATGGA | subsequence (2)5 (SEQ ID NO: 33) |
| TCGATGGAT | subsequence (2)6 (SEQ ID NO: 34) |
| CGATGGATC | subsequence (2)7 (SEQ ID NO: 35) |
| GATGGATCG | subsequence (2)8 (SEQ ID NO: 36) |
| ATGGATCGA | subsequence (2)9 (SEQ ID NO: 37) |
| TGGATCGAT | subsequence (2)10 (SEQ ID NO: 38) |
| GGATCGATC | subsequence (2)11 (SEQ ID NO: 39) |

| | |
|---|---|
| ATCGATCGATCGATCCATC | Related Sequence #3 (SEQ ID NO: 40) |
| ATCGATCGA | subsequence (3)1 (SEQ ID NO: 41) |
| TCGATCGAT | subsequence (3)2 (SEQ ID NO: 42) |
| CGATCGATC | subsequence (3)3 (SEQ ID NO: 43) |
| GATCGATCG | subsequence (3)4 (SEQ ID NO: 44) |
| ATCGATCGA | subsequence (3)5 (SEQ ID NO: 45) |
| TCGATCGAT | subsequence (3)6 (SEQ ID NO: 46) |
| CGATCGATC | subsequence (3)7 (SEQ ID NO: 47) |
| GATCGATCC | subsequence (3)8 (SEQ ID NO: 48) |
| ATCGATCCA | subsequence (3)9 (SEQ ID NO: 49) |
| TCGATCCAT | subsequence (3)10 (SEQ ID NO: 50) |
| CGATCCATC | subsequence (3)11 (SEQ ID NO: 51) |

FIGURE 1B

```
ATCGATCGA    (SEQ ID NO: 52)
TCGATCGAT    (SEQ ID NO: 53)
CGATCGATC    (SEQ ID NO: 54)
GATCGATCG    (SEQ ID NO: 55)
ATCGATCGA    (SEQ ID NO: 56)
TCGATCGAT    (SEQ ID NO: 57)
CGATCGATC    (SEQ ID NO: 58)
GATCGATCG    (SEQ ID NO: 59)
ATCGATCGA    (SEQ ID NO: 60)
TCGATCGAT    (SEQ ID NO: 61)
CGATCGATC    (SEQ ID NO: 62)

ATCGATCGA    (SEQ ID NO: 63)
TCGATCGAT    (SEQ ID NO: 64)
CGATCGATG    (SEQ ID NO: 65)
GATCGATGG    (SEQ ID NO: 66)
ATCGATGGA    (SEQ ID NO: 67)
TCGATGGAT    (SEQ ID NO: 68)
CGATGGATC    (SEQ ID NO: 69)
GATGGATCG    (SEQ ID NO: 70)
ATGGATCGA    (SEQ ID NO: 71)
TGGATCGAT    (SEQ ID NO: 72)
GGATCGATC    (SEQ ID NO: 73)

ATCGATCGA    (SEQ ID NO: 74)
TCGATCGAT    (SEQ ID NO: 75)
CGATCGATC    (SEQ ID NO: 76)
GATCGATCG    (SEQ ID NO: 77)
ATCGATCGA    (SEQ ID NO: 78)
TCGATCGAT    (SEQ ID NO: 79)
CGATCGATC    (SEQ ID NO: 80)
GATCGATCC    (SEQ ID NO: 81)
ATCGATCCA    (SEQ ID NO: 82)
TCGATCCAT    (SEQ ID NO: 83)
CGATCCATC    (SEQ ID NO: 84)
```

FIGURE 1C

| | |
|---|---|
| ATCGATCGA | (SEQ ID NO: 52) |
| TCGATCGAT | (SEQ ID NO: 53) |
| CGATCGATC | (SEQ ID NO: 54) |
| GATCGATCG | (SEQ ID NO: 55) |
| CGATCGATG | (SEQ ID NO: 65) |
| GATCGATGG | (SEQ ID NO: 66) |
| ATCGATGGA | (SEQ ID NO: 67) |
| TCGATGGAT | (SEQ ID NO: 68) |
| CGATGGATC | (SEQ ID NO: 69) |
| GATGGATCG | (SEQ ID NO: 70) |
| ATGGATCGA | (SEQ ID NO: 71) |
| TGGATCGAT | (SEQ ID NO: 72) |
| GGATCGATC | (SEQ ID NO: 73) |
| GATCGATCC | (SEQ ID NO: 81) |
| ATCGATCCA | (SEQ ID NO: 82) |
| TCGATCCAT | (SEQ ID NO: 83) |
| CGATCCATC | (SEQ ID NO: 84) |

FIGURE 2

Exon 2

| | | |
|---|---|---|
| CGAGGGTGAGGTACTCCATAAAGAA | (SEQ ID NO: | 85) |
| GAGGGTGAGGTACTCCATAAAGAAG | (SEQ ID NO: | 86) |
| AGGGTGAGGTACTCCATAAAGAAGT | (SEQ ID NO: | 87) |
| GGGTGAGGTACTCCATAAAGAAGTG | (SEQ ID NO: | 88) |
| GGTGAGGTACTCCATAAAGAAGTGT | (SEQ ID NO: | 89) |
| GTGAGGTACTCCATAAAGAAGTGTA | (SEQ ID NO: | 90) |
| TGAGGTACTCCATAAAGAAGTGTAG | (SEQ ID NO: | 91) |
| GAGGTACTCCATAAAGAAGTGTAGG | (SEQ ID NO: | 92) |
| AGGTACTCCATAAAGAAGTGTAGGC | (SEQ ID NO: | 93) |
| GGTACTCCATAAAGAAGTGTAGGCA | (SEQ ID NO: | 94) |
| GTACTCCATAAAGAAGTGTAGGCAC | (SEQ ID NO: | 95) |
| TACTCCATAAAGAAGTGTAGGCACA | (SEQ ID NO: | 96) |
| ACTCCATAAAGAAGTGTAGGCACAG | (SEQ ID NO: | 97) |
| CTCCATAAAGAAGTGTAGGCACAGG | (SEQ ID NO: | 98) |
| TCCATAAAGAAGTGTAGGCACAGGG | (SEQ ID NO: | 99) |
| CCATAAAGAAGTGTAGGCACAGGGC | (SEQ ID NO: | 100) |
| CATAAAGAAGTGTAGGCACAGGGCC | (SEQ ID NO: | 101) |
| ATAAAGAAGTGTAGGCACAGGGCCG | (SEQ ID NO: | 102) |
| TAAAGAAGTGTAGGCACAGGGCCGG | (SEQ ID NO: | 103) |
| AAAGAAGTGTAGGCACAGGGCCGGG | (SEQ ID NO: | 104) |
| AAGAAGTGTAGGCACAGGGCCGGGC | (SEQ ID NO: | 105) |
| AGAAGTGTAGGCACAGGGCCGGGCC | (SEQ ID NO: | 106) |
| GAAGTGTAGGCACAGGGCCGGGCCG | (SEQ ID NO: | 107) |
| AAGTGTAGGCACAGGGCCGGGCCGG | (SEQ ID NO: | 108) |
| AGTGTAGGCACAGGGCCGGGCCGGC | (SEQ ID NO: | 109) |
| GTGTAGGCACAGGGCCGGGCCGGCG | (SEQ ID NO: | 110) |
| TGTAGGCACAGGGCCGGGCCGGCGC | (SEQ ID NO: | 111) |
| GTAGGCACAGGGCCGGGCCGGCGCC | (SEQ ID NO: | 112) |
| TAGGCACAGGGCCGGGCCGGCGCCC | (SEQ ID NO: | 113) |
| AGGCACAGGGCCGGGCCGGCGCCCC | (SEQ ID NO: | 114) |
| GGCACAGGGCCGGGCCGGCGCCCCT | (SEQ ID NO: | 115) |
| GCACAGGGCCGGGCCGGCGCCCCTC | (SEQ ID NO: | 116) |
| CACAGGGCCGGGCCGGCGCCCCTCG | (SEQ ID NO: | 117) |
| ACAGGGCCGGGCCGGCGCCCCTCGG | (SEQ ID NO: | 118) |
| CAGGGCCGGGCCGGCGCCCCTCGGG | (SEQ ID NO: | 119) |
| AGGGCCGGGCCGGCGCCCCTCGGGG | (SEQ ID NO: | 120) |
| GGGCCGGGCCGGCGCCCCTCGGGGC | (SEQ ID NO: | 121) |
| GGCCGGGCCGGCGCCCCTCGGGGCG | (SEQ ID NO: | 122) |
| GCCGGGCCGGCGCCCCTCGGGGCGA | (SEQ ID NO: | 123) |
| CCGGGCCGGCGCCCCTCGGGGCGAA | (SEQ ID NO: | 124) |
| CGGGCCGGCGCCCCTCGGGGCGAAG | (SEQ ID NO: | 125) |
| GGGCCGGCGCCCCTCGGGGCGAAGT | (SEQ ID NO: | 126) |
| GGCCGGCGCCCCTCGGGGCGAAGTA | (SEQ ID NO: | 127) |
| GCCGGCGCCCCTCGGGGCGAAGTAG | (SEQ ID NO: | 128) |
| CCGGCGCCCCTCGGGGCGAAGTAGC | (SEQ ID NO: | 129) |
| CGGCGCCCCTCGGGGCGAAGTAGCG | (SEQ ID NO: | 130) |
| GGCGCCCCTCGGGGCGAAGTAGCGG | (SEQ ID NO: | 131) |
| GCGCCCCTCGGGGCGAAGTAGCGGC | (SEQ ID NO: | 132) |
| CGCCCCTCGGGGCGAAGTAGCGGCA | (SEQ ID NO: | 133) |
| GCCCCTCGGGGCGAAGTAGCGGCAC | (SEQ ID NO: | 134) |
| CCCCTCGGGGCGAAGTAGCGGCACC | (SEQ ID NO: | 135) |
| CCCTCGGGGCGAAGTAGCGGCACCC | (SEQ ID NO: | 136) |

FIGURE 2 (continued)

| Sequence | SEQ ID NO |
|---|---|
| CCTCGGGGCGAAGTAGCGGCACCCG | 137 |
| CTCGGGGCGAAGTAGCGGCACCCGA | 138 |
| TCGGGGCGAAGTAGCGGCACCCGAT | 139 |
| CGGGGCGAAGTAGCGGCACCCGATG | 140 |
| GGGGCGAAGTAGCGGCACCCGATGC | 141 |
| GGGCGAAGTAGCGGCACCCGATGCA | 142 |
| GGCGAAGTAGCGGCACCCGATGCAC | 143 |
| GCGAAGTAGCGGCACCCGATGCACC | 144 |
| CGAAGTAGCGGCACCCGATGCACCT | 145 |
| GAAGTAGCGGCACCCGATGCACCTG | 146 |
| AAGTAGCGGCACCCGATGCACCTGC | 147 |
| AGTAGCGGCACCCGATGCACCTGCT | 148 |
| GTAGCGGCACCCGATGCACCTGCTG | 149 |
| TAGCGGCACCCGATGCACCTGCTGT | 150 |
| AGCGGCACCCGATGCACCTGCTGTG | 151 |
| GCGGCACCCGATGCACCTGCTGTGC | 152 |
| CGGCACCCGATGCACCTGCTGTGCG | 153 |
| GGCACCCGATGCACCTGCTGTGCGT | 154 |
| GCACCCGATGCACCTGCTGTGCGTC | 155 |
| CACCCGATGCACCTGCTGTGCGTCA | 156 |
| ACCCGATGCACCTGCTGTGCGTCAA | 157 |
| CCCGATGCACCTGCTGTGCGTCAAG | 158 |
| CCGATGCACCTGCTGTGCGTCAAGC | 159 |
| CGATGCACCTGCTGTGCGTCAAGCA | 160 |
| GATGCACCTGCTGTGCGTCAAGCAC | 161 |
| ATGCACCTGCTGTGCGTCAAGCACG | 162 |
| TGCACCTGCTGTGCGTCAAGCACGC | 163 |
| GCACCTGCTGTGCGTCAAGCACGCC | 164 |
| CACCTGCTGTGCGTCAAGCACGCCA | 165 |
| ACCTGCTGTGCGTCAAGCACGCCAA | 166 |
| CCTGCTGTGCGTCAAGCACGCCAAG | 167 |
| CTGCTGTGCGTCAAGCACGCCAAGC | 168 |
| TGCTGTGCGTCAAGCACGCCAAGCT | 169 |
| GCTGTGCGTCAAGCACGCCAAGCTG | 170 |
| CTGTGCGTCAAGCACGCCAAGCTGT | 171 |
| TGTGCGTCAAGCACGCCAAGCTGTC | 172 |
| GTGCGTCAAGCACGCCAAGCTGTCG | 173 |
| TGCGTCAAGCACGCCAAGCTGTCGC | 174 |
| GCGTCAAGCACGCCAAGCTGTCGCT | 175 |
| CGTCAAGCACGCCAAGCTGTCGCTG | 176 |
| GTCAAGCACGCCAAGCTGTCGCTGC | 177 |
| TCAAGCACGCCAAGCTGTCGCTGCG | 178 |
| CAAGCACGCCAAGCTGTCGCTGCGG | 179 |
| AAGCACGCCAAGCTGTCGCTGCGGC | 180 |
| AGCACGCCAAGCTGTCGCTGCGGCG | 181 |
| GCACGCCAAGCTGTCGCTGCGGCGC | 182 |
| CACGCCAAGCTGTCGCTGCGGCGCT | 183 |
| ACGCCAAGCTGTCGCTGCGGCGCTC | 184 |
| CGCCAAGCTGTCGCTGCGGCGCTCG | 185 |
| GCCAAGCTGTCGCTGCGGCGCTCGG | 186 |
| CCAAGCTGTCGCTGCGGCGCTCGGT | 187 |
| CAAGCTGTCGCTGCGGCGCTCGGTC | 188 |
| AAGCTGTCGCTGCGGCGCTCGGTCT | 189 |
| AGCTGTCGCTGCGGCGCTCGGTCTC | 190 |
| GCTGTCGCTGCGGCGCTCGGTCTCC | 191 |
| CTGTCGCTGCGGCGCTCGGTCTCCT | 192 |
| TGTCGCTGCGGCGCTCGGTCTCCTA | 193 |

FIGURE 2 (continued)

```
GTCGCTGCGGCGCTCGGTCTCCTAC  (SEQ ID NO: 194)
TCGCTGCGGCGCTCGGTCTCCTACC  (SEQ ID NO: 195)
CGCTGCGGCGCTCGGTCTCCTACCT  (SEQ ID NO: 196)
GCTGCGGCGCTCGGTCTCCTACCTC  (SEQ ID NO: 197)
CTGCGGCGCTCGGTCTCCTACCTCG  (SEQ ID NO: 198)
TGCGGCGCTCGGTCTCCTACCTCGG  (SEQ ID NO: 199)
GCGGCGCTCGGTCTCCTACCTCGGC  (SEQ ID NO: 200)
CGGCGCTCGGTCTCCTACCTCGGCG  (SEQ ID NO: 201)
GGCGCTCGGTCTCCTACCTCGGCGC  (SEQ ID NO: 202)
GCGCTCGGTCTCCTACCTCGGCGCC  (SEQ ID NO: 203)
CGCTCGGTCTCCTACCTCGGCGCCC  (SEQ ID NO: 204)
GCTCGGTCTCCTACCTCGGCGCCCG  (SEQ ID NO: 205)
CTCGGTCTCCTACCTCGGCGCCCGC  (SEQ ID NO: 206)
TCGGTCTCCTACCTCGGCGCCCGCG  (SEQ ID NO: 207)
CGGTCTCCTACCTCGGCGCCCGCGG  (SEQ ID NO: 208)
GGTCTCCTACCTCGGCGCCCGCGGC  (SEQ ID NO: 209)
GTCTCCTACCTCGGCGCCCGCGGCA  (SEQ ID NO: 210)
TCTCCTACCTCGGCGCCCGCGGCAC  (SEQ ID NO: 211)
CTCCTACCTCGGCGCCCGCGGCACC  (SEQ ID NO: 212)
TCCTACCTCGGCGCCCGCGGCACCT  (SEQ ID NO: 213)
CCTACCTCGGCGCCCGCGGCACCTA  (SEQ ID NO: 214)
CTACCTCGGCGCCCGCGGCACCTAT  (SEQ ID NO: 215)
TACCTCGGCGCCCGCGGCACCTATC  (SEQ ID NO: 216)
ACCTCGGCGCCCGCGGCACCTATCT  (SEQ ID NO: 217)
CCTCGGCGCCCGCGGCACCTATCTC  (SEQ ID NO: 218)
CTCGGCGCCCGCGGCACCTATCTCG  (SEQ ID NO: 219)
TCGGCGCCCGCGGCACCTATCTCGT  (SEQ ID NO: 220)
CGGCGCCCGCGGCACCTATCTCGTC  (SEQ ID NO: 221)
GGCGCCCGCGGCACCTATCTCGTCC  (SEQ ID NO: 222)
GCGCCCGCGGCACCTATCTCGTCCT  (SEQ ID NO: 223)
CGCCCGCGGCACCTATCTCGTCCTC  (SEQ ID NO: 224)
GCCCGCGGCACCTATCTCGTCCTCC  (SEQ ID NO: 225)
CCCGCGGCACCTATCTCGTCCTCCC  (SEQ ID NO: 226)
CCGCGGCACCTATCTCGTCCTCCCA  (SEQ ID NO: 227)
CGCGGCACCTATCTCGTCCTCCCAG  (SEQ ID NO: 228)
GCGGCACCTATCTCGTCCTCCCAGG  (SEQ ID NO: 229)
CGGCACCTATCTCGTCCTCCCAGGC  (SEQ ID NO: 230)
GGCACCTATCTCGTCCTCCCAGGCC  (SEQ ID NO: 231)
GCACCTATCTCGTCCTCCCAGGCCT  (SEQ ID NO: 232)
CACCTATCTCGTCCTCCCAGGCCTC  (SEQ ID NO: 233)
ACCTATCTCGTCCTCCCAGGCCTCA  (SEQ ID NO: 234)
CCTATCTCGTCCTCCCAGGCCTCAT  (SEQ ID NO: 235)
CTATCTCGTCCTCCCAGGCCTCATA  (SEQ ID NO: 236)
TATCTCGTCCTCCCAGGCCTCATAA  (SEQ ID NO: 237)
ATCTCGTCCTCCCAGGCCTCATAAC  (SEQ ID NO: 238)
TCTCGTCCTCCCAGGCCTCATAACC  (SEQ ID NO: 239)
CTCGTCCTCCCAGGCCTCATAACCC  (SEQ ID NO: 240)
TCGTCCTCCCAGGCCTCATAACCCT  (SEQ ID NO: 241)
CGTCCTCCCAGGCCTCATAACCCTG  (SEQ ID NO: 242)
GTCCTCCCAGGCCTCATAACCCTGC  (SEQ ID NO: 243)
TCCTCCCAGGCCTCATAACCCTGCC  (SEQ ID NO: 244)
CCTCCCAGGCCTCATAACCCTGCCC  (SEQ ID NO: 245)
CTCCCAGGCCTCATAACCCTGCCCC  (SEQ ID NO: 246)
TCCCAGGCCTCATAACCCTGCCCCT  (SEQ ID NO: 247)
CCCAGGCCTCATAACCCTGCCCCTC  (SEQ ID NO: 248)
CCAGGCCTCATAACCCTGCCCCTCT  (SEQ ID NO: 249)
CAGGCCTCATAACCCTGCCCCTCTG  (SEQ ID NO: 250)
```

FIGURE 2 (continued)

```
AGGCCTCATAACCCTGCCCCTCTGT  (SEQ ID NO: 251)
GGCCTCATAACCCTGCCCCTCTGTG  (SEQ ID NO: 252)
GCCTCATAACCCTGCCCCTCTGTGC  (SEQ ID NO: 253)
CCTCATAACCCTGCCCCTCTGTGCC  (SEQ ID NO: 254)
CTCATAACCCTGCCCCTCTGTGCCT  (SEQ ID NO: 255)
TCATAACCCTGCCCCTCTGTGCCTT  (SEQ ID NO: 256)
CATAACCCTGCCCCTCTGTGCCTTT  (SEQ ID NO: 257)
ATAACCCTGCCCCTCTGTGCCTTTC  (SEQ ID NO: 258)
TAACCCTGCCCCTCTGTGCCTTTCA  (SEQ ID NO: 259)
AACCCTGCCCCTCTGTGCCTTTCAC  (SEQ ID NO: 260)
ACCCTGCCCCTCTGTGCCTTTCACT  (SEQ ID NO: 261)
CCCTGCCCCTCTGTGCCTTTCACTT  (SEQ ID NO: 262)
CCTGCCCCTCTGTGCCTTTCACTTC  (SEQ ID NO: 263)
CTGCCCCTCTGTGCCTTTCACTTCC  (SEQ ID NO: 264)
TGCCCCTCTGTGCCTTTCACTTCCG  (SEQ ID NO: 265)
GCCCCTCTGTGCCTTTCACTTCCGG  (SEQ ID NO: 266)
CCCCTCTGTGCCTTTCACTTCCGGG  (SEQ ID NO: 267)
CCCTCTGTGCCTTTCACTTCCGGGT  (SEQ ID NO: 268)
CCTCTGTGCCTTTCACTTCCGGGTG  (SEQ ID NO: 269)
CTCTGTGCCTTTCACTTCCGGGTGA  (SEQ ID NO: 270)
TCTGTGCCTTTCACTTCCGGGTGAG  (SEQ ID NO: 271)
CTGTGCCTTTCACTTCCGGGTGAGT  (SEQ ID NO: 272)
TGTGCCTTTCACTTCCGGGTGAGTG  (SEQ ID NO: 273)
GTGCCTTTCACTTCCGGGTGAGTGT  (SEQ ID NO: 274)
TGCCTTTCACTTCCGGGTGAGTGTC  (SEQ ID NO: 275)
GCCTTTCACTTCCGGGTGAGTGTCT  (SEQ ID NO: 276)
CCTTTCACTTCCGGGTGAGTGTCTG  (SEQ ID NO: 277)
CTTTCACTTCCGGGTGAGTGTCTGA  (SEQ ID NO: 278)
TTTCACTTCCGGGTGAGTGTCTGAG  (SEQ ID NO: 279)
TTCACTTCCGGGTGAGTGTCTGAGT  (SEQ ID NO: 280)
TCACTTCCGGGTGAGTGTCTGAGTG  (SEQ ID NO: 281)
CACTTCCGGGTGAGTGTCTGAGTGG  (SEQ ID NO: 282)
ACTTCCGGGTGAGTGTCTGAGTGGC  (SEQ ID NO: 283)
CTTCCGGGTGAGTGTCTGAGTGGCT  (SEQ ID NO: 284)
TTCCGGGTGAGTGTCTGAGTGGCTC  (SEQ ID NO: 285)
TCCGGGTGAGTGTCTGAGTGGCTCA  (SEQ ID NO: 286)
CCGGGTGAGTGTCTGAGTGGCTCAC  (SEQ ID NO: 287)
CGGGTGAGTGTCTGAGTGGCTCACC  (SEQ ID NO: 288)
GGGTGAGTGTCTGAGTGGCTCACCT  (SEQ ID NO: 289)
GGTGAGTGTCTGAGTGGCTCACCTG  (SEQ ID NO: 290)
GTGAGTGTCTGAGTGGCTCACCTGG  (SEQ ID NO: 291)
TGAGTGTCTGAGTGGCTCACCTGGA  (SEQ ID NO: 292)
GAGTGTCTGAGTGGCTCACCTGGAC  (SEQ ID NO: 293)
AGTGTCTGAGTGGCTCACCTGGACC  (SEQ ID NO: 294)
GTGTCTGAGTGGCTCACCTGGACCC  (SEQ ID NO: 295)
TGTCTGAGTGGCTCACCTGGACCCC  (SEQ ID NO: 296)
GTCTGAGTGGCTCACCTGGACCCCT  (SEQ ID NO: 297)
TCTGAGTGGCTCACCTGGACCCCTG  (SEQ ID NO: 298)
CTGAGTGGCTCACCTGGACCCCTGG  (SEQ ID NO: 299)
TGAGTGGCTCACCTGGACCCCTGGG  (SEQ ID NO: 300)
GAGTGGCTCACCTGGACCCCTGGGA  (SEQ ID NO: 301)
AGTGGCTCACCTGGACCCCTGGGAC  (SEQ ID NO: 302)
GTGGCTCACCTGGACCCCTGGGACG  (SEQ ID NO: 303)
TGGCTCACCTGGACCCCTGGGACGC  (SEQ ID NO: 304)
GGCTCACCTGGACCCCTGGGACGCG  (SEQ ID NO: 305)
GCTCACCTGGACCCCTGGGACGCGC  (SEQ ID NO: 306)
CTCACCTGGACCCCTGGGACGCGCC  (SEQ ID NO: 307)
```

FIGURE 2 (continued)

```
TCACCTGGACCCCTGGGACGCGCCG   (SEQ ID NO: 308)
CACCTGGACCCCTGGGACGCGCCGA   (SEQ ID NO: 309)
ACCTGGACCCCTGGGACGCGCCGAT   (SEQ ID NO: 310)
CCTGGACCCCTGGGACGCGCCGATG   (SEQ ID NO: 311)
CTGGACCCCTGGGACGCGCCGATGA   (SEQ ID NO: 312)
TGGACCCCTGGGACGCGCCGATGAT   (SEQ ID NO: 313)
GGACCCCTGGGACGCGCCGATGATG   (SEQ ID NO: 314)
GACCCCTGGGACGCGCCGATGATGT   (SEQ ID NO: 315)
ACCCCTGGGACGCGCCGATGATGTT   (SEQ ID NO: 316)
CCCCTGGGACGCGCCGATGATGTTG   (SEQ ID NO: 317)
CCCTGGGACGCGCCGATGATGTTGG   (SEQ ID NO: 318)
CCTGGGACGCGCCGATGATGTTGGT   (SEQ ID NO: 319)
CTGGGACGCGCCGATGATGTTGGTC   (SEQ ID NO: 320)
TGGGACGCGCCGATGATGTTGGTCT   (SEQ ID NO: 321)
GGGACGCGCCGATGATGTTGGTCTC   (SEQ ID NO: 322)
GGACGCGCCGATGATGTTGGTCTCG   (SEQ ID NO: 323)
GACGCGCCGATGATGTTGGTCTCGC   (SEQ ID NO: 324)
ACGCGCCGATGATGTTGGTCTCGCT   (SEQ ID NO: 325)
CGCGCCGATGATGTTGGTCTCGCTC   (SEQ ID NO: 326)
GCGCCGATGATGTTGGTCTCGCTCC   (SEQ ID NO: 327)
CGCCGATGATGTTGGTCTCGCTCCG   (SEQ ID NO: 328)
GCCGATGATGTTGGTCTCGCTCCGG   (SEQ ID NO: 329)
CCGATGATGTTGGTCTCGCTCCGGC   (SEQ ID NO: 330)
```

Exon 3

```
CAAGAGTGTGGCAGGTCTCCTACAT   (SEQ ID NO: 331)
AAGAGTGTGGCAGGTCTCCTACATA   (SEQ ID NO: 332)
AGAGTGTGGCAGGTCTCCTACATAC   (SEQ ID NO: 333)
GAGTGTGGCAGGTCTCCTACATACC   (SEQ ID NO: 334)
AGTGTGGCAGGTCTCCTACATACCG   (SEQ ID NO: 335)
GTGTGGCAGGTCTCCTACATACCGA   (SEQ ID NO: 336)
TGTGGCAGGTCTCCTACATACCGAC   (SEQ ID NO: 337)
GTGGCAGGTCTCCTACATACCGACG   (SEQ ID NO: 338)
TGGCAGGTCTCCTACATACCGACGC   (SEQ ID NO: 339)
GGCAGGTCTCCTACATACCGACGCT   (SEQ ID NO: 340)
GCAGGTCTCCTACATACCGACGCTG   (SEQ ID NO: 341)
CAGGTCTCCTACATACCGACGCTGC   (SEQ ID NO: 342)
AGGTCTCCTACATACCGACGCTGCA   (SEQ ID NO: 343)
GGTCTCCTACATACCGACGCTGCAC   (SEQ ID NO: 344)
GTCTCCTACATACCGACGCTGCACC   (SEQ ID NO: 345)
TCTCCTACATACCGACGCTGCACCC   (SEQ ID NO: 346)
CTCCTACATACCGACGCTGCACCCC   (SEQ ID NO: 347)
TCCTACATACCGACGCTGCACCCCA   (SEQ ID NO: 348)
CCTACATACCGACGCTGCACCCCAG   (SEQ ID NO: 349)
CTACATACCGACGCTGCACCCCAGC   (SEQ ID NO: 350)
TACATACCGACGCTGCACCCCAGCC   (SEQ ID NO: 351)
ACATACCGACGCTGCACCCCAGCCT   (SEQ ID NO: 352)
CATACCGACGCTGCACCCCAGCCTG   (SEQ ID NO: 353)
ATACCGACGCTGCACCCCAGCCTGA   (SEQ ID NO: 354)
TACCGACGCTGCACCCCAGCCTGAC   (SEQ ID NO: 355)
ACCGACGCTGCACCCCAGCCTGACC   (SEQ ID NO: 356)
CCGACGCTGCACCCCAGCCTGACCG   (SEQ ID NO: 357)
CGACGCTGCACCCCAGCCTGACCGC   (SEQ ID NO: 358)
GACGCTGCACCCCAGCCTGACCGCG   (SEQ ID NO: 359)
ACGCTGCACCCCAGCCTGACCGCGA   (SEQ ID NO: 360)
CGCTGCACCCCAGCCTGACCGCGAA   (SEQ ID NO: 361)
```

FIGURE 2 (continued)

```
GCTGCACCCCAGCCTGACCGCGAAG  (SEQ ID NO: 362)
CTGCACCCCAGCCTGACCGCGAAGG  (SEQ ID NO: 363)
TGCACCCCAGCCTGACCGCGAAGGA  (SEQ ID NO: 364)
GCACCCCAGCCTGACCGCGAAGGAG  (SEQ ID NO: 365)
CACCCCAGCCTGACCGCGAAGGAGG  (SEQ ID NO: 366)
ACCCCAGCCTGACCGCGAAGGAGGC  (SEQ ID NO: 367)
CCCCAGCCTGACCGCGAAGGAGGCG  (SEQ ID NO: 368)
CCCAGCCTGACCGCGAAGGAGGCGC  (SEQ ID NO: 369)
CCAGCCTGACCGCGAAGGAGGCGCC  (SEQ ID NO: 370)
CAGCCTGACCGCGAAGGAGGCGCCC  (SEQ ID NO: 371)
AGCCTGACCGCGAAGGAGGCGCCCA  (SEQ ID NO: 372)
GCCTGACCGCGAAGGAGGCGCCCAT  (SEQ ID NO: 373)
CCTGACCGCGAAGGAGGCGCCCATG  (SEQ ID NO: 374)
CTGACCGCGAAGGAGGCGCCCATGG  (SEQ ID NO: 375)
TGACCGCGAAGGAGGCGCCCATGGT  (SEQ ID NO: 376)
GACCGCGAAGGAGGCGCCCATGGTG  (SEQ ID NO: 377)
ACCGCGAAGGAGGCGCCCATGGTGG  (SEQ ID NO: 378)
CCGCGAAGGAGGCGCCCATGGTGGT  (SEQ ID NO: 379)
CGCGAAGGAGGCGCCCATGGTGGTC  (SEQ ID NO: 380)
GCGAAGGAGGCGCCCATGGTGGTCA  (SEQ ID NO: 381)
CGAAGGAGGCGCCCATGGTGGTCAT  (SEQ ID NO: 382)
GAAGGAGGCGCCCATGGTGGTCATG  (SEQ ID NO: 383)
AAGGAGGCGCCCATGGTGGTCATGC  (SEQ ID NO: 384)
AGGAGGCGCCCATGGTGGTCATGCG  (SEQ ID NO: 385)
GGAGGCGCCCATGGTGGTCATGCGG  (SEQ ID NO: 386)
GAGGCGCCCATGGTGGTCATGCGGA  (SEQ ID NO: 387)
AGGCGCCCATGGTGGTCATGCGGAT  (SEQ ID NO: 388)
GGCGCCCATGGTGGTCATGCGGATG  (SEQ ID NO: 389)
GCGCCCATGGTGGTCATGCGGATGC  (SEQ ID NO: 390)
CGCCCATGGTGGTCATGCGGATGCT  (SEQ ID NO: 391)
GCCCATGGTGGTCATGCGGATGCTG  (SEQ ID NO: 392)
CCCATGGTGGTCATGCGGATGCTGC  (SEQ ID NO: 393)
CCATGGTGGTCATGCGGATGCTGCC  (SEQ ID NO: 394)
CATGGTGGTCATGCGGATGCTGCCG  (SEQ ID NO: 395)
ATGGTGGTCATGCGGATGCTGCCGT  (SEQ ID NO: 396)
TGGTGGTCATGCGGATGCTGCCGTT  (SEQ ID NO: 397)
GGTGGTCATGCGGATGCTGCCGTTC  (SEQ ID NO: 398)
GTGGTCATGCGGATGCTGCCGTTCC  (SEQ ID NO: 399)
TGGTCATGCGGATGCTGCCGTTCCT  (SEQ ID NO: 400)
GGTCATGCGGATGCTGCCGTTCCTA  (SEQ ID NO: 401)
GTCATGCGGATGCTGCCGTTCCTAA  (SEQ ID NO: 402)
TCATGCGGATGCTGCCGTTCCTAAT  (SEQ ID NO: 403)
CATGCGGATGCTGCCGTTCCTAATG  (SEQ ID NO: 404)
ATGCGGATGCTGCCGTTCCTAATGT  (SEQ ID NO: 405)
TGCGGATGCTGCCGTTCCTAATGTA  (SEQ ID NO: 406)
GCGGATGCTGCCGTTCCTAATGTAG  (SEQ ID NO: 407)
CGGATGCTGCCGTTCCTAATGTAGC  (SEQ ID NO: 408)
GGATGCTGCCGTTCCTAATGTAGCG  (SEQ ID NO: 409)
GATGCTGCCGTTCCTAATGTAGCGG  (SEQ ID NO: 410)
ATGCTGCCGTTCCTAATGTAGCGGG  (SEQ ID NO: 411)
TGCTGCCGTTCCTAATGTAGCGGGA  (SEQ ID NO: 412)
GCTGCCGTTCCTAATGTAGCGGGAC  (SEQ ID NO: 413)
CTGCCGTTCCTAATGTAGCGGGACT  (SEQ ID NO: 414)
TGCCGTTCCTAATGTAGCGGGACTT  (SEQ ID NO: 415)
GCCGTTCCTAATGTAGCGGGACTTT  (SEQ ID NO: 416)
CCGTTCCTAATGTAGCGGGACTTTC  (SEQ ID NO: 417)
CGTTCCTAATGTAGCGGGACTTTCT  (SEQ ID NO: 418)
```

FIGURE 2 (continued)

```
GTTCCTAATGTAGCGGGACTTTCTC  (SEQ ID NO: 419)
TTCCTAATGTAGCGGGACTTTCTCC  (SEQ ID NO: 420)
TCCTAATGTAGCGGGACTTTCTCCT  (SEQ ID NO: 421)
CCTAATGTAGCGGGACTTTCTCCTG  (SEQ ID NO: 422)
CTAATGTAGCGGGACTTTCTCCTGG  (SEQ ID NO: 423)
TAATGTAGCGGGACTTTCTCCTGGA  (SEQ ID NO: 424)
AATGTAGCGGGACTTTCTCCTGGAC  (SEQ ID NO: 425)
ATGTAGCGGGACTTTCTCCTGGACG  (SEQ ID NO: 426)
TGTAGCGGGACTTTCTCCTGGACGC  (SEQ ID NO: 427)
GTAGCGGGACTTTCTCCTGGACGCG  (SEQ ID NO: 428)
TAGCGGGACTTTCTCCTGGACGCGA  (SEQ ID NO: 429)
AGCGGGACTTTCTCCTGGACGCGAG  (SEQ ID NO: 430)
GCGGGACTTTCTCCTGGACGCGAGA  (SEQ ID NO: 431)
CGGGACTTTCTCCTGGACGCGAGAA  (SEQ ID NO: 432)
GGGACTTTCTCCTGGACGCGAGAAC  (SEQ ID NO: 433)
GGACTTTCTCCTGGACGCGAGAACC  (SEQ ID NO: 434)
GACTTTCTCCTGGACGCGAGAACCT  (SEQ ID NO: 435)
ACTTTCTCCTGGACGCGAGAACCTG  (SEQ ID NO: 436)
CTTTCTCCTGGACGCGAGAACCTGG  (SEQ ID NO: 437)
TTTCTCCTGGACGCGAGAACCTGGC  (SEQ ID NO: 438)
TTCTCCTGGACGCGAGAACCTGGCG  (SEQ ID NO: 439)
TCTCCTGGACGCGAGAACCTGGCGC  (SEQ ID NO: 440)
CTCCTGGACGCGAGAACCTGGCGCC  (SEQ ID NO: 441)
TCCTGGACGCGAGAACCTGGCGCCG  (SEQ ID NO: 442)
CCTGGACGCGAGAACCTGGCGCCGC  (SEQ ID NO: 443)
CTGGACGCGAGAACCTGGCGCCGCC  (SEQ ID NO: 444)
TGGACGCGAGAACCTGGCGCCGCCT  (SEQ ID NO: 445)
GGACGCGAGAACCTGGCGCCGCCTG  (SEQ ID NO: 446)
GACGCGAGAACCTGGCGCCGCCTGT  (SEQ ID NO: 447)
ACGCGAGAACCTGGCGCCGCCTGTA  (SEQ ID NO: 448)
CGCGAGAACCTGGCGCCGCCTGTAC  (SEQ ID NO: 449)
GCGAGAACCTGGCGCCGCCTGTACC  (SEQ ID NO: 450)
CGAGAACCTGGCGCCGCCTGTACCG  (SEQ ID NO: 451)
GAGAACCTGGCGCCGCCTGTACCGT  (SEQ ID NO: 452)
AGAACCTGGCGCCGCCTGTACCGTC  (SEQ ID NO: 453)
GAACCTGGCGCCGCCTGTACCGTCG  (SEQ ID NO: 454)
AACCTGGCGCCGCCTGTACCGTCGA  (SEQ ID NO: 455)
ACCTGGCGCCGCCTGTACCGTCGAG  (SEQ ID NO: 456)
CCTGGCGCCGCCTGTACCGTCGAGT  (SEQ ID NO: 457)
CTGGCGCCGCCTGTACCGTCGAGTC  (SEQ ID NO: 458)
TGGCGCCGCCTGTACCGTCGAGTCT  (SEQ ID NO: 459)
GGCGCCGCCTGTACCGTCGAGTCTG  (SEQ ID NO: 460)
GCGCCGCCTGTACCGTCGAGTCTGG  (SEQ ID NO: 461)
CGCCGCCTGTACCGTCGAGTCTGGT  (SEQ ID NO: 462)
GCCGCCTGTACCGTCGAGTCTGGTG  (SEQ ID NO: 463)
CCGCCTGTACCGTCGAGTCTGGTGG  (SEQ ID NO: 464)
CGCCTGTACCGTCGAGTCTGGTGGT  (SEQ ID NO: 465)
GCCTGTACCGTCGAGTCTGGTGGTT  (SEQ ID NO: 466)
CCTGTACCGTCGAGTCTGGTGGTTC  (SEQ ID NO: 467)
CTGTACCGTCGAGTCTGGTGGTTCG  (SEQ ID NO: 468)
TGTACCGTCGAGTCTGGTGGTTCGT  (SEQ ID NO: 469)
GTACCGTCGAGTCTGGTGGTTCGTG  (SEQ ID NO: 470)
TACCGTCGAGTCTGGTGGTTCGTGT  (SEQ ID NO: 471)
ACCGTCGAGTCTGGTGGTTCGTGTT  (SEQ ID NO: 472)
CCGTCGAGTCTGGTGGTTCGTGTTC  (SEQ ID NO: 473)
CGTCGAGTCTGGTGGTTCGTGTTCA  (SEQ ID NO: 474)
GTCGAGTCTGGTGGTTCGTGTTCAC  (SEQ ID NO: 475)
```

FIGURE 2 (continued)

| Sequence | SEQ ID NO |
|---|---|
| TCGAGTCTGGTGGTTCGTGTTCACC | 476 |
| CGAGTCTGGTGGTTCGTGTTCACCC | 477 |
| GAGTCTGGTGGTTCGTGTTCACCCT | 478 |
| AGTCTGGTGGTTCGTGTTCACCCTC | 479 |
| GTCTGGTGGTTCGTGTTCACCCTCC | 480 |
| TCTGGTGGTTCGTGTTCACCCTCCG | 481 |
| CTGGTGGTTCGTGTTCACCCTCCGC | 482 |
| TGGTGGTTCGTGTTCACCCTCCGCC | 483 |
| GGTGGTTCGTGTTCACCCTCCGCCG | 484 |
| GTGGTTCGTGTTCACCCTCCGCCGG | 485 |
| TGGTTCGTGTTCACCCTCCGCCGGG | 486 |
| GGTTCGTGTTCACCCTCCGCCGGGT | 487 |
| GTTCGTGTTCACCCTCCGCCGGGTA | 488 |
| TTCGTGTTCACCCTCCGCCGGGTAC | 489 |
| TCGTGTTCACCCTCCGCCGGGTACA | 490 |
| CGTGTTCACCCTCCGCCGGGTACAC | 491 |
| GTGTTCACCCTCCGCCGGGTACACC | 492 |
| TGTTCACCCTCCGCCGGGTACACCG | 493 |
| GTTCACCCTCCGCCGGGTACACCGC | 494 |
| TTCACCCTCCGCCGGGTACACCGCC | 495 |
| TCACCCTCCGCCGGGTACACCGCCT | 496 |
| CACCCTCCGCCGGGTACACCGCCTC | 497 |
| ACCCTCCGCCGGGTACACCGCCTCG | 498 |
| CCCTCCGCCGGGTACACCGCCTCGT | 499 |
| CCTCCGCCGGGTACACCGCCTCGTC | 500 |
| CTCCGCCGGGTACACCGCCTCGTCA | 501 |
| TCCGCCGGGTACACCGCCTCGTCAA | 502 |
| CCGCCGGGTACACCGCCTCGTCAAC | 503 |
| CGCCGGGTACACCGCCTCGTCAACT | 504 |
| GCCGGGTACACCGCCTCGTCAACTC | 505 |
| CCGGGTACACCGCCTCGTCAACTCT | 506 |
| CGGGTACACCGCCTCGTCAACTCTC | 507 |
| GGGTACACCGCCTCGTCAACTCTCG | 508 |
| GGTACACCGCCTCGTCAACTCTCGG | 509 |
| GTACACCGCCTCGTCAACTCTCGGA | 510 |
| TACACCGCCTCGTCAACTCTCGGAT | 511 |
| ACACCGCCTCGTCAACTCTCGGATG | 512 |
| CACCGCCTCGTCAACTCTCGGATGG | 513 |
| ACCGCCTCGTCAACTCTCGGATGGA | 514 |
| CCGCCTCGTCAACTCTCGGATGGAC | 515 |
| CGCCTCGTCAACTCTCGGATGGACC | 516 |
| GCCTCGTCAACTCTCGGATGGACCT | 517 |
| CCTCGTCAACTCTCGGATGGACCTC | 518 |
| CTCGTCAACTCTCGGATGGACCTCC | 519 |
| TCGTCAACTCTCGGATGGACCTCCC | 520 |
| CGTCAACTCTCGGATGGACCTCCCG | 521 |
| GTCAACTCTCGGATGGACCTCCCGT | 522 |
| TCAACTCTCGGATGGACCTCCCGTG | 523 |
| CAACTCTCGGATGGACCTCCCGTGC | 524 |
| AACTCTCGGATGGACCTCCCGTGCA | 525 |
| ACTCTCGGATGGACCTCCCGTGCAC | 526 |
| CTCTCGGATGGACCTCCCGTGCACG | 527 |
| TCTCGGATGGACCTCCCGTGCACGC | 528 |
| CTCGGATGGACCTCCCGTGCACGCA | 529 |
| TCGGATGGACCTCCCGTGCACGCAC | 530 |
| CGGATGGACCTCCCGTGCACGCACC | 531 |
| GGATGGACCTCCCGTGCACGCACCT | 532 |

FIGURE 2 (continued)

```
GATGGACCTCCCGTGCACGCACCTC  (SEQ ID NO: 533)
ATGGACCTCCCGTGCACGCACCTCA  (SEQ ID NO: 534)
TGGACCTCCCGTGCACGCACCTCAC  (SEQ ID NO: 535)
GGACCTCCCGTGCACGCACCTCACC  (SEQ ID NO: 536)
GACCTCCCGTGCACGCACCTCACCG  (SEQ ID NO: 537)
ACCTCCCGTGCACGCACCTCACCGA  (SEQ ID NO: 538)
CCTCCCGTGCACGCACCTCACCGAG  (SEQ ID NO: 539)
CTCCCGTGCACGCACCTCACCGAGG  (SEQ ID NO: 540)
TCCCGTGCACGCACCTCACCGAGGC  (SEQ ID NO: 541)
CCCGTGCACGCACCTCACCGAGGCG  (SEQ ID NO: 542)
CCGTGCACGCACCTCACCGAGGCGT  (SEQ ID NO: 543)
CGTGCACGCACCTCACCGAGGCGTC  (SEQ ID NO: 544)
GTGCACGCACCTCACCGAGGCGTCT  (SEQ ID NO: 545)
TGCACGCACCTCACCGAGGCGTCTA  (SEQ ID NO: 546)
GCACGCACCTCACCGAGGCGTCTAT  (SEQ ID NO: 547)
CACGCACCTCACCGAGGCGTCTATG  (SEQ ID NO: 548)
ACGCACCTCACCGAGGCGTCTATGG  (SEQ ID NO: 549)
CGCACCTCACCGAGGCGTCTATGGA  (SEQ ID NO: 550)
GCACCTCACCGAGGCGTCTATGGAC  (SEQ ID NO: 551)
CACCTCACCGAGGCGTCTATGGACC  (SEQ ID NO: 552)
ACCTCACCGAGGCGTCTATGGACCT  (SEQ ID NO: 553)
CCTCACCGAGGCGTCTATGGACCTC  (SEQ ID NO: 554)
CTCACCGAGGCGTCTATGGACCTCT  (SEQ ID NO: 555)
TCACCGAGGCGTCTATGGACCTCTT  (SEQ ID NO: 556)
CACCGAGGCGTCTATGGACCTCTTG  (SEQ ID NO: 557)
ACCGAGGCGTCTATGGACCTCTTGC  (SEQ ID NO: 558)
CCGAGGCGTCTATGGACCTCTTGCC  (SEQ ID NO: 559)
CGAGGCGTCTATGGACCTCTTGCCC  (SEQ ID NO: 560)
GAGGCGTCTATGGACCTCTTGCCCT  (SEQ ID NO: 561)
AGGCGTCTATGGACCTCTTGCCCTT  (SEQ ID NO: 562)
GGCGTCTATGGACCTCTTGCCCTTC  (SEQ ID NO: 563)
GCGTCTATGGACCTCTTGCCCTTCC  (SEQ ID NO: 564)
CGTCTATGGACCTCTTGCCCTTCCT  (SEQ ID NO: 565)
GTCTATGGACCTCTTGCCCTTCCTC  (SEQ ID NO: 566)
TCTATGGACCTCTTGCCCTTCCTCT  (SEQ ID NO: 567)
CTATGGACCTCTTGCCCTTCCTCTG  (SEQ ID NO: 568)
TATGGACCTCTTGCCCTTCCTCTGC  (SEQ ID NO: 569)
ATGGACCTCTTGCCCTTCCTCTGCG  (SEQ ID NO: 570)
TGGACCTCTTGCCCTTCCTCTGCGA  (SEQ ID NO: 571)
GGACCTCTTGCCCTTCCTCTGCGAC  (SEQ ID NO: 572)
GACCTCTTGCCCTTCCTCTGCGACG  (SEQ ID NO: 573)
ACCTCTTGCCCTTCCTCTGCGACGT  (SEQ ID NO: 574)
CCTCTTGCCCTTCCTCTGCGACGTC  (SEQ ID NO: 575)
CTCTTGCCCTTCCTCTGCGACGTCG  (SEQ ID NO: 576)
TCTTGCCCTTCCTCTGCGACGTCGC  (SEQ ID NO: 577)
CTTGCCCTTCCTCTGCGACGTCGCG  (SEQ ID NO: 578)
TTGCCCTTCCTCTGCGACGTCGCGT  (SEQ ID NO: 579)
TGCCCTTCCTCTGCGACGTCGCGTG  (SEQ ID NO: 580)
GCCCTTCCTCTGCGACGTCGCGTGC  (SEQ ID NO: 581)
CCCTTCCTCTGCGACGTCGCGTGCC  (SEQ ID NO: 582)
```

SEQUENCE LISTING

```
<160> NUMBER OF SEQ ID NOS: 582

<210> SEQ ID NO 1
<211> LENGTH: 25
<212> TYPE: DNA
<213> ORGANISM: Artificial Sequence
<220> FEATURE:
<223> OTHER INFORMATION: Probe

<400> SEQUENCE: 1 acagggtgt cgtgcaaaga acctc                                          25

<210> SEQ ID NO 2
<211> LENGTH: 25
<212> TYPE: DNA
<213> ORGANISM: Artificial Sequence
<220> FEATURE:
<223> OTHER INFORMATION: Probe

<400> SEQUENCE: 2
tccgcagata cctggagaac aggaa                                         25

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
tccgcagata cctggagaac aggaa                                         25

<210> SEQ ID NO 4
<211> LENGTH: 25
<212> TYPE: DNA
<213> ORGANISM: Artificial Sequence
<220> FEATURE:
```

<223> OTHER INFORMATION: Probe

<400> SEQUENCE: 4
tccagaggat gtttggctgc gacct                                25

<210> SEQ ID NO 5
<211> LENGTH: 25
<212> TYPE: DNA
<213> ORGANISM: Artificial Sequence
<220> FEATURE:
<223> OTHER INFORMATION: Probe

<400> SEQUENCE: 5
tccagaggat gtttggctgc gacct                                25

<210> SEQ ID NO 6
<211> LENGTH: 25
<212> TYPE: DNA
<213> ORGANISM: Artificial Sequence
<220> FEATURE:
<223> OTHER INFORMATION: Probe

<400> SEQUENCE: 6
tgtcgccgag tactggaaca gccag                                25

<210> SEQ ID NO 7
<211> LENGTH: 25
<212> TYPE: DNA
<213> ORGANISM: Artificial Sequence
<220> FEATURE:
<223> OTHER INFORMATION: Probe

<400> SEQUENCE: 7
tgtcgccgag tactggaaca gccag                                25

<210> SEQ ID NO 8
<211> LENGTH: 25
<212> TYPE: DNA
<213> ORGANISM: Artificial Sequence
<220> FEATURE:
<223> OTHER INFORMATION: Probe

<400> SEQUENCE: 8
ttcgacagcg acgtgggggga gttcc                               25

<210> SEQ ID NO 9
<211> LENGTH: 25
<212> TYPE: DNA
<213> ORGANISM: Artificial Sequence
<220> FEATURE:
<223> OTHER INFORMATION: Probe

<400> SEQUENCE: 9
ttcgacagcg acgtggggga gttcc                                25

<210> SEQ ID NO 10
<211> LENGTH: 25
<212> TYPE: DNA
<213> ORGANISM: Artificial Sequence
<220> FEATURE:
<223> OTHER INFORMATION: Probe

<400> SEQUENCE: 10
ttcgacagcg acgtggggga gttcc                                25

<210> SEQ ID NO 11

```
<211> LENGTH: 25
<212> TYPE: DNA
<213> ORGANISM: Artificial Sequence
<220> FEATURE:
<223> OTHER INFORMATION: Typical Reference Sequence for DRB allele

<400> SEQUENCE: 11
gtgtccccac agcacgtttc ttgtg                                          25

<210> SEQ ID NO 12
<211> LENGTH: 25
<212> TYPE: DNA
<213> ORGANISM: Artificial Sequence
<220> FEATURE:
<223> OTHER INFORMATION: Target Sequence

<400> SEQUENCE: 12
gtgtccccac agcacgtttc ttgtg                                          25

<210> SEQ ID NO 13
<211> LENGTH: 25
<212> TYPE: DNA
<213> ORGANISM: Artificial Sequence
<220> FEATURE:
<223> OTHER INFORMATION: Target Sequence

<400> SEQUENCE: 13
tgtccccaca gcacgtttct tgtgg                                          25

<210> SEQ ID NO 14
<211> LENGTH: 270
<212> TYPE: DNA
<213> ORGANISM: Homo sapiens

<400> SEQUENCE: 14
gctcccactc catgaggtat ttcttcacat ccgtgtcccg gcccggccgc ggggagcccc    60
gcttcatcgc cgtgggctac gtggacgaca cgcagttcgt gcggttcgac agcgacgccg   120
cgagccagag gatggagccg cgggcgccgt ggatagagca ggagggtccg gagtattggg   180
acggggagac acggaaagtg aaggcccact cacagactca ccgagtggac ctggggaccc   240
tgcgcggcta ctacaaccag agcgaggccg                                    270

<210> SEQ ID NO 15
<211> LENGTH: 276
<212> TYPE: DNA
<213> ORGANISM: Homo sapiens

<400> SEQUENCE: 15
gttctcacac cgtccagagg atgtatggct gcgacgtggg gtcggactgg cgcttcctcc    60
gcgggtacca ccagtacgcc tacgacggca aggattacat cgccctgaaa gaggacctgc   120
gctcttggac cgcggcggac atggcagctc agaccaccaa gcacaagtgg gaggcggccc   180
atgtggcgga gcagttgaga gcctacctgg agggcacgtg cgtggagtgg ctccgcagat   240
acctggagaa cgggaaggag acgctgcagc gcacgg                             276

<210> SEQ ID NO 16
<211> LENGTH: 19
<212> TYPE: DNA
<213> ORGANISM: Artificial Sequence
<220> FEATURE:
<223> OTHER INFORMATION: DNA probe

<400> SEQUENCE: 16
```
atcgatcgat cgatcgatc                                                19

<210> SEQ ID NO 17
<211> LENGTH: 9
<212> TYPE: DNA
<213> ORGANISM: Artificial Sequence
<220> FEATURE:
<223> OTHER INFORMATION: DNA probe

<400> SEQUENCE: 17 atcgatcga                                                            9

<210> SEQ ID NO 18
<211> LENGTH: 9
<212> TYPE: DNA
<213> ORGANISM: Artificial Sequence
<220> FEATURE:
<223> OTHER INFORMATION: DNA probe

<400> SEQUENCE: 18 tcgatcgat                                                            9

<210> SEQ ID NO 19
<211> LENGTH: 9
<212> TYPE: DNA
<213> ORGANISM: Artificial Sequence
<220> FEATURE:
<223> OTHER INFORMATION: DNA probe

<400> SEQUENCE: 19 cgatcgatc                                                            9

<210> SEQ ID NO 20
<211> LENGTH: 9
<212> TYPE: DNA
<213> ORGANISM: Artificial Sequence
<220> FEATURE:
<223> OTHER INFORMATION: DNA probe

<400> SEQUENCE: 20 gatcgatcg                                                            9

<210> SEQ ID NO 21
<211> LENGTH: 9
<212> TYPE: DNA
<213> ORGANISM: Artificial Sequence
<220> FEATURE:
<223> OTHER INFORMATION: DNA probe

<400> SEQUENCE: 21 atcgatcga                                                            9

<210> SEQ ID NO 22
<211> LENGTH: 9
<212> TYPE: DNA
<213> ORGANISM: Artificial Sequence
<220> FEATURE:
<223> OTHER INFORMATION: DNA probe

<400> SEQUENCE: 22 tcgatcgat                                                            9

<210> SEQ ID NO 23
<211> LENGTH: 9
<212> TYPE: DNA
<213> ORGANISM: Artificial Sequence
<220> FEATURE:

```
<223> OTHER INFORMATION: DNA probe

<400> SEQUENCE: 23 cgatcgatc                                                                9

<210> SEQ ID NO 24
<211> LENGTH: 9
<212> TYPE: DNA
<213> ORGANISM: Artificial Sequence
<220> FEATURE:
<223> OTHER INFORMATION: DNA probe

<400> SEQUENCE: 24 gatcgatcg                                                                9

<210> SEQ ID NO 25
<211> LENGTH: 9
<212> TYPE: DNA
<213> ORGANISM: Artificial Sequence
<220> FEATURE:
<223> OTHER INFORMATION: DNA probe

<400> SEQUENCE: 25 atcgatcga                                                                9

<210> SEQ ID NO 26
<211> LENGTH: 9
<212> TYPE: DNA
<213> ORGANISM: Artificial Sequence
<220> FEATURE:
<223> OTHER INFORMATION: DNA probe

<400> SEQUENCE: 26 tcgatcgat                                                                9

<210> SEQ ID NO 27
<211> LENGTH: 9
<212> TYPE: DNA
<213> ORGANISM: Artificial Sequence
<220> FEATURE:
<223> OTHER INFORMATION: DNA probe

<400> SEQUENCE: 27 cgatcgatc                                                                9

<210> SEQ ID NO 28
<211> LENGTH: 19
<212> TYPE: DNA
<213> ORGANISM: Artificial Sequence
<220> FEATURE:
<223> OTHER INFORMATION: DNA probe

<400> SEQUENCE: 28
atcgatcgat ggatcgatc                                                    19

<210> SEQ ID NO 29
<211> LENGTH: 9
<212> TYPE: DNA
<213> ORGANISM: Artificial Sequence
<220> FEATURE:
<223> OTHER INFORMATION: DNA probe

<400> SEQUENCE: 29 atcgatcga                                                                9

<210> SEQ ID NO 30
```

```
<211> LENGTH: 9
<212> TYPE: DNA
<213> ORGANISM: Artificial Sequence
<220> FEATURE:
<223> OTHER INFORMATION: DNA probe

<400> SEQUENCE: 30 tcgatcgat                                                                 9

<210> SEQ ID NO 31
<211> LENGTH: 9
<212> TYPE: DNA
<213> ORGANISM: Artificial Sequence
<220> FEATURE:
<223> OTHER INFORMATION: DNA probe

<400> SEQUENCE: 31 cgatcgatg                                                                 9

<210> SEQ ID NO 32
<211> LENGTH: 9
<212> TYPE: DNA
<213> ORGANISM: Artificial Sequence
<220> FEATURE:
<223> OTHER INFORMATION: DNA probe

<400> SEQUENCE: 32 gatcgatgg                                                                 9

<210> SEQ ID NO 33
<211> LENGTH: 9
<212> TYPE: DNA
<213> ORGANISM: Artificial Sequence
<220> FEATURE:
<223> OTHER INFORMATION: DNA probe

<400> SEQUENCE: 33 atcgatgga                                                                 9

<210> SEQ ID NO 34
<211> LENGTH: 9
<212> TYPE: DNA
<213> ORGANISM: Artificial Sequence
<220> FEATURE:
<223> OTHER INFORMATION: DNA probe

<400> SEQUENCE: 34 tcgatggat                                                                 9

<210> SEQ ID NO 35
<211> LENGTH: 9
<212> TYPE: DNA
<213> ORGANISM: Artificial Sequence
<220> FEATURE:
<223> OTHER INFORMATION: DNA probe

<400> SEQUENCE: 35 cgatggatc                                                                 9

<210> SEQ ID NO 36
<211> LENGTH: 9
<212> TYPE: DNA
<213> ORGANISM: Artificial Sequence
<220> FEATURE:
<223> OTHER INFORMATION: DNA probe

<400> SEQUENCE: 36
``` gatggatcg                                                      9

<210> SEQ ID NO 37
<211> LENGTH: 9
<212> TYPE: DNA
<213> ORGANISM: Artificial Sequence
<220> FEATURE:
<223> OTHER INFORMATION: DNA probe

<400> SEQUENCE: 37 atggatcga                                                      9

<210> SEQ ID NO 38
<211> LENGTH: 9
<212> TYPE: DNA
<213> ORGANISM: Artificial Sequence
<220> FEATURE:
<223> OTHER INFORMATION: DNA probe

<400> SEQUENCE: 38 tggatcgat                                                      9

<210> SEQ ID NO 39
<211> LENGTH: 9
<212> TYPE: DNA
<213> ORGANISM: Artificial Sequence
<220> FEATURE:
<223> OTHER INFORMATION: DNA probe

<400> SEQUENCE: 39 ggatcgatc                                                      9

<210> SEQ ID NO 40
<211> LENGTH: 19
<212> TYPE: DNA
<213> ORGANISM: Artificial Sequence
<220> FEATURE:
<223> OTHER INFORMATION: DNA probe

<400> SEQUENCE: 40
atcgatcgat cgatccatc                                          19

<210> SEQ ID NO 41
<211> LENGTH: 9
<212> TYPE: DNA
<213> ORGANISM: Artificial Sequence
<220> FEATURE:
<223> OTHER INFORMATION: DNA probe

<400> SEQUENCE: 41 atcgatcga                                                      9

<210> SEQ ID NO 42
<211> LENGTH: 9
<212> TYPE: DNA
<213> ORGANISM: Artificial Sequence
<220> FEATURE:
<223> OTHER INFORMATION: DNA probe

<400> SEQUENCE: 42 tcgatcgat                                                      9

<210> SEQ ID NO 43
<211> LENGTH: 9
<212> TYPE: DNA
<213> ORGANISM: Artificial Sequence
<220> FEATURE:

<223> OTHER INFORMATION: DNA probe

<400> SEQUENCE: 43 cgatcgatc                                                                                          9

<210> SEQ ID NO 44
<211> LENGTH: 9
<212> TYPE: DNA
<213> ORGANISM: Artificial Sequence
<220> FEATURE:
<223> OTHER INFORMATION: DNA probe

<400> SEQUENCE: 44 gatcgatcg                                                                                          9

<210> SEQ ID NO 45
<211> LENGTH: 9
<212> TYPE: DNA
<213> ORGANISM: Artificial Sequence
<220> FEATURE:
<223> OTHER INFORMATION: DNA probe

<400> SEQUENCE: 45 atcgatcga                                                                                          9

<210> SEQ ID NO 46
<211> LENGTH: 9
<212> TYPE: DNA
<213> ORGANISM: Artificial Sequence
<220> FEATURE:
<223> OTHER INFORMATION: DNA probe

<400> SEQUENCE: 46 tcgatcgat                                                                                          9

<210> SEQ ID NO 47
<211> LENGTH: 9
<212> TYPE: DNA
<213> ORGANISM: Artificial Sequence
<220> FEATURE:
<223> OTHER INFORMATION: DNA probe

<400> SEQUENCE: 47 cgatcgatc                                                                                          9

<210> SEQ ID NO 48
<211> LENGTH: 9
<212> TYPE: DNA
<213> ORGANISM: Artificial Sequence
<220> FEATURE:
<223> OTHER INFORMATION: DNA probe

<400> SEQUENCE: 48 gatcgatcc                                                                                          9

<210> SEQ ID NO 49
<211> LENGTH: 9
<212> TYPE: DNA
<213> ORGANISM: Artificial Sequence
<220> FEATURE:
<223> OTHER INFORMATION: DNA probe

<400> SEQUENCE: 49 atcgatcca                                                                                          9

<210> SEQ ID NO 50

```
<211> LENGTH: 9
<212> TYPE: DNA
<213> ORGANISM: Artificial Sequence
<220> FEATURE:
<223> OTHER INFORMATION: DNA probe

<400> SEQUENCE: 50 tcgatccat                                                                9

<210> SEQ ID NO 51
<211> LENGTH: 9
<212> TYPE: DNA
<213> ORGANISM: Artificial Sequence
<220> FEATURE:
<223> OTHER INFORMATION: DNA probe

<400> SEQUENCE: 51 cgatccatc                                                                9

<210> SEQ ID NO 52
<211> LENGTH: 9
<212> TYPE: DNA
<213> ORGANISM: Artificial Sequence
<220> FEATURE:
<223> OTHER INFORMATION: DNA probe

<400> SEQUENCE: 52 atcgatcga                                                                9

<210> SEQ ID NO 53
<211> LENGTH: 9
<212> TYPE: DNA
<213> ORGANISM: Artificial Sequence
<220> FEATURE:
<223> OTHER INFORMATION: DNA probe

<400> SEQUENCE: 53 tcgatcgat                                                                9

<210> SEQ ID NO 54
<211> LENGTH: 9
<212> TYPE: DNA
<213> ORGANISM: Artificial Sequence
<220> FEATURE:
<223> OTHER INFORMATION: DNA probe

<400> SEQUENCE: 54 cgatcgatc                                                                9

<210> SEQ ID NO 55
<211> LENGTH: 9
<212> TYPE: DNA
<213> ORGANISM: Artificial Sequence
<220> FEATURE:
<223> OTHER INFORMATION: DNA probe

<400> SEQUENCE: 55 gatcgatcg                                                                9

<210> SEQ ID NO 56
<211> LENGTH: 9
<212> TYPE: DNA
<213> ORGANISM: Artificial Sequence
<220> FEATURE:
<223> OTHER INFORMATION: DNA probe

<400> SEQUENCE: 56
```

-continued atcgatcga                                                                        9

<210> SEQ ID NO 57
<211> LENGTH: 9
<212> TYPE: DNA
<213> ORGANISM: Artificial Sequence
<220> FEATURE:
<223> OTHER INFORMATION: DNA probe

<400> SEQUENCE: 57 tcgatcgat                                                                        9

<210> SEQ ID NO 58
<211> LENGTH: 9
<212> TYPE: DNA
<213> ORGANISM: Artificial Sequence
<220> FEATURE:
<223> OTHER INFORMATION: DNA probe

<400> SEQUENCE: 58 cgatcgatc                                                                        9

<210> SEQ ID NO 59
<211> LENGTH: 9
<212> TYPE: DNA
<213> ORGANISM: Artificial Sequence
<220> FEATURE:
<223> OTHER INFORMATION: DNA probe

<400> SEQUENCE: 59 gatcgatcg                                                                        9

<210> SEQ ID NO 60
<211> LENGTH: 9
<212> TYPE: DNA
<213> ORGANISM: Artificial Sequence
<220> FEATURE:
<223> OTHER INFORMATION: DNA probe

<400> SEQUENCE: 60 atcgatcga                                                                        9

<210> SEQ ID NO 61
<211> LENGTH: 9
<212> TYPE: DNA
<213> ORGANISM: Artificial Sequence
<220> FEATURE:
<223> OTHER INFORMATION: DNA probe

<400> SEQUENCE: 61 tcgatcgat                                                                        9

<210> SEQ ID NO 62
<211> LENGTH: 9
<212> TYPE: DNA
<213> ORGANISM: Artificial Sequence
<220> FEATURE:
<223> OTHER INFORMATION: DNA probe

<400> SEQUENCE: 62 cgatcgatc                                                                        9

<210> SEQ ID NO 63
<211> LENGTH: 9
<212> TYPE: DNA
<213> ORGANISM: Artificial Sequence
<220> FEATURE:

-continued

<223> OTHER INFORMATION: DNA probe

<400> SEQUENCE: 63 atcgatcga                                                                 9

<210> SEQ ID NO 64
<211> LENGTH: 9
<212> TYPE: DNA
<213> ORGANISM: Artificial Sequence
<220> FEATURE:
<223> OTHER INFORMATION: DNA probe

<400> SEQUENCE: 64 tcgatcgat                                                                 9

<210> SEQ ID NO 65
<211> LENGTH: 9
<212> TYPE: DNA
<213> ORGANISM: Artificial Sequence
<220> FEATURE:
<223> OTHER INFORMATION: DNA probe

<400> SEQUENCE: 65 cgatcgatg                                                                 9

<210> SEQ ID NO 66
<211> LENGTH: 9
<212> TYPE: DNA
<213> ORGANISM: Artificial Sequence
<220> FEATURE:
<223> OTHER INFORMATION: DNA probe

<400> SEQUENCE: 66 gatcgatgg                                                                 9

<210> SEQ ID NO 67
<211> LENGTH: 9
<212> TYPE: DNA
<213> ORGANISM: Artificial Sequence
<220> FEATURE:
<223> OTHER INFORMATION: DNA probe

<400> SEQUENCE: 67 atcgatgga                                                                 9

<210> SEQ ID NO 68
<211> LENGTH: 9
<212> TYPE: DNA
<213> ORGANISM: Artificial Sequence
<220> FEATURE:
<223> OTHER INFORMATION: DNA probe

<400> SEQUENCE: 68 tcgatggat                                                                 9

<210> SEQ ID NO 69
<211> LENGTH: 9
<212> TYPE: DNA
<213> ORGANISM: Artificial Sequence
<220> FEATURE:
<223> OTHER INFORMATION: DNA probe

<400> SEQUENCE: 69 cgatggatc                                                                 9

<210> SEQ ID NO 70

<211> LENGTH: 9
<212> TYPE: DNA
<213> ORGANISM: Artificial Sequence
<220> FEATURE:
<223> OTHER INFORMATION: DNA probe

<400> SEQUENCE: 70 gatggatcg                                                                9

<210> SEQ ID NO 71
<211> LENGTH: 9
<212> TYPE: DNA
<213> ORGANISM: Artificial Sequence
<220> FEATURE:
<223> OTHER INFORMATION: DNA probe

<400> SEQUENCE: 71 atggatcga                                                                9

<210> SEQ ID NO 72
<211> LENGTH: 9
<212> TYPE: DNA
<213> ORGANISM: Artificial Sequence
<220> FEATURE:
<223> OTHER INFORMATION: DNA probe

<400> SEQUENCE: 72 tggatcgat                                                                9

<210> SEQ ID NO 73
<211> LENGTH: 9
<212> TYPE: DNA
<213> ORGANISM: Artificial Sequence
<220> FEATURE:
<223> OTHER INFORMATION: DNA probe

<400> SEQUENCE: 73 ggatcgatc                                                                9

<210> SEQ ID NO 74
<211> LENGTH: 9
<212> TYPE: DNA
<213> ORGANISM: Artificial Sequence
<220> FEATURE:
<223> OTHER INFORMATION: DNA probe

<400> SEQUENCE: 74 atcgatcga                                                                9

<210> SEQ ID NO 75
<211> LENGTH: 9
<212> TYPE: DNA
<213> ORGANISM: Artificial Sequence
<220> FEATURE:
<223> OTHER INFORMATION: DNA probe

<400> SEQUENCE: 75 tcgatcgat                                                                9

<210> SEQ ID NO 76
<211> LENGTH: 9
<212> TYPE: DNA
<213> ORGANISM: Artificial Sequence
<220> FEATURE:
<223> OTHER INFORMATION: DNA probe

<400> SEQUENCE: 76 cgatcgatc                                                          9

<210> SEQ ID NO 77
<211> LENGTH: 9
<212> TYPE: DNA
<213> ORGANISM: Artificial Sequence
<220> FEATURE:
<223> OTHER INFORMATION: DNA probe

<400> SEQUENCE: 77 gatcgatcg                                                          9

<210> SEQ ID NO 78
<211> LENGTH: 9
<212> TYPE: DNA
<213> ORGANISM: Artificial Sequence
<220> FEATURE:
<223> OTHER INFORMATION: DNA probe

<400> SEQUENCE: 78 atcgatcga                                                          9

<210> SEQ ID NO 79
<211> LENGTH: 9
<212> TYPE: DNA
<213> ORGANISM: Artificial Sequence
<220> FEATURE:
<223> OTHER INFORMATION: DNA probe

<400> SEQUENCE: 79 tcgatcgat                                                          9

<210> SEQ ID NO 80
<211> LENGTH: 9
<212> TYPE: DNA
<213> ORGANISM: Artificial Sequence
<220> FEATURE:
<223> OTHER INFORMATION: DNA probe

<400> SEQUENCE: 80 cgatcgatc                                                          9

<210> SEQ ID NO 81
<211> LENGTH: 9
<212> TYPE: DNA
<213> ORGANISM: Artificial Sequence
<220> FEATURE:
<223> OTHER INFORMATION: DNA probe

<400> SEQUENCE: 81 gatcgatcc                                                          9

<210> SEQ ID NO 82
<211> LENGTH: 9
<212> TYPE: DNA
<213> ORGANISM: Artificial Sequence
<220> FEATURE:
<223> OTHER INFORMATION: DNA probe

<400> SEQUENCE: 82 atcgatcca                                                          9

<210> SEQ ID NO 83
<211> LENGTH: 9
<212> TYPE: DNA
<213> ORGANISM: Artificial Sequence
<220> FEATURE:

<223> OTHER INFORMATION: DNA probe

<400> SEQUENCE: 83 tcgatccat                                                                                          9

<210> SEQ ID NO 84
<211> LENGTH: 9
<212> TYPE: DNA
<213> ORGANISM: Artificial Sequence
<220> FEATURE:
<223> OTHER INFORMATION: DNA probe

<400> SEQUENCE: 84 cgatccatc                                                                                          9

<210> SEQ ID NO 85
<211> LENGTH: 25
<212> TYPE: DNA
<213> ORGANISM: Artificial Sequence
<220> FEATURE:
<223> OTHER INFORMATION: DNA probe

<400> SEQUENCE: 85
cgagggtgag gtactccata aagaa                                                                        25

<210> SEQ ID NO 86
<211> LENGTH: 25
<212> TYPE: DNA
<213> ORGANISM: Artificial Sequence
<220> FEATURE:
<223> OTHER INFORMATION: DNA probe

<400> SEQUENCE: 86
gagggtgagg tactccataa agaag                                                                        25

<210> SEQ ID NO 87
<211> LENGTH: 25
<212> TYPE: DNA
<213> ORGANISM: Artificial Sequence
<220> FEATURE:
<223> OTHER INFORMATION: DNA probe

<400> SEQUENCE: 87
agggtgaggt actccataaa gaagt                                                                        25

<210> SEQ ID NO 88
<211> LENGTH: 25
<212> TYPE: DNA
<213> ORGANISM: Artificial Sequence
<220> FEATURE:
<223> OTHER INFORMATION: DNA probe

<400> SEQUENCE: 88
gggtgaggta ctccataaag aagtg                                                                        25

<210> SEQ ID NO 89
<211> LENGTH: 25
<212> TYPE: DNA
<213> ORGANISM: Artificial Sequence
<220> FEATURE:
<223> OTHER INFORMATION: DNA probe

<400> SEQUENCE: 89
ggtgaggtac tccataaaga agtgt                                                                        25

<210> SEQ ID NO 90

<211> LENGTH: 25
<212> TYPE: DNA
<213> ORGANISM: Artificial Sequence
<220> FEATURE:
<223> OTHER INFORMATION: DNA probe

<400> SEQUENCE: 90
gtgaggtact ccataaagaa gtgta                                   25

<210> SEQ ID NO 91
<211> LENGTH: 25
<212> TYPE: DNA
<213> ORGANISM: Artificial Sequence
<220> FEATURE:
<223> OTHER INFORMATION: DNA probe

<400> SEQUENCE: 91
tgaggtactc cataaagaag tgtag                                   25

<210> SEQ ID NO 92
<211> LENGTH: 25
<212> TYPE: DNA
<213> ORGANISM: Artificial Sequence
<220> FEATURE:
<223> OTHER INFORMATION: DNA probe

<400> SEQUENCE: 92
gaggtactcc ataaagaagt gtagg                                   25

<210> SEQ ID NO 93
<211> LENGTH: 25
<212> TYPE: DNA
<213> ORGANISM: Artificial Sequence
<220> FEATURE:
<223> OTHER INFORMATION: DNA probe

<400> SEQUENCE: 93
aggtactcca taaagaagtg taggc                                   25

<210> SEQ ID NO 94
<211> LENGTH: 25
<212> TYPE: DNA
<213> ORGANISM: Artificial Sequence
<220> FEATURE:
<223> OTHER INFORMATION: DNA probe

<400> SEQUENCE: 94
ggtactccat aaagaagtgt aggca                                   25

<210> SEQ ID NO 95
<211> LENGTH: 25
<212> TYPE: DNA
<213> ORGANISM: Artificial Sequence
<220> FEATURE:
<223> OTHER INFORMATION: DNA probe

<400> SEQUENCE: 95
gtactccata aagaagtgta ggcac                                   25

<210> SEQ ID NO 96
<211> LENGTH: 25
<212> TYPE: DNA
<213> ORGANISM: Artificial Sequence
<220> FEATURE:
<223> OTHER INFORMATION: DNA probe

<400> SEQUENCE: 96
tactccataa agaagtgtag gcaca                                              25

<210> SEQ ID NO 97
<211> LENGTH: 25
<212> TYPE: DNA
<213> ORGANISM: Artificial Sequence
<220> FEATURE:
<223> OTHER INFORMATION: DNA probe

<400> SEQUENCE: 97
actccataaa gaagtgtagg cacag                                              25

<210> SEQ ID NO 98
<211> LENGTH: 25
<212> TYPE: DNA
<213> ORGANISM: Artificial Sequence
<220> FEATURE:
<223> OTHER INFORMATION: DNA probe

<400> SEQUENCE: 98
ctccataaag aagtgtaggc acagg                                              25

<210> SEQ ID NO 99
<211> LENGTH: 25
<212> TYPE: DNA
<213> ORGANISM: Artificial Sequence
<220> FEATURE:
<223> OTHER INFORMATION: DNA probe

<400> SEQUENCE: 99
tccataaaga agtgtaggca caggg                                              25

<210> SEQ ID NO 100
<211> LENGTH: 25
<212> TYPE: DNA
<213> ORGANISM: Artificial Sequence
<220> FEATURE:
<223> OTHER INFORMATION: DNA probe

<400> SEQUENCE: 100
ccataaagaa gtgtaggcac agggc                                              25

<210> SEQ ID NO 101
<211> LENGTH: 25
<212> TYPE: DNA
<213> ORGANISM: Artificial Sequence
<220> FEATURE:
<223> OTHER INFORMATION: DNA probe

<400> SEQUENCE: 101
cataaagaag tgtaggcaca gggcc                                              25

<210> SEQ ID NO 102
<211> LENGTH: 25
<212> TYPE: DNA
<213> ORGANISM: Artificial Sequence
<220> FEATURE:
<223> OTHER INFORMATION: DNA probe

<400> SEQUENCE: 102
ataaagaagt gtaggcacag ggccg                                              25

<210> SEQ ID NO 103
<211> LENGTH: 25
<212> TYPE: DNA
<213> ORGANISM: Artificial Sequence
<220> FEATURE:

-continued

<223> OTHER INFORMATION: DNA probe

<400> SEQUENCE: 103
taaagaagtg taggcacagg gccgg                                  25

<210> SEQ ID NO 104
<211> LENGTH: 25
<212> TYPE: DNA
<213> ORGANISM: Artificial Sequence
<220> FEATURE:
<223> OTHER INFORMATION: DNA probe

<400> SEQUENCE: 104
aaagaagtgt aggcacaggg ccggg                                  25

<210> SEQ ID NO 105
<211> LENGTH: 25
<212> TYPE: DNA
<213> ORGANISM: Artificial Sequence
<220> FEATURE:
<223> OTHER INFORMATION: DNA probe

<400> SEQUENCE: 105
aagaagtgta ggcacagggc cgggc                                  25

<210> SEQ ID NO 106
<211> LENGTH: 25
<212> TYPE: DNA
<213> ORGANISM: Artificial Sequence
<220> FEATURE:
<223> OTHER INFORMATION: DNA probe

<400> SEQUENCE: 106
agaagtgtag gcacagggcc gggcc                                  25

<210> SEQ ID NO 107
<211> LENGTH: 25
<212> TYPE: DNA
<213> ORGANISM: Artificial Sequence
<220> FEATURE:
<223> OTHER INFORMATION: DNA probe

<400> SEQUENCE: 107
gaagtgtagg cacagggccg ggccg                                  25

<210> SEQ ID NO 108
<211> LENGTH: 25
<212> TYPE: DNA
<213> ORGANISM: Artificial Sequence
<220> FEATURE:
<223> OTHER INFORMATION: DNA probe

<400> SEQUENCE: 108
aagtgtaggc acagggccgg gccgg                                  25

<210> SEQ ID NO 109
<211> LENGTH: 25
<212> TYPE: DNA
<213> ORGANISM: Artificial Sequence
<220> FEATURE:
<223> OTHER INFORMATION: DNA probe

<400> SEQUENCE: 109
agtgtaggca cagggccggg ccggc                                  25

<210> SEQ ID NO 110

```
<211> LENGTH: 25
<212> TYPE: DNA
<213> ORGANISM: Artificial Sequence
<220> FEATURE:
<223> OTHER INFORMATION: DNA probe

<400> SEQUENCE: 110
gtgtaggcac agggccgggc cggcg                                         25

<210> SEQ ID NO 111
<211> LENGTH: 25
<212> TYPE: DNA
<213> ORGANISM: Artificial Sequence
<220> FEATURE:
<223> OTHER INFORMATION: DNA probe

<400> SEQUENCE: 111
tgtaggcaca gggccgggcc ggcgc                                         25

<210> SEQ ID NO 112
<211> LENGTH: 25
<212> TYPE: DNA
<213> ORGANISM: Artificial Sequence
<220> FEATURE:
<223> OTHER INFORMATION: DNA probe

<400> SEQUENCE: 112
gtaggcacag ggccgggccg gcgcc                                         25

<210> SEQ ID NO 113
<211> LENGTH: 25
<212> TYPE: DNA
<213> ORGANISM: Artificial Sequence
<220> FEATURE:
<223> OTHER INFORMATION: DNA probe

<400> SEQUENCE: 113
taggcacagg gccgggccgg cgccc                                         25

<210> SEQ ID NO 114
<211> LENGTH: 25
<212> TYPE: DNA
<213> ORGANISM: Artificial Sequence
<220> FEATURE:
<223> OTHER INFORMATION: DNA probe

<400> SEQUENCE: 114
aggcacaggg ccgggccggc gcccc                                         25

<210> SEQ ID NO 115
<211> LENGTH: 25
<212> TYPE: DNA
<213> ORGANISM: Artificial Sequence
<220> FEATURE:
<223> OTHER INFORMATION: DNA probe

<400> SEQUENCE: 115
ggcacagggc cgggccggcg cccct                                         25

<210> SEQ ID NO 116
<211> LENGTH: 25
<212> TYPE: DNA
<213> ORGANISM: Artificial Sequence
<220> FEATURE:
<223> OTHER INFORMATION: DNA probe

<400> SEQUENCE: 116
```

```
gcacagggcc gggccggcgc ccctc                                              25
```

<210> SEQ ID NO 117
<211> LENGTH: 25
<212> TYPE: DNA
<213> ORGANISM: Artificial Sequence
<220> FEATURE:
<223> OTHER INFORMATION: DNA probe

<400> SEQUENCE: 117

```
cacagggccg ggccggcgcc cctcg                                              25
```

<210> SEQ ID NO 118
<211> LENGTH: 25
<212> TYPE: DNA
<213> ORGANISM: Artificial Sequence
<220> FEATURE:
<223> OTHER INFORMATION: DNA probe

<400> SEQUENCE: 118

```
acagggccgg gccggcgccc ctcgg                                              25
```

<210> SEQ ID NO 119
<211> LENGTH: 25
<212> TYPE: DNA
<213> ORGANISM: Artificial Sequence
<220> FEATURE:
<223> OTHER INFORMATION: DNA probe

<400> SEQUENCE: 119

```
cagggccggg ccggcgcccc tcggg                                              25
```

<210> SEQ ID NO 120
<211> LENGTH: 25
<212> TYPE: DNA
<213> ORGANISM: Artificial Sequence
<220> FEATURE:
<223> OTHER INFORMATION: DNA probe

<400> SEQUENCE: 120

```
agggccgggc cggcgcccct cgggg                                              25
```

<210> SEQ ID NO 121
<211> LENGTH: 25
<212> TYPE: DNA
<213> ORGANISM: Artificial Sequence
<220> FEATURE:
<223> OTHER INFORMATION: DNA probe

<400> SEQUENCE: 121

```
gggccgggcc ggcgcccctc ggggc                                              25
```

<210> SEQ ID NO 122
<211> LENGTH: 25
<212> TYPE: DNA
<213> ORGANISM: Artificial Sequence
<220> FEATURE:
<223> OTHER INFORMATION: DNA probe

<400> SEQUENCE: 122

```
ggccgggccg gcgcccctcg ggcg                                               25
```

<210> SEQ ID NO 123
<211> LENGTH: 25
<212> TYPE: DNA
<213> ORGANISM: Artificial Sequence
<220> FEATURE:

<223> OTHER INFORMATION: DNA probe

<400> SEQUENCE: 123
gccgggccgg cgccctcgg ggcga                                    25

<210> SEQ ID NO 124
<211> LENGTH: 25
<212> TYPE: DNA
<213> ORGANISM: Artificial Sequence
<220> FEATURE:
<223> OTHER INFORMATION: DNA probe

<400> SEQUENCE: 124
ccgggccggc gccctcggg gcgaa                                    25

<210> SEQ ID NO 125
<211> LENGTH: 25
<212> TYPE: DNA
<213> ORGANISM: Artificial Sequence
<220> FEATURE:
<223> OTHER INFORMATION: DNA probe

<400> SEQUENCE: 125
cgggccggcg ccctcgggg cgaag                                    25

<210> SEQ ID NO 126
<211> LENGTH: 25
<212> TYPE: DNA
<213> ORGANISM: Artificial Sequence
<220> FEATURE:
<223> OTHER INFORMATION: DNA probe

<400> SEQUENCE: 126
gggccggcgc cctcggggc gaagt                                    25

<210> SEQ ID NO 127
<211> LENGTH: 25
<212> TYPE: DNA
<213> ORGANISM: Artificial Sequence
<220> FEATURE:
<223> OTHER INFORMATION: DNA probe

<400> SEQUENCE: 127
ggccggcgcc cctcggggcg aagta                                   25

<210> SEQ ID NO 128
<211> LENGTH: 25
<212> TYPE: DNA
<213> ORGANISM: Artificial Sequence
<220> FEATURE:
<223> OTHER INFORMATION: DNA probe

<400> SEQUENCE: 128
gccggcgccc ctcggggcga agtag                                   25

<210> SEQ ID NO 129
<211> LENGTH: 25
<212> TYPE: DNA
<213> ORGANISM: Artificial Sequence
<220> FEATURE:
<223> OTHER INFORMATION: DNA probe

<400> SEQUENCE: 129
ccggcgcccc tcggggcgaa gtagc                                   25

<210> SEQ ID NO 130

```
<211> LENGTH: 25
<212> TYPE: DNA
<213> ORGANISM: Artificial Sequence
<220> FEATURE:
<223> OTHER INFORMATION: DNA probe

<400> SEQUENCE: 130
cggcgcccct cggggcgaag tagcg                                              25

<210> SEQ ID NO 131
<211> LENGTH: 25
<212> TYPE: DNA
<213> ORGANISM: Artificial Sequence
<220> FEATURE:
<223> OTHER INFORMATION: DNA probe

<400> SEQUENCE: 131
ggcgcccctc ggggcgaagt agcgg                                              25

<210> SEQ ID NO 132
<211> LENGTH: 25
<212> TYPE: DNA
<213> ORGANISM: Artificial Sequence
<220> FEATURE:
<223> OTHER INFORMATION: DNA probe

<400> SEQUENCE: 132
gcgcccctcg gggcgaagta gcggc                                              25

<210> SEQ ID NO 133
<211> LENGTH: 25
<212> TYPE: DNA
<213> ORGANISM: Artificial Sequence
<220> FEATURE:
<223> OTHER INFORMATION: DNA probe

<400> SEQUENCE: 133
cgcccctcgg ggcgaagtag cggca                                              25

<210> SEQ ID NO 134
<211> LENGTH: 25
<212> TYPE: DNA
<213> ORGANISM: Artificial Sequence
<220> FEATURE:
<223> OTHER INFORMATION: DNA probe

<400> SEQUENCE: 134
gcccctcggg gcgaagtagc ggcac                                              25

<210> SEQ ID NO 135
<211> LENGTH: 25
<212> TYPE: DNA
<213> ORGANISM: Artificial Sequence
<220> FEATURE:
<223> OTHER INFORMATION: DNA probe

<400> SEQUENCE: 135
cccctcgggg cgaagtagcg gcacc                                              25

<210> SEQ ID NO 136
<211> LENGTH: 25
<212> TYPE: DNA
<213> ORGANISM: Artificial Sequence
<220> FEATURE:
<223> OTHER INFORMATION: DNA probe

<400> SEQUENCE: 136
```

-continued cctcggggc gaagtagcgg caccc                                    25

<210> SEQ ID NO 137
<211> LENGTH: 25
<212> TYPE: DNA
<213> ORGANISM: Artificial Sequence
<220> FEATURE:
<223> OTHER INFORMATION: DNA probe

<400> SEQUENCE: 137
cctcggggcg aagtagcggc acccg                                   25

<210> SEQ ID NO 138
<211> LENGTH: 25
<212> TYPE: DNA
<213> ORGANISM: Artificial Sequence
<220> FEATURE:
<223> OTHER INFORMATION: DNA probe

<400> SEQUENCE: 138
ctcggggcga agtagcggca cccga                                   25

<210> SEQ ID NO 139
<211> LENGTH: 25
<212> TYPE: DNA
<213> ORGANISM: Artificial Sequence
<220> FEATURE:
<223> OTHER INFORMATION: DNA probe

<400> SEQUENCE: 139
tcggggcgaa gtagcggcac ccgat                                   25

<210> SEQ ID NO 140
<211> LENGTH: 25
<212> TYPE: DNA
<213> ORGANISM: Artificial Sequence
<220> FEATURE:
<223> OTHER INFORMATION: DNA probe

<400> SEQUENCE: 140
cggggcgaag tagcggcacc cgatg                                   25

<210> SEQ ID NO 141
<211> LENGTH: 25
<212> TYPE: DNA
<213> ORGANISM: Artificial Sequence
<220> FEATURE:
<223> OTHER INFORMATION: DNA probe

<400> SEQUENCE: 141
ggggcgaagt agcggcaccc gatgc                                   25

<210> SEQ ID NO 142
<211> LENGTH: 25
<212> TYPE: DNA
<213> ORGANISM: Artificial Sequence
<220> FEATURE:
<223> OTHER INFORMATION: DNA probe

<400> SEQUENCE: 142
gggcgaagta gcggcacccg atgca                                   25

<210> SEQ ID NO 143
<211> LENGTH: 25
<212> TYPE: DNA
<213> ORGANISM: Artificial Sequence
<220> FEATURE:

<223> OTHER INFORMATION: DNA probe

<400> SEQUENCE: 143
ggcgaagtag cggcacccga tgcac        25

<210> SEQ ID NO 144
<211> LENGTH: 25
<212> TYPE: DNA
<213> ORGANISM: Artificial Sequence
<220> FEATURE:
<223> OTHER INFORMATION: DNA probe

<400> SEQUENCE: 144
gcgaagtagc ggcacccgat gcacc        25

<210> SEQ ID NO 145
<211> LENGTH: 25
<212> TYPE: DNA
<213> ORGANISM: Artificial Sequence
<220> FEATURE:
<223> OTHER INFORMATION: DNA probe

<400> SEQUENCE: 145
cgaagtagcg gcacccgatg cacct        25

<210> SEQ ID NO 146
<211> LENGTH: 25
<212> TYPE: DNA
<213> ORGANISM: Artificial Sequence
<220> FEATURE:
<223> OTHER INFORMATION: DNA probe

<400> SEQUENCE: 146
gaagtagcgg cacccgatgc acctg        25

<210> SEQ ID NO 147
<211> LENGTH: 25
<212> TYPE: DNA
<213> ORGANISM: Artificial Sequence
<220> FEATURE:
<223> OTHER INFORMATION: DNA probe

<400> SEQUENCE: 147
aagtagcggc acccgatgca cctgc        25

<210> SEQ ID NO 148
<211> LENGTH: 25
<212> TYPE: DNA
<213> ORGANISM: Artificial Sequence
<220> FEATURE:
<223> OTHER INFORMATION: DNA probe

<400> SEQUENCE: 148
agtagcggca cccgatgcac ctgct        25

<210> SEQ ID NO 149
<211> LENGTH: 25
<212> TYPE: DNA
<213> ORGANISM: Artificial Sequence
<220> FEATURE:
<223> OTHER INFORMATION: DNA probe

<400> SEQUENCE: 149
gtagcggcac ccgatgcacc tgctg        25

<210> SEQ ID NO 150

```
<211> LENGTH: 25
<212> TYPE: DNA
<213> ORGANISM: Artificial Sequence
<220> FEATURE:
<223> OTHER INFORMATION: DNA probe

<400> SEQUENCE: 150
tagcggcacc cgatgcacct gctgt                                           25

<210> SEQ ID NO 151
<211> LENGTH: 25
<212> TYPE: DNA
<213> ORGANISM: Artificial Sequence
<220> FEATURE:
<223> OTHER INFORMATION: DNA probe

<400> SEQUENCE: 151
agcggcaccc gatgcacctg ctgtg                                           25

<210> SEQ ID NO 152
<211> LENGTH: 25
<212> TYPE: DNA
<213> ORGANISM: Artificial Sequence
<220> FEATURE:
<223> OTHER INFORMATION: DNA probe

<400> SEQUENCE: 152
gcggcacccg atgcacctgc tgtgc                                           25

<210> SEQ ID NO 153
<211> LENGTH: 25
<212> TYPE: DNA
<213> ORGANISM: Artificial Sequence
<220> FEATURE:
<223> OTHER INFORMATION: DNA probe

<400> SEQUENCE: 153
cggcacccga tgcacctgct gtgcg                                           25

<210> SEQ ID NO 154
<211> LENGTH: 25
<212> TYPE: DNA
<213> ORGANISM: Artificial Sequence
<220> FEATURE:
<223> OTHER INFORMATION: DNA probe

<400> SEQUENCE: 154
ggcacccgat gcacctgctg tgcgt                                           25

<210> SEQ ID NO 155
<211> LENGTH: 25
<212> TYPE: DNA
<213> ORGANISM: Artificial Sequence
<220> FEATURE:
<223> OTHER INFORMATION: DNA probe

<400> SEQUENCE: 155
gcacccgatg cacctgctgt gcgtc                                           25

<210> SEQ ID NO 156
<211> LENGTH: 25
<212> TYPE: DNA
<213> ORGANISM: Artificial Sequence
<220> FEATURE:
<223> OTHER INFORMATION: DNA probe

<400> SEQUENCE: 156
```
cacccgatgc acctgctgtg cgtca                                          25

<210> SEQ ID NO 157
<211> LENGTH: 25
<212> TYPE: DNA
<213> ORGANISM: Artificial Sequence
<220> FEATURE:
<223> OTHER INFORMATION: DNA probe

<400> SEQUENCE: 157
acccgatgca cctgctgtgc gtcaa                                          25

<210> SEQ ID NO 158
<211> LENGTH: 25
<212> TYPE: DNA
<213> ORGANISM: Artificial Sequence
<220> FEATURE:
<223> OTHER INFORMATION: DNA probe

<400> SEQUENCE: 158
cccgatgcac ctgctgtgcg tcaag                                          25

<210> SEQ ID NO 159
<211> LENGTH: 25
<212> TYPE: DNA
<213> ORGANISM: Artificial Sequence
<220> FEATURE:
<223> OTHER INFORMATION: DNA probe

<400> SEQUENCE: 159
ccgatgcacc tgctgtgcgt caagc                                          25

<210> SEQ ID NO 160
<211> LENGTH: 25
<212> TYPE: DNA
<213> ORGANISM: Artificial Sequence
<220> FEATURE:
<223> OTHER INFORMATION: DNA probe

<400> SEQUENCE: 160
cgatgcacct gctgtgcgtc aagca                                          25

<210> SEQ ID NO 161
<211> LENGTH: 25
<212> TYPE: DNA
<213> ORGANISM: Artificial Sequence
<220> FEATURE:
<223> OTHER INFORMATION: DNA probe

<400> SEQUENCE: 161
gatgcacctg ctgtgcgtca agcac                                          25

<210> SEQ ID NO 162
<211> LENGTH: 25
<212> TYPE: DNA
<213> ORGANISM: Artificial Sequence
<220> FEATURE:
<223> OTHER INFORMATION: DNA probe

<400> SEQUENCE: 162
atgcacctgc tgtgcgtcaa gcacg                                          25

<210> SEQ ID NO 163
<211> LENGTH: 25
<212> TYPE: DNA
<213> ORGANISM: Artificial Sequence
<220> FEATURE:

```
<223> OTHER INFORMATION: DNA probe

<400> SEQUENCE: 163
tgcacctgct gtgcgtcaag cacgc                                          25

<210> SEQ ID NO 164
<211> LENGTH: 25
<212> TYPE: DNA
<213> ORGANISM: Artificial Sequence
<220> FEATURE:
<223> OTHER INFORMATION: DNA probe

<400> SEQUENCE: 164
gcacctgctg tgcgtcaagc acgcc                                          25

<210> SEQ ID NO 165
<211> LENGTH: 25
<212> TYPE: DNA
<213> ORGANISM: Artificial Sequence
<220> FEATURE:
<223> OTHER INFORMATION: DNA probe

<400> SEQUENCE: 165
cacctgctgt gcgtcaagca cgcca                                          25

<210> SEQ ID NO 166
<211> LENGTH: 25
<212> TYPE: DNA
<213> ORGANISM: Artificial Sequence
<220> FEATURE:
<223> OTHER INFORMATION: DNA probe

<400> SEQUENCE: 166
acctgctgtg cgtcaagcac gccaa                                          25

<210> SEQ ID NO 167
<211> LENGTH: 25
<212> TYPE: DNA
<213> ORGANISM: Artificial Sequence
<220> FEATURE:
<223> OTHER INFORMATION: DNA probe

<400> SEQUENCE: 167
cctgctgtgc gtcaagcacg ccaag                                          25

<210> SEQ ID NO 168
<211> LENGTH: 25
<212> TYPE: DNA
<213> ORGANISM: Artificial Sequence
<220> FEATURE:
<223> OTHER INFORMATION: DNA probe

<400> SEQUENCE: 168
ctgctgtgcg tcaagcacgc caagc                                          25

<210> SEQ ID NO 169
<211> LENGTH: 25
<212> TYPE: DNA
<213> ORGANISM: Artificial Sequence
<220> FEATURE:
<223> OTHER INFORMATION: DNA probe

<400> SEQUENCE: 169
tgctgtgcgt caagcacgcc aagct                                          25

<210> SEQ ID NO 170
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 170
gctgtgcgtc aagcacgcca agctg                                              25

<210> SEQ ID NO 171
<211> LENGTH: 25
<212> TYPE: DNA
<213> ORGANISM: Artificial Sequence
<220> FEATURE:
<223> OTHER INFORMATION: DNA probe

<400> SEQUENCE: 171
ctgtgcgtca agcacgccaa gctgt                                              25

<210> SEQ ID NO 172
<211> LENGTH: 25
<212> TYPE: DNA
<213> ORGANISM: Artificial Sequence
<220> FEATURE:
<223> OTHER INFORMATION: DNA probe

<400> SEQUENCE: 172
tgtgcgtcaa gcacgccaag ctgtc                                              25

<210> SEQ ID NO 173
<211> LENGTH: 25
<212> TYPE: DNA
<213> ORGANISM: Artificial Sequence
<220> FEATURE:
<223> OTHER INFORMATION: DNA probe

<400> SEQUENCE: 173
gtgcgtcaag cacgccaagc tgtcg                                              25

<210> SEQ ID NO 174
<211> LENGTH: 25
<212> TYPE: DNA
<213> ORGANISM: Artificial Sequence
<220> FEATURE:
<223> OTHER INFORMATION: DNA probe

<400> SEQUENCE: 174
tgcgtcaagc acgccaagct gtcgc                                              25

<210> SEQ ID NO 175
<211> LENGTH: 25
<212> TYPE: DNA
<213> ORGANISM: Artificial Sequence
<220> FEATURE:
<223> OTHER INFORMATION: DNA probe

<400> SEQUENCE: 175
gcgtcaagca cgccaagctg tcgct                                              25

<210> SEQ ID NO 176
<211> LENGTH: 25
<212> TYPE: DNA
<213> ORGANISM: Artificial Sequence
<220> FEATURE:
<223> OTHER INFORMATION: DNA probe

<400> SEQUENCE: 176
```

```
cgtcaagcac gccaagctgt cgctg                                              25

<210> SEQ ID NO 177
<211> LENGTH: 25
<212> TYPE: DNA
<213> ORGANISM: Artificial Sequence
<220> FEATURE:
<223> OTHER INFORMATION: DNA probe

<400> SEQUENCE: 177
gtcaagcacg ccaagctgtc gctgc                                              25

<210> SEQ ID NO 178
<211> LENGTH: 25
<212> TYPE: DNA
<213> ORGANISM: Artificial Sequence
<220> FEATURE:
<223> OTHER INFORMATION: DNA probe

<400> SEQUENCE: 178
tcaagcacgc caagctgtcg ctgcg                                              25

<210> SEQ ID NO 179
<211> LENGTH: 25
<212> TYPE: DNA
<213> ORGANISM: Artificial Sequence
<220> FEATURE:
<223> OTHER INFORMATION: DNA probe

<400> SEQUENCE: 179
caagcacgcc aagctgtcgc tgcgg                                              25

<210> SEQ ID NO 180
<211> LENGTH: 25
<212> TYPE: DNA
<213> ORGANISM: Artificial Sequence
<220> FEATURE:
<223> OTHER INFORMATION: DNA probe

<400> SEQUENCE: 180
aagcacgcca agctgtcgct gcggc                                              25

<210> SEQ ID NO 181
<211> LENGTH: 25
<212> TYPE: DNA
<213> ORGANISM: Artificial Sequence
<220> FEATURE:
<223> OTHER INFORMATION: DNA probe

<400> SEQUENCE: 181
agcacgccaa gctgtcgctg cggcg                                              25

<210> SEQ ID NO 182
<211> LENGTH: 25
<212> TYPE: DNA
<213> ORGANISM: Artificial Sequence
<220> FEATURE:
<223> OTHER INFORMATION: DNA probe

<400> SEQUENCE: 182
gcacgccaag ctgtcgctgc ggcgc                                              25

<210> SEQ ID NO 183
<211> LENGTH: 25
<212> TYPE: DNA
<213> ORGANISM: Artificial Sequence
<220> FEATURE:
```

<223> OTHER INFORMATION: DNA probe

<400> SEQUENCE: 183
cacgccaagc tgtcgctgcg gcgct                                              25

<210> SEQ ID NO 184
<211> LENGTH: 25
<212> TYPE: DNA
<213> ORGANISM: Artificial Sequence
<220> FEATURE:
<223> OTHER INFORMATION: DNA probe

<400> SEQUENCE: 184
acgccaagct gtcgctgcgg cgctc                                              25

<210> SEQ ID NO 185
<211> LENGTH: 25
<212> TYPE: DNA
<213> ORGANISM: Artificial Sequence
<220> FEATURE:
<223> OTHER INFORMATION: DNA probe

<400> SEQUENCE: 185
cgccaagctg tcgctgcggc gctcg                                              25

<210> SEQ ID NO 186
<211> LENGTH: 25
<212> TYPE: DNA
<213> ORGANISM: Artificial Sequence
<220> FEATURE:
<223> OTHER INFORMATION: DNA probe

<400> SEQUENCE: 186
gccaagctgt cgctgcggcg ctcgg                                              25

<210> SEQ ID NO 187
<211> LENGTH: 25
<212> TYPE: DNA
<213> ORGANISM: Artificial Sequence
<220> FEATURE:
<223> OTHER INFORMATION: DNA probe

<400> SEQUENCE: 187
ccaagctgtc gctgcggcgc tcggt                                              25

<210> SEQ ID NO 188
<211> LENGTH: 25
<212> TYPE: DNA
<213> ORGANISM: Artificial Sequence
<220> FEATURE:
<223> OTHER INFORMATION: DNA probe

<400> SEQUENCE: 188
caagctgtcg ctgcggcgct cggtc                                              25

<210> SEQ ID NO 189
<211> LENGTH: 25
<212> TYPE: DNA
<213> ORGANISM: Artificial Sequence
<220> FEATURE:
<223> OTHER INFORMATION: DNA probe

<400> SEQUENCE: 189
aagctgtcgc tgcggcgctc ggtct                                              25

<210> SEQ ID NO 190

<211> LENGTH: 25
<212> TYPE: DNA
<213> ORGANISM: Artificial Sequence
<220> FEATURE:
<223> OTHER INFORMATION: DNA probe

<400> SEQUENCE: 190
agctgtcgct gcggcgctcg gtctc                                        25

<210> SEQ ID NO 191
<211> LENGTH: 25
<212> TYPE: DNA
<213> ORGANISM: Artificial Sequence
<220> FEATURE:
<223> OTHER INFORMATION: DNA probe

<400> SEQUENCE: 191
gctgtcgctg cggcgctcgg tctcc                                        25

<210> SEQ ID NO 192
<211> LENGTH: 25
<212> TYPE: DNA
<213> ORGANISM: Artificial Sequence
<220> FEATURE:
<223> OTHER INFORMATION: DNA probe

<400> SEQUENCE: 192
ctgtcgctgc ggcgctcggt ctcct                                        25

<210> SEQ ID NO 193
<211> LENGTH: 25
<212> TYPE: DNA
<213> ORGANISM: Artificial Sequence
<220> FEATURE:
<223> OTHER INFORMATION: DNA probe

<400> SEQUENCE: 193
tgtcgctgcg gcgctcggtc tccta                                        25

<210> SEQ ID NO 194
<211> LENGTH: 25
<212> TYPE: DNA
<213> ORGANISM: Artificial Sequence
<220> FEATURE:
<223> OTHER INFORMATION: DNA probe

<400> SEQUENCE: 194
gtcgctgcgg cgctcggtct cctac                                        25

<210> SEQ ID NO 195
<211> LENGTH: 25
<212> TYPE: DNA
<213> ORGANISM: Artificial Sequence
<220> FEATURE:
<223> OTHER INFORMATION: DNA probe

<400> SEQUENCE: 195
tcgctgcggc gctcggtctc ctacc                                        25

<210> SEQ ID NO 196
<211> LENGTH: 25
<212> TYPE: DNA
<213> ORGANISM: Artificial Sequence
<220> FEATURE:
<223> OTHER INFORMATION: DNA probe

<400> SEQUENCE: 196
cgctgcggcg ctcggtctcc tacct                                              25

<210> SEQ ID NO 197
<211> LENGTH: 25
<212> TYPE: DNA
<213> ORGANISM: Artificial Sequence
<220> FEATURE:
<223> OTHER INFORMATION: DNA probe

<400> SEQUENCE: 197
gctgcggcgc tcggtctcct acctc                                              25

<210> SEQ ID NO 198
<211> LENGTH: 25
<212> TYPE: DNA
<213> ORGANISM: Artificial Sequence
<220> FEATURE:
<223> OTHER INFORMATION: DNA probe

<400> SEQUENCE: 198
ctgcggcgct cggtctccta cctcg                                              25

<210> SEQ ID NO 199
<211> LENGTH: 25
<212> TYPE: DNA
<213> ORGANISM: Artificial Sequence
<220> FEATURE:
<223> OTHER INFORMATION: DNA probe

<400> SEQUENCE: 199
tgcggcgctc ggtctcctac ctcgg                                              25

<210> SEQ ID NO 200
<211> LENGTH: 25
<212> TYPE: DNA
<213> ORGANISM: Artificial Sequence
<220> FEATURE:
<223> OTHER INFORMATION: DNA probe

<400> SEQUENCE: 200
gcggcgctcg gtctcctacc tcggc                                              25

<210> SEQ ID NO 201
<211> LENGTH: 25
<212> TYPE: DNA
<213> ORGANISM: Artificial Sequence
<220> FEATURE:
<223> OTHER INFORMATION: DNA probe

<400> SEQUENCE: 201
cggcgctcgg tctcctacct cggcg                                              25

<210> SEQ ID NO 202
<211> LENGTH: 25
<212> TYPE: DNA
<213> ORGANISM: Artificial Sequence
<220> FEATURE:
<223> OTHER INFORMATION: DNA probe

<400> SEQUENCE: 202
ggcgctcggt ctcctacctc ggcgc                                              25

<210> SEQ ID NO 203
<211> LENGTH: 25
<212> TYPE: DNA
<213> ORGANISM: Artificial Sequence
<220> FEATURE:

```
<223> OTHER INFORMATION: DNA probe

<400> SEQUENCE: 203
gcgctcggtc tcctacctcg gcgcc                                              25

<210> SEQ ID NO 204
<211> LENGTH: 25
<212> TYPE: DNA
<213> ORGANISM: Artificial Sequence
<220> FEATURE:
<223> OTHER INFORMATION: DNA probe

<400> SEQUENCE: 204
cgctcggtct cctacctcgg cgccc                                              25

<210> SEQ ID NO 205
<211> LENGTH: 25
<212> TYPE: DNA
<213> ORGANISM: Artificial Sequence
<220> FEATURE:
<223> OTHER INFORMATION: DNA probe

<400> SEQUENCE: 205
gctcggtctc ctacctcggc gcccg                                              25

<210> SEQ ID NO 206
<211> LENGTH: 25
<212> TYPE: DNA
<213> ORGANISM: Artificial Sequence
<220> FEATURE:
<223> OTHER INFORMATION: DNA probe

<400> SEQUENCE: 206
ctcggtctcc tacctcggcg cccgc                                              25

<210> SEQ ID NO 207
<211> LENGTH: 25
<212> TYPE: DNA
<213> ORGANISM: Artificial Sequence
<220> FEATURE:
<223> OTHER INFORMATION: DNA probe

<400> SEQUENCE: 207
tcggtctcct acctcggcgc ccgcg                                              25

<210> SEQ ID NO 208
<211> LENGTH: 25
<212> TYPE: DNA
<213> ORGANISM: Artificial Sequence
<220> FEATURE:
<223> OTHER INFORMATION: DNA probe

<400> SEQUENCE: 208
cggtctccta cctcggcgcc cgcgg                                              25

<210> SEQ ID NO 209
<211> LENGTH: 25
<212> TYPE: DNA
<213> ORGANISM: Artificial Sequence
<220> FEATURE:
<223> OTHER INFORMATION: DNA probe

<400> SEQUENCE: 209
ggtctcctac ctcggcgccc gcggc                                              25

<210> SEQ ID NO 210
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 210
gtctcctacc tcggcgcccg cggca                                     25

<210> SEQ ID NO 211
<211> LENGTH: 25
<212> TYPE: DNA
<213> ORGANISM: Artificial Sequence
<220> FEATURE:
<223> OTHER INFORMATION: DNA probe

<400> SEQUENCE: 211
tctcctacct cggcgcccgc ggcac                                     25

<210> SEQ ID NO 212
<211> LENGTH: 25
<212> TYPE: DNA
<213> ORGANISM: Artificial Sequence
<220> FEATURE:
<223> OTHER INFORMATION: DNA probe

<400> SEQUENCE: 212
ctcctacctc ggcgcccgcg gcacc                                     25

<210> SEQ ID NO 213
<211> LENGTH: 25
<212> TYPE: DNA
<213> ORGANISM: Artificial Sequence
<220> FEATURE:
<223> OTHER INFORMATION: DNA probe

<400> SEQUENCE: 213
tcctacctcg gcgcccgcgg cacct                                     25

<210> SEQ ID NO 214
<211> LENGTH: 25
<212> TYPE: DNA
<213> ORGANISM: Artificial Sequence
<220> FEATURE:
<223> OTHER INFORMATION: DNA probe

<400> SEQUENCE: 214
cctacctcgg cgcccgcggc accta                                     25

<210> SEQ ID NO 215
<211> LENGTH: 25
<212> TYPE: DNA
<213> ORGANISM: Artificial Sequence
<220> FEATURE:
<223> OTHER INFORMATION: DNA probe

<400> SEQUENCE: 215
ctacctcggc gcccgcggca cctat                                     25

<210> SEQ ID NO 216
<211> LENGTH: 25
<212> TYPE: DNA
<213> ORGANISM: Artificial Sequence
<220> FEATURE:
<223> OTHER INFORMATION: DNA probe

<400> SEQUENCE: 216
```
tacctcggcg cccgcggcac ctatc                                      25

<210> SEQ ID NO 217
<211> LENGTH: 25
<212> TYPE: DNA
<213> ORGANISM: Artificial Sequence
<220> FEATURE:
<223> OTHER INFORMATION: DNA probe

<400> SEQUENCE: 217
acctcggcgc ccgcggcacc tatct                                      25

<210> SEQ ID NO 218
<211> LENGTH: 25
<212> TYPE: DNA
<213> ORGANISM: Artificial Sequence
<220> FEATURE:
<223> OTHER INFORMATION: DNA probe

<400> SEQUENCE: 218
cctcggcgcc cgcggcacct atctc                                      25

<210> SEQ ID NO 219
<211> LENGTH: 25
<212> TYPE: DNA
<213> ORGANISM: Artificial Sequence
<220> FEATURE:
<223> OTHER INFORMATION: DNA probe

<400> SEQUENCE: 219
ctcggcgccc gcggcaccta tctcg                                      25

<210> SEQ ID NO 220
<211> LENGTH: 25
<212> TYPE: DNA
<213> ORGANISM: Artificial Sequence
<220> FEATURE:
<223> OTHER INFORMATION: DNA probe

<400> SEQUENCE: 220
tcggcgcccg cggcacctat ctcgt                                      25

<210> SEQ ID NO 221
<211> LENGTH: 25
<212> TYPE: DNA
<213> ORGANISM: Artificial Sequence
<220> FEATURE:
<223> OTHER INFORMATION: DNA probe

<400> SEQUENCE: 221
cggcgcccgc ggcacctatc tcgtc                                      25

<210> SEQ ID NO 222
<211> LENGTH: 25
<212> TYPE: DNA
<213> ORGANISM: Artificial Sequence
<220> FEATURE:
<223> OTHER INFORMATION: DNA probe

<400> SEQUENCE: 222
ggcgcccgcg gcacctatct cgtcc                                      25

<210> SEQ ID NO 223
<211> LENGTH: 25
<212> TYPE: DNA
<213> ORGANISM: Artificial Sequence
<220> FEATURE:

<223> OTHER INFORMATION: DNA probe

<400> SEQUENCE: 223
gcgcccgcgg cacctatctc gtcct                25

<210> SEQ ID NO 224
<211> LENGTH: 25
<212> TYPE: DNA
<213> ORGANISM: Artificial Sequence
<220> FEATURE:
<223> OTHER INFORMATION: DNA probe

<400> SEQUENCE: 224
cgcccgcggc acctatctcg tcctc                25

<210> SEQ ID NO 225
<211> LENGTH: 25
<212> TYPE: DNA
<213> ORGANISM: Artificial Sequence
<220> FEATURE:
<223> OTHER INFORMATION: DNA probe

<400> SEQUENCE: 225
gcccgcggca cctatctcgt cctcc                25

<210> SEQ ID NO 226
<211> LENGTH: 25
<212> TYPE: DNA
<213> ORGANISM: Artificial Sequence
<220> FEATURE:
<223> OTHER INFORMATION: DNA probe

<400> SEQUENCE: 226
cccgcggcac ctatctcgtc ctccc                25

<210> SEQ ID NO 227
<211> LENGTH: 25
<212> TYPE: DNA
<213> ORGANISM: Artificial Sequence
<220> FEATURE:
<223> OTHER INFORMATION: DNA probe

<400> SEQUENCE: 227
ccgcggcacc tatctcgtcc tccca                25

<210> SEQ ID NO 228
<211> LENGTH: 25
<212> TYPE: DNA
<213> ORGANISM: Artificial Sequence
<220> FEATURE:
<223> OTHER INFORMATION: DNA probe

<400> SEQUENCE: 228
cgcggcacct atctcgtcct cccag                25

<210> SEQ ID NO 229
<211> LENGTH: 25
<212> TYPE: DNA
<213> ORGANISM: Artificial Sequence
<220> FEATURE:
<223> OTHER INFORMATION: DNA probe

<400> SEQUENCE: 229
gcggcaccta tctcgtcctc ccagg                25

<210> SEQ ID NO 230

```
<211> LENGTH: 25
<212> TYPE: DNA
<213> ORGANISM: Artificial Sequence
<220> FEATURE:
<223> OTHER INFORMATION: DNA probe

<400> SEQUENCE: 230
cggcacctat ctcgtcctcc caggc                                         25

<210> SEQ ID NO 231
<211> LENGTH: 25
<212> TYPE: DNA
<213> ORGANISM: Artificial Sequence
<220> FEATURE:
<223> OTHER INFORMATION: DNA probe

<400> SEQUENCE: 231
ggcacctatc tcgtcctccc aggcc                                         25

<210> SEQ ID NO 232
<211> LENGTH: 25
<212> TYPE: DNA
<213> ORGANISM: Artificial Sequence
<220> FEATURE:
<223> OTHER INFORMATION: DNA probe

<400> SEQUENCE: 232
gcacctatct cgtcctccca ggcct                                         25

<210> SEQ ID NO 233
<211> LENGTH: 25
<212> TYPE: DNA
<213> ORGANISM: Artificial Sequence
<220> FEATURE:
<223> OTHER INFORMATION: DNA probe

<400> SEQUENCE: 233
cacctatctc gtcctcccag gcctc                                         25

<210> SEQ ID NO 234
<211> LENGTH: 25
<212> TYPE: DNA
<213> ORGANISM: Artificial Sequence
<220> FEATURE:
<223> OTHER INFORMATION: DNA probe

<400> SEQUENCE: 234
acctatctcg tcctcccagg cctca                                         25

<210> SEQ ID NO 235
<211> LENGTH: 25
<212> TYPE: DNA
<213> ORGANISM: Artificial Sequence
<220> FEATURE:
<223> OTHER INFORMATION: DNA probe

<400> SEQUENCE: 235
cctatctcgt cctcccaggc ctcat                                         25

<210> SEQ ID NO 236
<211> LENGTH: 25
<212> TYPE: DNA
<213> ORGANISM: Artificial Sequence
<220> FEATURE:
<223> OTHER INFORMATION: DNA probe

<400> SEQUENCE: 236
```
ctatctcgtc ctcccaggcc tcata    25

<210> SEQ ID NO 237
<211> LENGTH: 25
<212> TYPE: DNA
<213> ORGANISM: Artificial Sequence
<220> FEATURE:
<223> OTHER INFORMATION: DNA probe

<400> SEQUENCE: 237
tatctcgtcc tcccaggcct cataa    25

<210> SEQ ID NO 238
<211> LENGTH: 25
<212> TYPE: DNA
<213> ORGANISM: Artificial Sequence
<220> FEATURE:
<223> OTHER INFORMATION: DNA probe

<400> SEQUENCE: 238
atctcgtcct cccaggcctc ataac    25

<210> SEQ ID NO 239
<211> LENGTH: 25
<212> TYPE: DNA
<213> ORGANISM: Artificial Sequence
<220> FEATURE:
<223> OTHER INFORMATION: DNA probe

<400> SEQUENCE: 239
tctcgtcctc ccaggcctca taacc    25

<210> SEQ ID NO 240
<211> LENGTH: 25
<212> TYPE: DNA
<213> ORGANISM: Artificial Sequence
<220> FEATURE:
<223> OTHER INFORMATION: DNA probe

<400> SEQUENCE: 240
ctcgtcctcc caggcctcat aaccc    25

<210> SEQ ID NO 241
<211> LENGTH: 25
<212> TYPE: DNA
<213> ORGANISM: Artificial Sequence
<220> FEATURE:
<223> OTHER INFORMATION: DNA probe

<400> SEQUENCE: 241
tcgtcctccc aggcctcata accct    25

<210> SEQ ID NO 242
<211> LENGTH: 25
<212> TYPE: DNA
<213> ORGANISM: Artificial Sequence
<220> FEATURE:
<223> OTHER INFORMATION: DNA probe

<400> SEQUENCE: 242
cgtcctccca ggcctcataa ccctg    25

<210> SEQ ID NO 243
<211> LENGTH: 25
<212> TYPE: DNA
<213> ORGANISM: Artificial Sequence
<220> FEATURE:

```
<223> OTHER INFORMATION: DNA probe

<400> SEQUENCE: 243
gtcctcccag gcctcataac cctgc                                              25

<210> SEQ ID NO 244
<211> LENGTH: 25
<212> TYPE: DNA
<213> ORGANISM: Artificial Sequence
<220> FEATURE:
<223> OTHER INFORMATION: DNA probe

<400> SEQUENCE: 244
tcctcccagg cctcataacc ctgcc                                              25

<210> SEQ ID NO 245
<211> LENGTH: 25
<212> TYPE: DNA
<213> ORGANISM: Artificial Sequence
<220> FEATURE:
<223> OTHER INFORMATION: DNA probe

<400> SEQUENCE: 245
cctcccaggc ctcataaccc tgccc                                              25

<210> SEQ ID NO 246
<211> LENGTH: 25
<212> TYPE: DNA
<213> ORGANISM: Artificial Sequence
<220> FEATURE:
<223> OTHER INFORMATION: DNA probe

<400> SEQUENCE: 246
ctcccaggcc tcataaccct gcccc                                              25

<210> SEQ ID NO 247
<211> LENGTH: 25
<212> TYPE: DNA
<213> ORGANISM: Artificial Sequence
<220> FEATURE:
<223> OTHER INFORMATION: DNA probe

<400> SEQUENCE: 247
tcccaggcct cataaccctg cccct                                              25

<210> SEQ ID NO 248
<211> LENGTH: 25
<212> TYPE: DNA
<213> ORGANISM: Artificial Sequence
<220> FEATURE:
<223> OTHER INFORMATION: DNA probe

<400> SEQUENCE: 248
cccaggcctc ataaccctgc ccctc                                              25

<210> SEQ ID NO 249
<211> LENGTH: 25
<212> TYPE: DNA
<213> ORGANISM: Artificial Sequence
<220> FEATURE:
<223> OTHER INFORMATION: DNA probe

<400> SEQUENCE: 249
ccaggcctca taaccctgcc cctct                                              25

<210> SEQ ID NO 250
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 250
caggcctcat aaccctgccc ctctg                                              25

<210> SEQ ID NO 251
<211> LENGTH: 25
<212> TYPE: DNA
<213> ORGANISM: Artificial Sequence
<220> FEATURE:
<223> OTHER INFORMATION: DNA probe

<400> SEQUENCE: 251
aggcctcata accctgcccc tctgt                                              25

<210> SEQ ID NO 252
<211> LENGTH: 25
<212> TYPE: DNA
<213> ORGANISM: Artificial Sequence
<220> FEATURE:
<223> OTHER INFORMATION: DNA probe

<400> SEQUENCE: 252
ggcctcataa ccctgcccct ctgtg                                              25

<210> SEQ ID NO 253
<211> LENGTH: 25
<212> TYPE: DNA
<213> ORGANISM: Artificial Sequence
<220> FEATURE:
<223> OTHER INFORMATION: DNA probe

<400> SEQUENCE: 253
gcctcataac cctgcccctc tgtgc                                              25

<210> SEQ ID NO 254
<211> LENGTH: 25
<212> TYPE: DNA
<213> ORGANISM: Artificial Sequence
<220> FEATURE:
<223> OTHER INFORMATION: DNA probe

<400> SEQUENCE: 254
cctcataacc ctgcccctct gtgcc                                              25

<210> SEQ ID NO 255
<211> LENGTH: 25
<212> TYPE: DNA
<213> ORGANISM: Artificial Sequence
<220> FEATURE:
<223> OTHER INFORMATION: DNA probe

<400> SEQUENCE: 255
ctcataaccc tgcccctctg tgcct                                              25

<210> SEQ ID NO 256
<211> LENGTH: 25
<212> TYPE: DNA
<213> ORGANISM: Artificial Sequence
<220> FEATURE:
<223> OTHER INFORMATION: DNA probe

<400> SEQUENCE: 256
```
tcataaccct gccctctgt gcctt                                              25

<210> SEQ ID NO 257
<211> LENGTH: 25
<212> TYPE: DNA
<213> ORGANISM: Artificial Sequence
<220> FEATURE:
<223> OTHER INFORMATION: DNA probe

<400> SEQUENCE: 257
cataaccctg ccctctgtg cctt                                               25

<210> SEQ ID NO 258
<211> LENGTH: 25
<212> TYPE: DNA
<213> ORGANISM: Artificial Sequence
<220> FEATURE:
<223> OTHER INFORMATION: DNA probe

<400> SEQUENCE: 258
ataaccctgc ccctctgtgc ctttc                                             25

<210> SEQ ID NO 259
<211> LENGTH: 25
<212> TYPE: DNA
<213> ORGANISM: Artificial Sequence
<220> FEATURE:
<223> OTHER INFORMATION: DNA probe

<400> SEQUENCE: 259
taaccctgcc cctctgtgcc tttca                                             25

<210> SEQ ID NO 260
<211> LENGTH: 25
<212> TYPE: DNA
<213> ORGANISM: Artificial Sequence
<220> FEATURE:
<223> OTHER INFORMATION: DNA probe

<400> SEQUENCE: 260
aaccctgccc ctctgtgcct ttcac                                             25

<210> SEQ ID NO 261
<211> LENGTH: 25
<212> TYPE: DNA
<213> ORGANISM: Artificial Sequence
<220> FEATURE:
<223> OTHER INFORMATION: DNA probe

<400> SEQUENCE: 261
accctgcccc tctgtgcctt tcact                                             25

<210> SEQ ID NO 262
<211> LENGTH: 25
<212> TYPE: DNA
<213> ORGANISM: Artificial Sequence
<220> FEATURE:
<223> OTHER INFORMATION: DNA probe

<400> SEQUENCE: 262 ccctgccct ctgtgccttt cactt                                              25

<210> SEQ ID NO 263
<211> LENGTH: 25
<212> TYPE: DNA
<213> ORGANISM: Artificial Sequence
<220> FEATURE:

<223> OTHER INFORMATION: DNA probe

<400> SEQUENCE: 263
cctgcccctc tgtgcctttc acttc                                    25

<210> SEQ ID NO 264
<211> LENGTH: 25
<212> TYPE: DNA
<213> ORGANISM: Artificial Sequence
<220> FEATURE:
<223> OTHER INFORMATION: DNA probe

<400> SEQUENCE: 264
ctgcccctct gtgcctttca cttcc                                    25

<210> SEQ ID NO 265
<211> LENGTH: 25
<212> TYPE: DNA
<213> ORGANISM: Artificial Sequence
<220> FEATURE:
<223> OTHER INFORMATION: DNA probe

<400> SEQUENCE: 265
tgcccctctg tgcctttcac ttccg                                    25

<210> SEQ ID NO 266
<211> LENGTH: 25
<212> TYPE: DNA
<213> ORGANISM: Artificial Sequence
<220> FEATURE:
<223> OTHER INFORMATION: DNA probe

<400> SEQUENCE: 266
gcccctctgt gcctttcact tccgg                                    25

<210> SEQ ID NO 267
<211> LENGTH: 25
<212> TYPE: DNA
<213> ORGANISM: Artificial Sequence
<220> FEATURE:
<223> OTHER INFORMATION: DNA probe

<400> SEQUENCE: 267
cccctctgtg cctttcactt ccggg                                    25

<210> SEQ ID NO 268
<211> LENGTH: 25
<212> TYPE: DNA
<213> ORGANISM: Artificial Sequence
<220> FEATURE:
<223> OTHER INFORMATION: DNA probe

<400> SEQUENCE: 268
ccctctgtgc ctttcacttc cgggt                                    25

<210> SEQ ID NO 269
<211> LENGTH: 25
<212> TYPE: DNA
<213> ORGANISM: Artificial Sequence
<220> FEATURE:
<223> OTHER INFORMATION: DNA probe

<400> SEQUENCE: 269
cctctgtgcc tttcacttcc gggtg                                    25

<210> SEQ ID NO 270

```
<211> LENGTH: 25
<212> TYPE: DNA
<213> ORGANISM: Artificial Sequence
<220> FEATURE:
<223> OTHER INFORMATION: DNA probe

<400> SEQUENCE: 270
ctctgtgcct ttcacttccg ggtga                                             25

<210> SEQ ID NO 271
<211> LENGTH: 25
<212> TYPE: DNA
<213> ORGANISM: Artificial Sequence
<220> FEATURE:
<223> OTHER INFORMATION: DNA probe

<400> SEQUENCE: 271
tctgtgcctt tcacttccgg gtgag                                             25

<210> SEQ ID NO 272
<211> LENGTH: 25
<212> TYPE: DNA
<213> ORGANISM: Artificial Sequence
<220> FEATURE:
<223> OTHER INFORMATION: DNA probe

<400> SEQUENCE: 272
ctgtgccttt cacttccggg tgagt                                             25

<210> SEQ ID NO 273
<211> LENGTH: 25
<212> TYPE: DNA
<213> ORGANISM: Artificial Sequence
<220> FEATURE:
<223> OTHER INFORMATION: DNA probe

<400> SEQUENCE: 273
tgtgcctttc acttccgggt gagtg                                             25

<210> SEQ ID NO 274
<211> LENGTH: 25
<212> TYPE: DNA
<213> ORGANISM: Artificial Sequence
<220> FEATURE:
<223> OTHER INFORMATION: DNA probe

<400> SEQUENCE: 274
gtgcctttca cttccgggtg agtgt                                             25

<210> SEQ ID NO 275
<211> LENGTH: 25
<212> TYPE: DNA
<213> ORGANISM: Artificial Sequence
<220> FEATURE:
<223> OTHER INFORMATION: DNA probe

<400> SEQUENCE: 275
tgcctttcac ttccgggtga gtgtc                                             25

<210> SEQ ID NO 276
<211> LENGTH: 25
<212> TYPE: DNA
<213> ORGANISM: Artificial Sequence
<220> FEATURE:
<223> OTHER INFORMATION: DNA probe

<400> SEQUENCE: 276
```
gcctttcact tccgggtgag tgtct                                          25

<210> SEQ ID NO 277
<211> LENGTH: 25
<212> TYPE: DNA
<213> ORGANISM: Artificial Sequence
<220> FEATURE:
<223> OTHER INFORMATION: DNA probe

<400> SEQUENCE: 277
cctttcactt ccgggtgagt gtctg                                          25

<210> SEQ ID NO 278
<211> LENGTH: 25
<212> TYPE: DNA
<213> ORGANISM: Artificial Sequence
<220> FEATURE:
<223> OTHER INFORMATION: DNA probe

<400> SEQUENCE: 278
ctttcacttc cgggtgagtg tctga                                          25

<210> SEQ ID NO 279
<211> LENGTH: 25
<212> TYPE: DNA
<213> ORGANISM: Artificial Sequence
<220> FEATURE:
<223> OTHER INFORMATION: DNA probe

<400> SEQUENCE: 279
tttcacttcc gggtgagtgt ctgag                                          25

<210> SEQ ID NO 280
<211> LENGTH: 25
<212> TYPE: DNA
<213> ORGANISM: Artificial Sequence
<220> FEATURE:
<223> OTHER INFORMATION: DNA probe

<400> SEQUENCE: 280
ttcacttccg ggtgagtgtc tgagt                                          25

<210> SEQ ID NO 281
<211> LENGTH: 25
<212> TYPE: DNA
<213> ORGANISM: Artificial Sequence
<220> FEATURE:
<223> OTHER INFORMATION: DNA probe

<400> SEQUENCE: 281
tcacttccgg gtgagtgtct gagtg                                          25

<210> SEQ ID NO 282
<211> LENGTH: 25
<212> TYPE: DNA
<213> ORGANISM: Artificial Sequence
<220> FEATURE:
<223> OTHER INFORMATION: DNA probe

<400> SEQUENCE: 282
cacttccggg tgagtgtctg agtgg                                          25

<210> SEQ ID NO 283
<211> LENGTH: 25
<212> TYPE: DNA
<213> ORGANISM: Artificial Sequence
<220> FEATURE:

<223> OTHER INFORMATION: DNA probe

<400> SEQUENCE: 283
acttccgggt gagtgtctga gtggc                25

<210> SEQ ID NO 284
<211> LENGTH: 25
<212> TYPE: DNA
<213> ORGANISM: Artificial Sequence
<220> FEATURE:
<223> OTHER INFORMATION: DNA probe

<400> SEQUENCE: 284
cttccgggtg agtgtctgag tggct                25

<210> SEQ ID NO 285
<211> LENGTH: 25
<212> TYPE: DNA
<213> ORGANISM: Artificial Sequence
<220> FEATURE:
<223> OTHER INFORMATION: DNA probe

<400> SEQUENCE: 285
ttccgggtga gtgtctgagt ggctc                25

<210> SEQ ID NO 286
<211> LENGTH: 25
<212> TYPE: DNA
<213> ORGANISM: Artificial Sequence
<220> FEATURE:
<223> OTHER INFORMATION: DNA probe

<400> SEQUENCE: 286
tccgggtgag tgtctgagtg gctca                25

<210> SEQ ID NO 287
<211> LENGTH: 25
<212> TYPE: DNA
<213> ORGANISM: Artificial Sequence
<220> FEATURE:
<223> OTHER INFORMATION: DNA probe

<400> SEQUENCE: 287
ccgggtgagt gtctgagtgg ctcac                25

<210> SEQ ID NO 288
<211> LENGTH: 25
<212> TYPE: DNA
<213> ORGANISM: Artificial Sequence
<220> FEATURE:
<223> OTHER INFORMATION: DNA probe

<400> SEQUENCE: 288
cgggtgagtg tctgagtggc tcacc                25

<210> SEQ ID NO 289
<211> LENGTH: 25
<212> TYPE: DNA
<213> ORGANISM: Artificial Sequence
<220> FEATURE:
<223> OTHER INFORMATION: DNA probe

<400> SEQUENCE: 289
gggtgagtgt ctgagtggct cacct                25

<210> SEQ ID NO 290

```
<211> LENGTH: 25
<212> TYPE: DNA
<213> ORGANISM: Artificial Sequence
<220> FEATURE:
<223> OTHER INFORMATION: DNA probe

<400> SEQUENCE: 290
ggtgagtgtc tgagtggctc acctg                                              25

<210> SEQ ID NO 291
<211> LENGTH: 25
<212> TYPE: DNA
<213> ORGANISM: Artificial Sequence
<220> FEATURE:
<223> OTHER INFORMATION: DNA probe

<400> SEQUENCE: 291
gtgagtgtct gagtggctca cctgg                                              25

<210> SEQ ID NO 292
<211> LENGTH: 25
<212> TYPE: DNA
<213> ORGANISM: Artificial Sequence
<220> FEATURE:
<223> OTHER INFORMATION: DNA probe

<400> SEQUENCE: 292
tgagtgtctg agtggctcac ctgga                                              25

<210> SEQ ID NO 293
<211> LENGTH: 25
<212> TYPE: DNA
<213> ORGANISM: Artificial Sequence
<220> FEATURE:
<223> OTHER INFORMATION: DNA probe

<400> SEQUENCE: 293
gagtgtctga gtggctcacc tggac                                              25

<210> SEQ ID NO 294
<211> LENGTH: 25
<212> TYPE: DNA
<213> ORGANISM: Artificial Sequence
<220> FEATURE:
<223> OTHER INFORMATION: DNA probe

<400> SEQUENCE: 294
agtgtctgag tggctcacct ggacc                                              25

<210> SEQ ID NO 295
<211> LENGTH: 25
<212> TYPE: DNA
<213> ORGANISM: Artificial Sequence
<220> FEATURE:
<223> OTHER INFORMATION: DNA probe

<400> SEQUENCE: 295
gtgtctgagt ggctcacctg gaccc                                              25

<210> SEQ ID NO 296
<211> LENGTH: 25
<212> TYPE: DNA
<213> ORGANISM: Artificial Sequence
<220> FEATURE:
<223> OTHER INFORMATION: DNA probe

<400> SEQUENCE: 296
```
tgtctgagtg gctcacctgg acccc                                                 25

<210> SEQ ID NO 297
<211> LENGTH: 25
<212> TYPE: DNA
<213> ORGANISM: Artificial Sequence
<220> FEATURE:
<223> OTHER INFORMATION: DNA probe

<400> SEQUENCE: 297
gtctgagtgg ctcacctgga cccct                                                 25

<210> SEQ ID NO 298
<211> LENGTH: 25
<212> TYPE: DNA
<213> ORGANISM: Artificial Sequence
<220> FEATURE:
<223> OTHER INFORMATION: DNA probe

<400> SEQUENCE: 298
tctgagtggc tcacctggac ccctg                                                 25

<210> SEQ ID NO 299
<211> LENGTH: 25
<212> TYPE: DNA
<213> ORGANISM: Artificial Sequence
<220> FEATURE:
<223> OTHER INFORMATION: DNA probe

<400> SEQUENCE: 299
ctgagtggct cacctggacc cctgg                                                 25

<210> SEQ ID NO 300
<211> LENGTH: 25
<212> TYPE: DNA
<213> ORGANISM: Artificial Sequence
<220> FEATURE:
<223> OTHER INFORMATION: DNA probe

<400> SEQUENCE: 300
tgagtggctc acctggaccc ctggg                                                 25

<210> SEQ ID NO 301
<211> LENGTH: 25
<212> TYPE: DNA
<213> ORGANISM: Artificial Sequence
<220> FEATURE:
<223> OTHER INFORMATION: DNA probe

<400> SEQUENCE: 301
gagtggctca cctggacccc tggga                                                 25

<210> SEQ ID NO 302
<211> LENGTH: 25
<212> TYPE: DNA
<213> ORGANISM: Artificial Sequence
<220> FEATURE:
<223> OTHER INFORMATION: DNA probe

<400> SEQUENCE: 302
agtggctcac ctggacccct gggac                                                 25

<210> SEQ ID NO 303
<211> LENGTH: 25
<212> TYPE: DNA
<213> ORGANISM: Artificial Sequence
<220> FEATURE:

```
<223> OTHER INFORMATION: DNA probe

<400> SEQUENCE: 303
gtggctcacc tggaccnctg ggacg                                   25

<210> SEQ ID NO 304
<211> LENGTH: 25
<212> TYPE: DNA
<213> ORGANISM: Artificial Sequence
<220> FEATURE:
<223> OTHER INFORMATION: DNA probe

<400> SEQUENCE: 304
tggctcacct ggaccnctgg gacgc                                   25

<210> SEQ ID NO 305
<211> LENGTH: 25
<212> TYPE: DNA
<213> ORGANISM: Artificial Sequence
<220> FEATURE:
<223> OTHER INFORMATION: DNA probe

<400> SEQUENCE: 305
ggctcacctg gaccnctggg acgcg                                   25

<210> SEQ ID NO 306
<211> LENGTH: 25
<212> TYPE: DNA
<213> ORGANISM: Artificial Sequence
<220> FEATURE:
<223> OTHER INFORMATION: DNA probe

<400> SEQUENCE: 306
gctcacctgg accnctggga cgcgc                                   25

<210> SEQ ID NO 307
<211> LENGTH: 25
<212> TYPE: DNA
<213> ORGANISM: Artificial Sequence
<220> FEATURE:
<223> OTHER INFORMATION: DNA probe

<400> SEQUENCE: 307
ctcacctgga ccnctgggac gcgcc                                   25

<210> SEQ ID NO 308
<211> LENGTH: 25
<212> TYPE: DNA
<213> ORGANISM: Artificial Sequence
<220> FEATURE:
<223> OTHER INFORMATION: DNA probe

<400> SEQUENCE: 308
tcacctggac ccntgggacg cgccg                                   25

<210> SEQ ID NO 309
<211> LENGTH: 25
<212> TYPE: DNA
<213> ORGANISM: Artificial Sequence
<220> FEATURE:
<223> OTHER INFORMATION: DNA probe

<400> SEQUENCE: 309
cacctggacc nctgggacgc gccga                                   25

<210> SEQ ID NO 310
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 310
acctggaccc ctgggacgcg ccgat                                      25

<210> SEQ ID NO 311
<211> LENGTH: 25
<212> TYPE: DNA
<213> ORGANISM: Artificial Sequence
<220> FEATURE:
<223> OTHER INFORMATION: DNA probe

<400> SEQUENCE: 311
cctggacccc tgggacgcgc cgatg                                      25

<210> SEQ ID NO 312
<211> LENGTH: 25
<212> TYPE: DNA
<213> ORGANISM: Artificial Sequence
<220> FEATURE:
<223> OTHER INFORMATION: DNA probe

<400> SEQUENCE: 312
ctggacccct gggacgcgcc gatga                                      25

<210> SEQ ID NO 313
<211> LENGTH: 25
<212> TYPE: DNA
<213> ORGANISM: Artificial Sequence
<220> FEATURE:
<223> OTHER INFORMATION: DNA probe

<400> SEQUENCE: 313
tggacccctg ggacgcgccg atgat                                      25

<210> SEQ ID NO 314
<211> LENGTH: 25
<212> TYPE: DNA
<213> ORGANISM: Artificial Sequence
<220> FEATURE:
<223> OTHER INFORMATION: DNA probe

<400> SEQUENCE: 314
ggacccctgg gacgcgccga tgatg                                      25

<210> SEQ ID NO 315
<211> LENGTH: 25
<212> TYPE: DNA
<213> ORGANISM: Artificial Sequence
<220> FEATURE:
<223> OTHER INFORMATION: DNA probe

<400> SEQUENCE: 315
gacccctggg acgcgccgat gatgt                                      25

<210> SEQ ID NO 316
<211> LENGTH: 25
<212> TYPE: DNA
<213> ORGANISM: Artificial Sequence
<220> FEATURE:
<223> OTHER INFORMATION: DNA probe

<400> SEQUENCE: 316
``` accccctggga cgcgccgatg atgtt 25

<210> SEQ ID NO 317
<211> LENGTH: 25
<212> TYPE: DNA
<213> ORGANISM: Artificial Sequence
<220> FEATURE:
<223> OTHER INFORMATION: DNA probe

<400> SEQUENCE: 317
cccctgggac gcgccgatga tgttg 25

<210> SEQ ID NO 318
<211> LENGTH: 25
<212> TYPE: DNA
<213> ORGANISM: Artificial Sequence
<220> FEATURE:
<223> OTHER INFORMATION: DNA probe

<400> SEQUENCE: 318
ccctgggacg cgccgatgat gttgg 25

<210> SEQ ID NO 319
<211> LENGTH: 25
<212> TYPE: DNA
<213> ORGANISM: Artificial Sequence
<220> FEATURE:
<223> OTHER INFORMATION: DNA probe

<400> SEQUENCE: 319
cctgggacgc gccgatgatg ttggt 25

<210> SEQ ID NO 320
<211> LENGTH: 25
<212> TYPE: DNA
<213> ORGANISM: Artificial Sequence
<220> FEATURE:
<223> OTHER INFORMATION: DNA probe

<400> SEQUENCE: 320
ctgggacgcg ccgatgatgt tggtc 25

<210> SEQ ID NO 321
<211> LENGTH: 25
<212> TYPE: DNA
<213> ORGANISM: Artificial Sequence
<220> FEATURE:
<223> OTHER INFORMATION: DNA probe

<400> SEQUENCE: 321
tgggacgcgc cgatgatgtt ggtct 25

<210> SEQ ID NO 322
<211> LENGTH: 25
<212> TYPE: DNA
<213> ORGANISM: Artificial Sequence
<220> FEATURE:
<223> OTHER INFORMATION: DNA probe

<400> SEQUENCE: 322
gggacgcgcc gatgatgttg gtctc 25

<210> SEQ ID NO 323
<211> LENGTH: 25
<212> TYPE: DNA
<213> ORGANISM: Artificial Sequence
<220> FEATURE:

```
<223> OTHER INFORMATION: DNA probe

<400> SEQUENCE: 323
ggacgcgccg atgatgttgg tctcg                                              25

<210> SEQ ID NO 324
<211> LENGTH: 25
<212> TYPE: DNA
<213> ORGANISM: Artificial Sequence
<220> FEATURE:
<223> OTHER INFORMATION: DNA probe

<400> SEQUENCE: 324
gacgcgccga tgatgttggt ctcgc                                              25

<210> SEQ ID NO 325
<211> LENGTH: 25
<212> TYPE: DNA
<213> ORGANISM: Artificial Sequence
<220> FEATURE:
<223> OTHER INFORMATION: DNA probe

<400> SEQUENCE: 325
acgcgccgat gatgttggtc tcgct                                              25

<210> SEQ ID NO 326
<211> LENGTH: 25
<212> TYPE: DNA
<213> ORGANISM: Artificial Sequence
<220> FEATURE:
<223> OTHER INFORMATION: DNA probe

<400> SEQUENCE: 326
cgcgccgatg atgttggtct cgctc                                              25

<210> SEQ ID NO 327
<211> LENGTH: 25
<212> TYPE: DNA
<213> ORGANISM: Artificial Sequence
<220> FEATURE:
<223> OTHER INFORMATION: DNA probe

<400> SEQUENCE: 327
gcgccgatga tgttggtctc gctcc                                              25

<210> SEQ ID NO 328
<211> LENGTH: 25
<212> TYPE: DNA
<213> ORGANISM: Artificial Sequence
<220> FEATURE:
<223> OTHER INFORMATION: DNA probe

<400> SEQUENCE: 328
cgccgatgat gttggtctcg ctccg                                              25

<210> SEQ ID NO 329
<211> LENGTH: 25
<212> TYPE: DNA
<213> ORGANISM: Artificial Sequence
<220> FEATURE:
<223> OTHER INFORMATION: DNA probe

<400> SEQUENCE: 329
gccgatgatg ttggtctcgc tccgg                                              25

<210> SEQ ID NO 330
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 330
ccgatgatgt tggtctcgct ccggc                                  25

<210> SEQ ID NO 331
<211> LENGTH: 25
<212> TYPE: DNA
<213> ORGANISM: Artificial Sequence
<220> FEATURE:
<223> OTHER INFORMATION: DNA probe

<400> SEQUENCE: 331
caagagtgtg gcaggtctcc tacat                                  25

<210> SEQ ID NO 332
<211> LENGTH: 25
<212> TYPE: DNA
<213> ORGANISM: Artificial Sequence
<220> FEATURE:
<223> OTHER INFORMATION: DNA probe

<400> SEQUENCE: 332
aagagtgtgg caggtctcct acata                                  25

<210> SEQ ID NO 333
<211> LENGTH: 25
<212> TYPE: DNA
<213> ORGANISM: Artificial Sequence
<220> FEATURE:
<223> OTHER INFORMATION: DNA probe

<400> SEQUENCE: 333
agagtgtggc aggtctccta catac                                  25

<210> SEQ ID NO 334
<211> LENGTH: 25
<212> TYPE: DNA
<213> ORGANISM: Artificial Sequence
<220> FEATURE:
<223> OTHER INFORMATION: DNA probe

<400> SEQUENCE: 334
gagtgtggca ggtctcctac atacc                                  25

<210> SEQ ID NO 335
<211> LENGTH: 25
<212> TYPE: DNA
<213> ORGANISM: Artificial Sequence
<220> FEATURE:
<223> OTHER INFORMATION: DNA probe

<400> SEQUENCE: 335
agtgtggcag gtctcctaca taccg                                  25

<210> SEQ ID NO 336
<211> LENGTH: 25
<212> TYPE: DNA
<213> ORGANISM: Artificial Sequence
<220> FEATURE:
<223> OTHER INFORMATION: DNA probe

<400> SEQUENCE: 336
```
gtgtggcagg tctcctacat accga                                              25

<210> SEQ ID NO 337
<211> LENGTH: 25
<212> TYPE: DNA
<213> ORGANISM: Artificial Sequence
<220> FEATURE:
<223> OTHER INFORMATION: DNA probe

<400> SEQUENCE: 337
tgtggcaggt ctcctacata ccgac                                              25

<210> SEQ ID NO 338
<211> LENGTH: 25
<212> TYPE: DNA
<213> ORGANISM: Artificial Sequence
<220> FEATURE:
<223> OTHER INFORMATION: DNA probe

<400> SEQUENCE: 338
gtggcaggtc tcctacatac cgacg                                              25

<210> SEQ ID NO 339
<211> LENGTH: 25
<212> TYPE: DNA
<213> ORGANISM: Artificial Sequence
<220> FEATURE:
<223> OTHER INFORMATION: DNA probe

<400> SEQUENCE: 339
tggcaggtct cctacatacc gacgc                                              25

<210> SEQ ID NO 340
<211> LENGTH: 25
<212> TYPE: DNA
<213> ORGANISM: Artificial Sequence
<220> FEATURE:
<223> OTHER INFORMATION: DNA probe

<400> SEQUENCE: 340
ggcaggtctc ctacataccg acgct                                              25

<210> SEQ ID NO 341
<211> LENGTH: 25
<212> TYPE: DNA
<213> ORGANISM: Artificial Sequence
<220> FEATURE:
<223> OTHER INFORMATION: DNA probe

<400> SEQUENCE: 341
gcaggtctcc tacataccga cgctg                                              25

<210> SEQ ID NO 342
<211> LENGTH: 25
<212> TYPE: DNA
<213> ORGANISM: Artificial Sequence
<220> FEATURE:
<223> OTHER INFORMATION: DNA probe

<400> SEQUENCE: 342
caggtctcct acataccgac gctgc                                              25

<210> SEQ ID NO 343
<211> LENGTH: 25
<212> TYPE: DNA
<213> ORGANISM: Artificial Sequence
<220> FEATURE:

<223> OTHER INFORMATION: DNA probe

<400> SEQUENCE: 343
aggtctccta cataccgacg ctgca                                    25

<210> SEQ ID NO 344
<211> LENGTH: 25
<212> TYPE: DNA
<213> ORGANISM: Artificial Sequence
<220> FEATURE:
<223> OTHER INFORMATION: DNA probe

<400> SEQUENCE: 344
ggtctcctac ataccgacgc tgcac                                    25

<210> SEQ ID NO 345
<211> LENGTH: 25
<212> TYPE: DNA
<213> ORGANISM: Artificial Sequence
<220> FEATURE:
<223> OTHER INFORMATION: DNA probe

<400> SEQUENCE: 345
gtctcctaca taccgacgct gcacc                                    25

<210> SEQ ID NO 346
<211> LENGTH: 25
<212> TYPE: DNA
<213> ORGANISM: Artificial Sequence
<220> FEATURE:
<223> OTHER INFORMATION: DNA probe

<400> SEQUENCE: 346
tctcctacat accgacgctg caccc                                    25

<210> SEQ ID NO 347
<211> LENGTH: 25
<212> TYPE: DNA
<213> ORGANISM: Artificial Sequence
<220> FEATURE:
<223> OTHER INFORMATION: DNA probe

<400> SEQUENCE: 347
ctcctacata ccgacgctgc acccc                                    25

<210> SEQ ID NO 348
<211> LENGTH: 25
<212> TYPE: DNA
<213> ORGANISM: Artificial Sequence
<220> FEATURE:
<223> OTHER INFORMATION: DNA probe

<400> SEQUENCE: 348
tcctacatac cgacgctgca cccca                                    25

<210> SEQ ID NO 349
<211> LENGTH: 25
<212> TYPE: DNA
<213> ORGANISM: Artificial Sequence
<220> FEATURE:
<223> OTHER INFORMATION: DNA probe

<400> SEQUENCE: 349
cctacatacc gacgctgcac cccag                                    25

<210> SEQ ID NO 350

-continued

<211> LENGTH: 25
<212> TYPE: DNA
<213> ORGANISM: Artificial Sequence
<220> FEATURE:
<223> OTHER INFORMATION: DNA probe

<400> SEQUENCE: 350
ctacataccg acgctgcacc ccagc                                    25

<210> SEQ ID NO 351
<211> LENGTH: 25
<212> TYPE: DNA
<213> ORGANISM: Artificial Sequence
<220> FEATURE:
<223> OTHER INFORMATION: DNA probe

<400> SEQUENCE: 351
tacataccga cgctgcaccc cagcc                                    25

<210> SEQ ID NO 352
<211> LENGTH: 25
<212> TYPE: DNA
<213> ORGANISM: Artificial Sequence
<220> FEATURE:
<223> OTHER INFORMATION: DNA probe

<400> SEQUENCE: 352
acataccgac gctgcacccc agcct                                    25

<210> SEQ ID NO 353
<211> LENGTH: 25
<212> TYPE: DNA
<213> ORGANISM: Artificial Sequence
<220> FEATURE:
<223> OTHER INFORMATION: DNA probe

<400> SEQUENCE: 353
cataccgacg ctgcacccca gcctg                                    25

<210> SEQ ID NO 354
<211> LENGTH: 25
<212> TYPE: DNA
<213> ORGANISM: Artificial Sequence
<220> FEATURE:
<223> OTHER INFORMATION: DNA probe

<400> SEQUENCE: 354
ataccgacgc tgcacccag cctga                                     25

<210> SEQ ID NO 355
<211> LENGTH: 25
<212> TYPE: DNA
<213> ORGANISM: Artificial Sequence
<220> FEATURE:
<223> OTHER INFORMATION: DNA probe

<400> SEQUENCE: 355
taccgacgct gcaccccagc ctgac                                    25

<210> SEQ ID NO 356
<211> LENGTH: 25
<212> TYPE: DNA
<213> ORGANISM: Artificial Sequence
<220> FEATURE:
<223> OTHER INFORMATION: DNA probe

<400> SEQUENCE: 356
accgacgctg cacccagcc tgacc                                    25

<210> SEQ ID NO 357
<211> LENGTH: 25
<212> TYPE: DNA
<213> ORGANISM: Artificial Sequence
<220> FEATURE:
<223> OTHER INFORMATION: DNA probe

<400> SEQUENCE: 357
ccgacgctgc accccagcct gaccg                                   25

<210> SEQ ID NO 358
<211> LENGTH: 25
<212> TYPE: DNA
<213> ORGANISM: Artificial Sequence
<220> FEATURE:
<223> OTHER INFORMATION: DNA probe

<400> SEQUENCE: 358
cgacgctgca ccccagcctg accgc                                   25

<210> SEQ ID NO 359
<211> LENGTH: 25
<212> TYPE: DNA
<213> ORGANISM: Artificial Sequence
<220> FEATURE:
<223> OTHER INFORMATION: DNA probe

<400> SEQUENCE: 359
gacgctgcac cccagcctga ccgcg                                   25

<210> SEQ ID NO 360
<211> LENGTH: 25
<212> TYPE: DNA
<213> ORGANISM: Artificial Sequence
<220> FEATURE:
<223> OTHER INFORMATION: DNA probe

<400> SEQUENCE: 360
acgctgcacc ccagcctgac cgcga                                   25

<210> SEQ ID NO 361
<211> LENGTH: 25
<212> TYPE: DNA
<213> ORGANISM: Artificial Sequence
<220> FEATURE:
<223> OTHER INFORMATION: DNA probe

<400> SEQUENCE: 361
cgctgcaccc cagcctgacc gcgaa                                   25

<210> SEQ ID NO 362
<211> LENGTH: 25
<212> TYPE: DNA
<213> ORGANISM: Artificial Sequence
<220> FEATURE:
<223> OTHER INFORMATION: DNA probe

<400> SEQUENCE: 362
gctgcacccc agcctgaccg cgaag                                   25

<210> SEQ ID NO 363
<211> LENGTH: 25
<212> TYPE: DNA
<213> ORGANISM: Artificial Sequence
<220> FEATURE:

<223> OTHER INFORMATION: DNA probe

<400> SEQUENCE: 363
ctgcacccca gcctgaccgc gaagg                                           25

<210> SEQ ID NO 364
<211> LENGTH: 25
<212> TYPE: DNA
<213> ORGANISM: Artificial Sequence
<220> FEATURE:
<223> OTHER INFORMATION: DNA probe

<400> SEQUENCE: 364
tgcaccccag cctgaccgcg aagga                                           25

<210> SEQ ID NO 365
<211> LENGTH: 25
<212> TYPE: DNA
<213> ORGANISM: Artificial Sequence
<220> FEATURE:
<223> OTHER INFORMATION: DNA probe

<400> SEQUENCE: 365
gcaccccagc ctgaccgcga aggag                                           25

<210> SEQ ID NO 366
<211> LENGTH: 25
<212> TYPE: DNA
<213> ORGANISM: Artificial Sequence
<220> FEATURE:
<223> OTHER INFORMATION: DNA probe

<400> SEQUENCE: 366
caccccagcc tgaccgcgaa ggagg                                           25

<210> SEQ ID NO 367
<211> LENGTH: 25
<212> TYPE: DNA
<213> ORGANISM: Artificial Sequence
<220> FEATURE:
<223> OTHER INFORMATION: DNA probe

<400> SEQUENCE: 367
accccagcct gaccgcgaag gaggc                                           25

<210> SEQ ID NO 368
<211> LENGTH: 25
<212> TYPE: DNA
<213> ORGANISM: Artificial Sequence
<220> FEATURE:
<223> OTHER INFORMATION: DNA probe

<400> SEQUENCE: 368
ccccagcctg accgcgaagg aggcg                                           25

<210> SEQ ID NO 369
<211> LENGTH: 25
<212> TYPE: DNA
<213> ORGANISM: Artificial Sequence
<220> FEATURE:
<223> OTHER INFORMATION: DNA probe

<400> SEQUENCE: 369
cccagcctga ccgcgaagga ggcgc                                           25

<210> SEQ ID NO 370

```
<211> LENGTH: 25
<212> TYPE: DNA
<213> ORGANISM: Artificial Sequence
<220> FEATURE:
<223> OTHER INFORMATION: DNA probe

<400> SEQUENCE: 370
ccagcctgac cgcgaaggag gcgcc                                       25

<210> SEQ ID NO 371
<211> LENGTH: 25
<212> TYPE: DNA
<213> ORGANISM: Artificial Sequence
<220> FEATURE:
<223> OTHER INFORMATION: DNA probe

<400> SEQUENCE: 371
cagcctgacc gcgaaggagg cgccc                                       25

<210> SEQ ID NO 372
<211> LENGTH: 25
<212> TYPE: DNA
<213> ORGANISM: Artificial Sequence
<220> FEATURE:
<223> OTHER INFORMATION: DNA probe

<400> SEQUENCE: 372
agcctgaccg cgaaggaggc gccca                                       25

<210> SEQ ID NO 373
<211> LENGTH: 25
<212> TYPE: DNA
<213> ORGANISM: Artificial Sequence
<220> FEATURE:
<223> OTHER INFORMATION: DNA probe

<400> SEQUENCE: 373
gcctgaccgc gaaggaggcg cccat                                       25

<210> SEQ ID NO 374
<211> LENGTH: 25
<212> TYPE: DNA
<213> ORGANISM: Artificial Sequence
<220> FEATURE:
<223> OTHER INFORMATION: DNA probe

<400> SEQUENCE: 374
cctgaccgcg aaggaggcgc ccatg                                       25

<210> SEQ ID NO 375
<211> LENGTH: 25
<212> TYPE: DNA
<213> ORGANISM: Artificial Sequence
<220> FEATURE:
<223> OTHER INFORMATION: DNA probe

<400> SEQUENCE: 375
ctgaccgcga aggaggcgcc catgg                                       25

<210> SEQ ID NO 376
<211> LENGTH: 25
<212> TYPE: DNA
<213> ORGANISM: Artificial Sequence
<220> FEATURE:
<223> OTHER INFORMATION: DNA probe

<400> SEQUENCE: 376
```
tgaccgcgaa ggaggcgccc atggt                                          25

<210> SEQ ID NO 377
<211> LENGTH: 25
<212> TYPE: DNA
<213> ORGANISM: Artificial Sequence
<220> FEATURE:
<223> OTHER INFORMATION: DNA probe

<400> SEQUENCE: 377
gaccgcgaag gaggcgccca tggtg                                          25

<210> SEQ ID NO 378
<211> LENGTH: 25
<212> TYPE: DNA
<213> ORGANISM: Artificial Sequence
<220> FEATURE:
<223> OTHER INFORMATION: DNA probe

<400> SEQUENCE: 378
accgcgaagg aggcgcccat ggtgg                                          25

<210> SEQ ID NO 379
<211> LENGTH: 25
<212> TYPE: DNA
<213> ORGANISM: Artificial Sequence
<220> FEATURE:
<223> OTHER INFORMATION: DNA probe

<400> SEQUENCE: 379
ccgcgaagga ggcgcccatg gtggt                                          25

<210> SEQ ID NO 380
<211> LENGTH: 25
<212> TYPE: DNA
<213> ORGANISM: Artificial Sequence
<220> FEATURE:
<223> OTHER INFORMATION: DNA probe

<400> SEQUENCE: 380
cgcgaaggag gcgcccatgg tggtc                                          25

<210> SEQ ID NO 381
<211> LENGTH: 25
<212> TYPE: DNA
<213> ORGANISM: Artificial Sequence
<220> FEATURE:
<223> OTHER INFORMATION: DNA probe

<400> SEQUENCE: 381
gcgaaggagg cgcccatggt ggtca                                          25

<210> SEQ ID NO 382
<211> LENGTH: 25
<212> TYPE: DNA
<213> ORGANISM: Artificial Sequence
<220> FEATURE:
<223> OTHER INFORMATION: DNA probe

<400> SEQUENCE: 382
cgaaggaggc gcccatggtg gtcat                                          25

<210> SEQ ID NO 383
<211> LENGTH: 25
<212> TYPE: DNA
<213> ORGANISM: Artificial Sequence
<220> FEATURE:

```
<223> OTHER INFORMATION: DNA probe

<400> SEQUENCE: 383
gaaggaggcg cccatggtgg tcatg                                    25

<210> SEQ ID NO 384
<211> LENGTH: 25
<212> TYPE: DNA
<213> ORGANISM: Artificial Sequence
<220> FEATURE:
<223> OTHER INFORMATION: DNA probe

<400> SEQUENCE: 384
aaggaggcgc ccatggtggt catgc                                    25

<210> SEQ ID NO 385
<211> LENGTH: 25
<212> TYPE: DNA
<213> ORGANISM: Artificial Sequence
<220> FEATURE:
<223> OTHER INFORMATION: DNA probe

<400> SEQUENCE: 385
aggaggcgcc catggtggtc atgcg                                    25

<210> SEQ ID NO 386
<211> LENGTH: 25
<212> TYPE: DNA
<213> ORGANISM: Artificial Sequence
<220> FEATURE:
<223> OTHER INFORMATION: DNA probe

<400> SEQUENCE: 386
ggaggcgccc atggtggtca tgcgg                                    25

<210> SEQ ID NO 387
<211> LENGTH: 25
<212> TYPE: DNA
<213> ORGANISM: Artificial Sequence
<220> FEATURE:
<223> OTHER INFORMATION: DNA probe

<400> SEQUENCE: 387
gaggcgccca tggtggtcat gcgga                                    25

<210> SEQ ID NO 388
<211> LENGTH: 25
<212> TYPE: DNA
<213> ORGANISM: Artificial Sequence
<220> FEATURE:
<223> OTHER INFORMATION: DNA probe

<400> SEQUENCE: 388
aggcgcccat ggtggtcatg cggat                                    25

<210> SEQ ID NO 389
<211> LENGTH: 25
<212> TYPE: DNA
<213> ORGANISM: Artificial Sequence
<220> FEATURE:
<223> OTHER INFORMATION: DNA probe

<400> SEQUENCE: 389
ggcgcccatg gtggtcatgc ggatg                                    25

<210> SEQ ID NO 390
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 390
gcgcccatgg tggtcatgcg gatgc                                          25

<210> SEQ ID NO 391
<211> LENGTH: 25
<212> TYPE: DNA
<213> ORGANISM: Artificial Sequence
<220> FEATURE:
<223> OTHER INFORMATION: DNA probe

<400> SEQUENCE: 391
cgcccatggt ggtcatgcgg atgct                                          25

<210> SEQ ID NO 392
<211> LENGTH: 25
<212> TYPE: DNA
<213> ORGANISM: Artificial Sequence
<220> FEATURE:
<223> OTHER INFORMATION: DNA probe

<400> SEQUENCE: 392
gcccatggtg gtcatgcgga tgctg                                          25

<210> SEQ ID NO 393
<211> LENGTH: 25
<212> TYPE: DNA
<213> ORGANISM: Artificial Sequence
<220> FEATURE:
<223> OTHER INFORMATION: DNA probe

<400> SEQUENCE: 393
cccatggtgg tcatgcggat gctgc                                          25

<210> SEQ ID NO 394
<211> LENGTH: 25
<212> TYPE: DNA
<213> ORGANISM: Artificial Sequence
<220> FEATURE:
<223> OTHER INFORMATION: DNA probe

<400> SEQUENCE: 394
ccatggtggt catgcggatg ctgcc                                          25

<210> SEQ ID NO 395
<211> LENGTH: 25
<212> TYPE: DNA
<213> ORGANISM: Artificial Sequence
<220> FEATURE:
<223> OTHER INFORMATION: DNA probe

<400> SEQUENCE: 395
catggtggtc atgcggatgc tgccg                                          25

<210> SEQ ID NO 396
<211> LENGTH: 25
<212> TYPE: DNA
<213> ORGANISM: Artificial Sequence
<220> FEATURE:
<223> OTHER INFORMATION: DNA probe

<400> SEQUENCE: 396
```

```
atggtggtca tgcggatgct gccgt                                          25

<210> SEQ ID NO 397
<211> LENGTH: 25
<212> TYPE: DNA
<213> ORGANISM: Artificial Sequence
<220> FEATURE:
<223> OTHER INFORMATION: DNA probe

<400> SEQUENCE: 397
tggtggtcat gcggatgctg ccgtt                                          25

<210> SEQ ID NO 398
<211> LENGTH: 25
<212> TYPE: DNA
<213> ORGANISM: Artificial Sequence
<220> FEATURE:
<223> OTHER INFORMATION: DNA probe

<400> SEQUENCE: 398
ggtggtcatg cggatgctgc cgttc                                          25

<210> SEQ ID NO 399
<211> LENGTH: 25
<212> TYPE: DNA
<213> ORGANISM: Artificial Sequence
<220> FEATURE:
<223> OTHER INFORMATION: DNA probe

<400> SEQUENCE: 399
gtggtcatgc ggatgctgcc gttcc                                          25

<210> SEQ ID NO 400
<211> LENGTH: 25
<212> TYPE: DNA
<213> ORGANISM: Artificial Sequence
<220> FEATURE:
<223> OTHER INFORMATION: DNA probe

<400> SEQUENCE: 400
tggtcatgcg gatgctgccg ttcct                                          25

<210> SEQ ID NO 401
<211> LENGTH: 25
<212> TYPE: DNA
<213> ORGANISM: Artificial Sequence
<220> FEATURE:
<223> OTHER INFORMATION: DNA probe

<400> SEQUENCE: 401
ggtcatgcgg atgctgccgt tccta                                          25

<210> SEQ ID NO 402
<211> LENGTH: 25
<212> TYPE: DNA
<213> ORGANISM: Artificial Sequence
<220> FEATURE:
<223> OTHER INFORMATION: DNA probe

<400> SEQUENCE: 402
gtcatgcgga tgctgccgtt cctaa                                          25

<210> SEQ ID NO 403
<211> LENGTH: 25
<212> TYPE: DNA
<213> ORGANISM: Artificial Sequence
<220> FEATURE:
```

<223> OTHER INFORMATION: DNA probe

<400> SEQUENCE: 403
tcatgcggat gctgccgttc ctaat 25

<210> SEQ ID NO 404
<211> LENGTH: 25
<212> TYPE: DNA
<213> ORGANISM: Artificial Sequence
<220> FEATURE:
<223> OTHER INFORMATION: DNA probe

<400> SEQUENCE: 404
catgcggatg ctgccgttcc taatg 25

<210> SEQ ID NO 405
<211> LENGTH: 25
<212> TYPE: DNA
<213> ORGANISM: Artificial Sequence
<220> FEATURE:
<223> OTHER INFORMATION: DNA probe

<400> SEQUENCE: 405
atgcggatgc tgccgttcct aatgt 25

<210> SEQ ID NO 406
<211> LENGTH: 25
<212> TYPE: DNA
<213> ORGANISM: Artificial Sequence
<220> FEATURE:
<223> OTHER INFORMATION: DNA probe

<400> SEQUENCE: 406
tgcggatgct gccgttccta atgta 25

<210> SEQ ID NO 407
<211> LENGTH: 25
<212> TYPE: DNA
<213> ORGANISM: Artificial Sequence
<220> FEATURE:
<223> OTHER INFORMATION: DNA probe

<400> SEQUENCE: 407
gcggatgctg ccgttcctaa tgtag 25

<210> SEQ ID NO 408
<211> LENGTH: 25
<212> TYPE: DNA
<213> ORGANISM: Artificial Sequence
<220> FEATURE:
<223> OTHER INFORMATION: DNA probe

<400> SEQUENCE: 408
cggatgctgc cgttcctaat gtagc 25

<210> SEQ ID NO 409
<211> LENGTH: 25
<212> TYPE: DNA
<213> ORGANISM: Artificial Sequence
<220> FEATURE:
<223> OTHER INFORMATION: DNA probe

<400> SEQUENCE: 409
ggatgctgcc gttcctaatg tagcg 25

<210> SEQ ID NO 410

```
<211> LENGTH: 25
<212> TYPE: DNA
<213> ORGANISM: Artificial Sequence
<220> FEATURE:
<223> OTHER INFORMATION: DNA probe

<400> SEQUENCE: 410
gatgctgccg ttcctaatgt agcgg                                          25

<210> SEQ ID NO 411
<211> LENGTH: 25
<212> TYPE: DNA
<213> ORGANISM: Artificial Sequence
<220> FEATURE:
<223> OTHER INFORMATION: DNA probe

<400> SEQUENCE: 411
atgctgccgt tcctaatgta gcggg                                          25

<210> SEQ ID NO 412
<211> LENGTH: 25
<212> TYPE: DNA
<213> ORGANISM: Artificial Sequence
<220> FEATURE:
<223> OTHER INFORMATION: DNA probe

<400> SEQUENCE: 412
tgctgccgtt cctaatgtag cggga                                          25

<210> SEQ ID NO 413
<211> LENGTH: 25
<212> TYPE: DNA
<213> ORGANISM: Artificial Sequence
<220> FEATURE:
<223> OTHER INFORMATION: DNA probe

<400> SEQUENCE: 413
gctgccgttc ctaatgtagc gggac                                          25

<210> SEQ ID NO 414
<211> LENGTH: 25
<212> TYPE: DNA
<213> ORGANISM: Artificial Sequence
<220> FEATURE:
<223> OTHER INFORMATION: DNA probe

<400> SEQUENCE: 414
ctgccgttcc taatgtagcg ggact                                          25

<210> SEQ ID NO 415
<211> LENGTH: 25
<212> TYPE: DNA
<213> ORGANISM: Artificial Sequence
<220> FEATURE:
<223> OTHER INFORMATION: DNA probe

<400> SEQUENCE: 415
tgccgttcct aatgtagcgg gactt                                          25

<210> SEQ ID NO 416
<211> LENGTH: 25
<212> TYPE: DNA
<213> ORGANISM: Artificial Sequence
<220> FEATURE:
<223> OTHER INFORMATION: DNA probe

<400> SEQUENCE: 416
```
gccgttccta atgtagcggg acttt      25

<210> SEQ ID NO 417
<211> LENGTH: 25
<212> TYPE: DNA
<213> ORGANISM: Artificial Sequence
<220> FEATURE:
<223> OTHER INFORMATION: DNA probe

<400> SEQUENCE: 417
ccgttcctaa tgtagcggga ctttc      25

<210> SEQ ID NO 418
<211> LENGTH: 25
<212> TYPE: DNA
<213> ORGANISM: Artificial Sequence
<220> FEATURE:
<223> OTHER INFORMATION: DNA probe

<400> SEQUENCE: 418
cgttcctaat gtagcgggac tttct      25

<210> SEQ ID NO 419
<211> LENGTH: 25
<212> TYPE: DNA
<213> ORGANISM: Artificial Sequence
<220> FEATURE:
<223> OTHER INFORMATION: DNA probe

<400> SEQUENCE: 419
gttcctaatg tagcgggact ttctc      25

<210> SEQ ID NO 420
<211> LENGTH: 25
<212> TYPE: DNA
<213> ORGANISM: Artificial Sequence
<220> FEATURE:
<223> OTHER INFORMATION: DNA probe

<400> SEQUENCE: 420
ttcctaatgt agcgggactt tctcc      25

<210> SEQ ID NO 421
<211> LENGTH: 25
<212> TYPE: DNA
<213> ORGANISM: Artificial Sequence
<220> FEATURE:
<223> OTHER INFORMATION: DNA probe

<400> SEQUENCE: 421
tcctaatgta gcgggacttt ctcct      25

<210> SEQ ID NO 422
<211> LENGTH: 25
<212> TYPE: DNA
<213> ORGANISM: Artificial Sequence
<220> FEATURE:
<223> OTHER INFORMATION: DNA probe

<400> SEQUENCE: 422
cctaatgtag cgggactttc tcctg      25

<210> SEQ ID NO 423
<211> LENGTH: 25
<212> TYPE: DNA
<213> ORGANISM: Artificial Sequence
<220> FEATURE:

-continued

<223> OTHER INFORMATION: DNA probe

<400> SEQUENCE: 423
ctaatgtagc gggactttct cctgg                                         25

<210> SEQ ID NO 424
<211> LENGTH: 25
<212> TYPE: DNA
<213> ORGANISM: Artificial Sequence
<220> FEATURE:
<223> OTHER INFORMATION: DNA probe

<400> SEQUENCE: 424
taatgtagcg ggactttctc ctgga                                         25

<210> SEQ ID NO 425
<211> LENGTH: 25
<212> TYPE: DNA
<213> ORGANISM: Artificial Sequence
<220> FEATURE:
<223> OTHER INFORMATION: DNA probe

<400> SEQUENCE: 425
aatgtagcgg gactttctcc tggac                                         25

<210> SEQ ID NO 426
<211> LENGTH: 25
<212> TYPE: DNA
<213> ORGANISM: Artificial Sequence
<220> FEATURE:
<223> OTHER INFORMATION: DNA probe

<400> SEQUENCE: 426
atgtagcggg actttctcct ggacg                                         25

<210> SEQ ID NO 427
<211> LENGTH: 25
<212> TYPE: DNA
<213> ORGANISM: Artificial Sequence
<220> FEATURE:
<223> OTHER INFORMATION: DNA probe

<400> SEQUENCE: 427
tgtagcggga ctttctcctg gacgc                                         25

<210> SEQ ID NO 428
<211> LENGTH: 25
<212> TYPE: DNA
<213> ORGANISM: Artificial Sequence
<220> FEATURE:
<223> OTHER INFORMATION: DNA probe

<400> SEQUENCE: 428 gtagcggac tttctcctgg acgcg                                          25

<210> SEQ ID NO 429
<211> LENGTH: 25
<212> TYPE: DNA
<213> ORGANISM: Artificial Sequence
<220> FEATURE:
<223> OTHER INFORMATION: DNA probe

<400> SEQUENCE: 429
tagcgggact ttctcctgga cgcga                                         25

<210> SEQ ID NO 430

```
<211> LENGTH: 25
<212> TYPE: DNA
<213> ORGANISM: Artificial Sequence
<220> FEATURE:
<223> OTHER INFORMATION: DNA probe

<400> SEQUENCE: 430
agcgggactt tctcctggac gcgag                                           25

<210> SEQ ID NO 431
<211> LENGTH: 25
<212> TYPE: DNA
<213> ORGANISM: Artificial Sequence
<220> FEATURE:
<223> OTHER INFORMATION: DNA probe

<400> SEQUENCE: 431
gcgggacttt ctcctggacg cgaga                                           25

<210> SEQ ID NO 432
<211> LENGTH: 25
<212> TYPE: DNA
<213> ORGANISM: Artificial Sequence
<220> FEATURE:
<223> OTHER INFORMATION: DNA probe

<400> SEQUENCE: 432
cgggactttc tcctggacgc gagaa                                           25

<210> SEQ ID NO 433
<211> LENGTH: 25
<212> TYPE: DNA
<213> ORGANISM: Artificial Sequence
<220> FEATURE:
<223> OTHER INFORMATION: DNA probe

<400> SEQUENCE: 433
gggactttct cctggacgcg agaac                                           25

<210> SEQ ID NO 434
<211> LENGTH: 25
<212> TYPE: DNA
<213> ORGANISM: Artificial Sequence
<220> FEATURE:
<223> OTHER INFORMATION: DNA probe

<400> SEQUENCE: 434
ggactttctc ctggacgcga gaacc                                           25

<210> SEQ ID NO 435
<211> LENGTH: 25
<212> TYPE: DNA
<213> ORGANISM: Artificial Sequence
<220> FEATURE:
<223> OTHER INFORMATION: DNA probe

<400> SEQUENCE: 435
gactttctcc tggacgcgag aacct                                           25

<210> SEQ ID NO 436
<211> LENGTH: 25
<212> TYPE: DNA
<213> ORGANISM: Artificial Sequence
<220> FEATURE:
<223> OTHER INFORMATION: DNA probe

<400> SEQUENCE: 436
```
actttctcct ggacgcgaga acctg                                              25

<210> SEQ ID NO 437
<211> LENGTH: 25
<212> TYPE: DNA
<213> ORGANISM: Artificial Sequence
<220> FEATURE:
<223> OTHER INFORMATION: DNA probe

<400> SEQUENCE: 437
ctttctcctg gacgcgagaa cctgg                                              25

<210> SEQ ID NO 438
<211> LENGTH: 25
<212> TYPE: DNA
<213> ORGANISM: Artificial Sequence
<220> FEATURE:
<223> OTHER INFORMATION: DNA probe

<400> SEQUENCE: 438
tttctcctgg acgcgagaac ctggc                                              25

<210> SEQ ID NO 439
<211> LENGTH: 25
<212> TYPE: DNA
<213> ORGANISM: Artificial Sequence
<220> FEATURE:
<223> OTHER INFORMATION: DNA probe

<400> SEQUENCE: 439
ttctcctgga cgcgagaacc tggcg                                              25

<210> SEQ ID NO 440
<211> LENGTH: 25
<212> TYPE: DNA
<213> ORGANISM: Artificial Sequence
<220> FEATURE:
<223> OTHER INFORMATION: DNA probe

<400> SEQUENCE: 440
tctcctggac gcgagaacct ggcgc                                              25

<210> SEQ ID NO 441
<211> LENGTH: 25
<212> TYPE: DNA
<213> ORGANISM: Artificial Sequence
<220> FEATURE:
<223> OTHER INFORMATION: DNA probe

<400> SEQUENCE: 441
ctcctggacg cgagaacctg gcgcc                                              25

<210> SEQ ID NO 442
<211> LENGTH: 25
<212> TYPE: DNA
<213> ORGANISM: Artificial Sequence
<220> FEATURE:
<223> OTHER INFORMATION: DNA probe

<400> SEQUENCE: 442
tcctggacgc gagaacctgg cgccg                                              25

<210> SEQ ID NO 443
<211> LENGTH: 25
<212> TYPE: DNA
<213> ORGANISM: Artificial Sequence
<220> FEATURE:

<223> OTHER INFORMATION: DNA probe

<400> SEQUENCE: 443
cctggacgcg agaacctggc gccgc                                    25

<210> SEQ ID NO 444
<211> LENGTH: 25
<212> TYPE: DNA
<213> ORGANISM: Artificial Sequence
<220> FEATURE:
<223> OTHER INFORMATION: DNA probe

<400> SEQUENCE: 444
ctggacgcga gaacctggcg ccgcc                                    25

<210> SEQ ID NO 445
<211> LENGTH: 25
<212> TYPE: DNA
<213> ORGANISM: Artificial Sequence
<220> FEATURE:
<223> OTHER INFORMATION: DNA probe

<400> SEQUENCE: 445
tggacgcgag aacctggcgc cgcct                                    25

<210> SEQ ID NO 446
<211> LENGTH: 25
<212> TYPE: DNA
<213> ORGANISM: Artificial Sequence
<220> FEATURE:
<223> OTHER INFORMATION: DNA probe

<400> SEQUENCE: 446
ggacgcgaga acctggcgcc gcctg                                    25

<210> SEQ ID NO 447
<211> LENGTH: 25
<212> TYPE: DNA
<213> ORGANISM: Artificial Sequence
<220> FEATURE:
<223> OTHER INFORMATION: DNA probe

<400> SEQUENCE: 447
gacgcgagaa cctggcgccg cctgt                                    25

<210> SEQ ID NO 448
<211> LENGTH: 25
<212> TYPE: DNA
<213> ORGANISM: Artificial Sequence
<220> FEATURE:
<223> OTHER INFORMATION: DNA probe

<400> SEQUENCE: 448
acgcgagaac ctggcgccgc ctgta                                    25

<210> SEQ ID NO 449
<211> LENGTH: 25
<212> TYPE: DNA
<213> ORGANISM: Artificial Sequence
<220> FEATURE:
<223> OTHER INFORMATION: DNA probe

<400> SEQUENCE: 449
cgcgagaacc tggcgccgcc tgtac                                    25

<210> SEQ ID NO 450

```
<211> LENGTH: 25
<212> TYPE: DNA
<213> ORGANISM: Artificial Sequence
<220> FEATURE:
<223> OTHER INFORMATION: DNA probe

<400> SEQUENCE: 450
gcgagaacct ggcgccgcct gtacc                                              25

<210> SEQ ID NO 451
<211> LENGTH: 25
<212> TYPE: DNA
<213> ORGANISM: Artificial Sequence
<220> FEATURE:
<223> OTHER INFORMATION: DNA probe

<400> SEQUENCE: 451
cgagaacctg gcgccgcctg taccg                                              25

<210> SEQ ID NO 452
<211> LENGTH: 25
<212> TYPE: DNA
<213> ORGANISM: Artificial Sequence
<220> FEATURE:
<223> OTHER INFORMATION: DNA probe

<400> SEQUENCE: 452
gagaacctgg cgccgcctgt accgt                                              25

<210> SEQ ID NO 453
<211> LENGTH: 25
<212> TYPE: DNA
<213> ORGANISM: Artificial Sequence
<220> FEATURE:
<223> OTHER INFORMATION: DNA probe

<400> SEQUENCE: 453
agaacctggc gccgcctgta ccgtc                                              25

<210> SEQ ID NO 454
<211> LENGTH: 25
<212> TYPE: DNA
<213> ORGANISM: Artificial Sequence
<220> FEATURE:
<223> OTHER INFORMATION: DNA probe

<400> SEQUENCE: 454
gaacctggcg ccgcctgtac cgtcg                                              25

<210> SEQ ID NO 455
<211> LENGTH: 25
<212> TYPE: DNA
<213> ORGANISM: Artificial Sequence
<220> FEATURE:
<223> OTHER INFORMATION: DNA probe

<400> SEQUENCE: 455
aacctggcgc cgcctgtacc gtcga                                              25

<210> SEQ ID NO 456
<211> LENGTH: 25
<212> TYPE: DNA
<213> ORGANISM: Artificial Sequence
<220> FEATURE:
<223> OTHER INFORMATION: DNA probe

<400> SEQUENCE: 456
```
acctggcgcc gcctgtaccg tcgag					25

<210> SEQ ID NO 457
<211> LENGTH: 25
<212> TYPE: DNA
<213> ORGANISM: Artificial Sequence
<220> FEATURE:
<223> OTHER INFORMATION: DNA probe

<400> SEQUENCE: 457
cctggcgccg cctgtaccgt cgagt					25

<210> SEQ ID NO 458
<211> LENGTH: 25
<212> TYPE: DNA
<213> ORGANISM: Artificial Sequence
<220> FEATURE:
<223> OTHER INFORMATION: DNA probe

<400> SEQUENCE: 458
ctggcgccgc ctgtaccgtc gagtc					25

<210> SEQ ID NO 459
<211> LENGTH: 25
<212> TYPE: DNA
<213> ORGANISM: Artificial Sequence
<220> FEATURE:
<223> OTHER INFORMATION: DNA probe

<400> SEQUENCE: 459
tggcgccgcc tgtaccgtcg agtct					25

<210> SEQ ID NO 460
<211> LENGTH: 25
<212> TYPE: DNA
<213> ORGANISM: Artificial Sequence
<220> FEATURE:
<223> OTHER INFORMATION: DNA probe

<400> SEQUENCE: 460
ggcgccgcct gtaccgtcga gtctg					25

<210> SEQ ID NO 461
<211> LENGTH: 25
<212> TYPE: DNA
<213> ORGANISM: Artificial Sequence
<220> FEATURE:
<223> OTHER INFORMATION: DNA probe

<400> SEQUENCE: 461
gcgccgcctg taccgtcgag tctgg					25

<210> SEQ ID NO 462
<211> LENGTH: 25
<212> TYPE: DNA
<213> ORGANISM: Artificial Sequence
<220> FEATURE:
<223> OTHER INFORMATION: DNA probe

<400> SEQUENCE: 462
cgccgcctgt accgtcgagt ctggt					25

<210> SEQ ID NO 463
<211> LENGTH: 25
<212> TYPE: DNA
<213> ORGANISM: Artificial Sequence
<220> FEATURE:

```
<223> OTHER INFORMATION: DNA probe

<400> SEQUENCE: 463
gccgcctgta ccgtcgagtc tggtg                                    25

<210> SEQ ID NO 464
<211> LENGTH: 25
<212> TYPE: DNA
<213> ORGANISM: Artificial Sequence
<220> FEATURE:
<223> OTHER INFORMATION: DNA probe

<400> SEQUENCE: 464
ccgcctgtac cgtcgagtct ggtgg                                    25

<210> SEQ ID NO 465
<211> LENGTH: 25
<212> TYPE: DNA
<213> ORGANISM: Artificial Sequence
<220> FEATURE:
<223> OTHER INFORMATION: DNA probe

<400> SEQUENCE: 465
cgcctgtacc gtcgagtctg gtggt                                    25

<210> SEQ ID NO 466
<211> LENGTH: 25
<212> TYPE: DNA
<213> ORGANISM: Artificial Sequence
<220> FEATURE:
<223> OTHER INFORMATION: DNA probe

<400> SEQUENCE: 466
gcctgtaccg tcgagtctgg tggtt                                    25

<210> SEQ ID NO 467
<211> LENGTH: 25
<212> TYPE: DNA
<213> ORGANISM: Artificial Sequence
<220> FEATURE:
<223> OTHER INFORMATION: DNA probe

<400> SEQUENCE: 467
cctgtaccgt cgagtctggt ggttc                                    25

<210> SEQ ID NO 468
<211> LENGTH: 25
<212> TYPE: DNA
<213> ORGANISM: Artificial Sequence
<220> FEATURE:
<223> OTHER INFORMATION: DNA probe

<400> SEQUENCE: 468
ctgtaccgtc gagtctggtg gttcg                                    25

<210> SEQ ID NO 469
<211> LENGTH: 25
<212> TYPE: DNA
<213> ORGANISM: Artificial Sequence
<220> FEATURE:
<223> OTHER INFORMATION: DNA probe

<400> SEQUENCE: 469
tgtaccgtcg agtctggtgg ttcgt                                    25

<210> SEQ ID NO 470
```

```
<211> LENGTH: 25
<212> TYPE: DNA
<213> ORGANISM: Artificial Sequence
<220> FEATURE:
<223> OTHER INFORMATION: DNA probe

<400> SEQUENCE: 470
gtaccgtcga gtctggtggt tcgtg                                          25

<210> SEQ ID NO 471
<211> LENGTH: 25
<212> TYPE: DNA
<213> ORGANISM: Artificial Sequence
<220> FEATURE:
<223> OTHER INFORMATION: DNA probe

<400> SEQUENCE: 471
taccgtcgag tctggtggtt cgtgt                                          25

<210> SEQ ID NO 472
<211> LENGTH: 25
<212> TYPE: DNA
<213> ORGANISM: Artificial Sequence
<220> FEATURE:
<223> OTHER INFORMATION: DNA probe

<400> SEQUENCE: 472
accgtcgagt ctggtggttc gtgtt                                          25

<210> SEQ ID NO 473
<211> LENGTH: 25
<212> TYPE: DNA
<213> ORGANISM: Artificial Sequence
<220> FEATURE:
<223> OTHER INFORMATION: DNA probe

<400> SEQUENCE: 473
ccgtcgagtc tggtggttcg tgttc                                          25

<210> SEQ ID NO 474
<211> LENGTH: 25
<212> TYPE: DNA
<213> ORGANISM: Artificial Sequence
<220> FEATURE:
<223> OTHER INFORMATION: DNA probe

<400> SEQUENCE: 474
cgtcgagtct ggtggttcgt gttca                                          25

<210> SEQ ID NO 475
<211> LENGTH: 25
<212> TYPE: DNA
<213> ORGANISM: Artificial Sequence
<220> FEATURE:
<223> OTHER INFORMATION: DNA probe

<400> SEQUENCE: 475
gtcgagtctg gtggttcgtg ttcac                                          25

<210> SEQ ID NO 476
<211> LENGTH: 25
<212> TYPE: DNA
<213> ORGANISM: Artificial Sequence
<220> FEATURE:
<223> OTHER INFORMATION: DNA probe

<400> SEQUENCE: 476
```
tcgagtctgg tggttcgtgt tcacc        25

<210> SEQ ID NO 477
<211> LENGTH: 25
<212> TYPE: DNA
<213> ORGANISM: Artificial Sequence
<220> FEATURE:
<223> OTHER INFORMATION: DNA probe

<400> SEQUENCE: 477
cgagtctggt ggttcgtgtt caccc        25

<210> SEQ ID NO 478
<211> LENGTH: 25
<212> TYPE: DNA
<213> ORGANISM: Artificial Sequence
<220> FEATURE:
<223> OTHER INFORMATION: DNA probe

<400> SEQUENCE: 478
gagtctggtg gttcgtgttc accct        25

<210> SEQ ID NO 479
<211> LENGTH: 25
<212> TYPE: DNA
<213> ORGANISM: Artificial Sequence
<220> FEATURE:
<223> OTHER INFORMATION: DNA probe

<400> SEQUENCE: 479
agtctggtgg ttcgtgttca ccctc        25

<210> SEQ ID NO 480
<211> LENGTH: 25
<212> TYPE: DNA
<213> ORGANISM: Artificial Sequence
<220> FEATURE:
<223> OTHER INFORMATION: DNA probe

<400> SEQUENCE: 480
gtctggtggt tcgtgttcac cctcc        25

<210> SEQ ID NO 481
<211> LENGTH: 25
<212> TYPE: DNA
<213> ORGANISM: Artificial Sequence
<220> FEATURE:
<223> OTHER INFORMATION: DNA probe

<400> SEQUENCE: 481
tctggtggtt cgtgttcacc ctccg        25

<210> SEQ ID NO 482
<211> LENGTH: 25
<212> TYPE: DNA
<213> ORGANISM: Artificial Sequence
<220> FEATURE:
<223> OTHER INFORMATION: DNA probe

<400> SEQUENCE: 482
ctggtggttc gtgttcaccc tccgc        25

<210> SEQ ID NO 483
<211> LENGTH: 25
<212> TYPE: DNA
<213> ORGANISM: Artificial Sequence
<220> FEATURE:

<223> OTHER INFORMATION: DNA probe

<400> SEQUENCE: 483
tggtggttcg tgttcaccct ccgcc                                          25

<210> SEQ ID NO 484
<211> LENGTH: 25
<212> TYPE: DNA
<213> ORGANISM: Artificial Sequence
<220> FEATURE:
<223> OTHER INFORMATION: DNA probe

<400> SEQUENCE: 484
ggtggttcgt gttcaccctc cgccg                                          25

<210> SEQ ID NO 485
<211> LENGTH: 25
<212> TYPE: DNA
<213> ORGANISM: Artificial Sequence
<220> FEATURE:
<223> OTHER INFORMATION: DNA probe

<400> SEQUENCE: 485
gtggttcgtg ttcaccctcc gccgg                                          25

<210> SEQ ID NO 486
<211> LENGTH: 25
<212> TYPE: DNA
<213> ORGANISM: Artificial Sequence
<220> FEATURE:
<223> OTHER INFORMATION: DNA probe

<400> SEQUENCE: 486
tggttcgtgt tcaccctccg ccggg                                          25

<210> SEQ ID NO 487
<211> LENGTH: 25
<212> TYPE: DNA
<213> ORGANISM: Artificial Sequence
<220> FEATURE:
<223> OTHER INFORMATION: DNA probe

<400> SEQUENCE: 487
ggttcgtgtt caccctccgc cgggt                                          25

<210> SEQ ID NO 488
<211> LENGTH: 25
<212> TYPE: DNA
<213> ORGANISM: Artificial Sequence
<220> FEATURE:
<223> OTHER INFORMATION: DNA probe

<400> SEQUENCE: 488
gttcgtgttc accctccgcc gggta                                          25

<210> SEQ ID NO 489
<211> LENGTH: 25
<212> TYPE: DNA
<213> ORGANISM: Artificial Sequence
<220> FEATURE:
<223> OTHER INFORMATION: DNA probe

<400> SEQUENCE: 489
ttcgtgttca ccctccgccg ggtac                                          25

<210> SEQ ID NO 490

```
<211> LENGTH: 25
<212> TYPE: DNA
<213> ORGANISM: Artificial Sequence
<220> FEATURE:
<223> OTHER INFORMATION: DNA probe

<400> SEQUENCE: 490
tcgtgttcac cctccgccgg gtaca                                         25

<210> SEQ ID NO 491
<211> LENGTH: 25
<212> TYPE: DNA
<213> ORGANISM: Artificial Sequence
<220> FEATURE:
<223> OTHER INFORMATION: DNA probe

<400> SEQUENCE: 491
cgtgttcacc ctccgccggg tacac                                         25

<210> SEQ ID NO 492
<211> LENGTH: 25
<212> TYPE: DNA
<213> ORGANISM: Artificial Sequence
<220> FEATURE:
<223> OTHER INFORMATION: DNA probe

<400> SEQUENCE: 492
gtgttcaccc tccgccgggt acacc                                         25

<210> SEQ ID NO 493
<211> LENGTH: 25
<212> TYPE: DNA
<213> ORGANISM: Artificial Sequence
<220> FEATURE:
<223> OTHER INFORMATION: DNA probe

<400> SEQUENCE: 493
tgttcaccct ccgccgggta caccg                                         25

<210> SEQ ID NO 494
<211> LENGTH: 25
<212> TYPE: DNA
<213> ORGANISM: Artificial Sequence
<220> FEATURE:
<223> OTHER INFORMATION: DNA probe

<400> SEQUENCE: 494
gttcaccctc cgccgggtac accgc                                         25

<210> SEQ ID NO 495
<211> LENGTH: 25
<212> TYPE: DNA
<213> ORGANISM: Artificial Sequence
<220> FEATURE:
<223> OTHER INFORMATION: DNA probe

<400> SEQUENCE: 495
ttcaccctcc gccgggtaca ccgcc                                         25

<210> SEQ ID NO 496
<211> LENGTH: 25
<212> TYPE: DNA
<213> ORGANISM: Artificial Sequence
<220> FEATURE:
<223> OTHER INFORMATION: DNA probe

<400> SEQUENCE: 496
```
tcaccctccg ccgggtacac cgcct                                            25

<210> SEQ ID NO 497
<211> LENGTH: 25
<212> TYPE: DNA
<213> ORGANISM: Artificial Sequence
<220> FEATURE:
<223> OTHER INFORMATION: DNA probe

<400> SEQUENCE: 497
caccctccgc cgggtacacc gcctc                                            25

<210> SEQ ID NO 498
<211> LENGTH: 25
<212> TYPE: DNA
<213> ORGANISM: Artificial Sequence
<220> FEATURE:
<223> OTHER INFORMATION: DNA probe

<400> SEQUENCE: 498
accctccgcc gggtacaccg cctcg                                            25

<210> SEQ ID NO 499
<211> LENGTH: 25
<212> TYPE: DNA
<213> ORGANISM: Artificial Sequence
<220> FEATURE:
<223> OTHER INFORMATION: DNA probe

<400> SEQUENCE: 499
ccctccgccg ggtacaccgc ctcgt                                            25

<210> SEQ ID NO 500
<211> LENGTH: 25
<212> TYPE: DNA
<213> ORGANISM: Artificial Sequence
<220> FEATURE:
<223> OTHER INFORMATION: DNA probe

<400> SEQUENCE: 500
cctccgccgg gtacaccgcc tcgtc                                            25

<210> SEQ ID NO 501
<211> LENGTH: 25
<212> TYPE: DNA
<213> ORGANISM: Artificial Sequence
<220> FEATURE:
<223> OTHER INFORMATION: DNA probe

<400> SEQUENCE: 501
ctccgccggg tacaccgcct cgtca                                            25

<210> SEQ ID NO 502
<211> LENGTH: 25
<212> TYPE: DNA
<213> ORGANISM: Artificial Sequence
<220> FEATURE:
<223> OTHER INFORMATION: DNA probe

<400> SEQUENCE: 502
tccgccgggt acaccgcctc gtcaa                                            25

<210> SEQ ID NO 503
<211> LENGTH: 25
<212> TYPE: DNA
<213> ORGANISM: Artificial Sequence
<220> FEATURE:

<223> OTHER INFORMATION: DNA probe

<400> SEQUENCE: 503
ccgccgggta caccgcctcg tcaac                                    25

<210> SEQ ID NO 504
<211> LENGTH: 25
<212> TYPE: DNA
<213> ORGANISM: Artificial Sequence
<220> FEATURE:
<223> OTHER INFORMATION: DNA probe

<400> SEQUENCE: 504
cgccgggtac accgcctcgt caact                                    25

<210> SEQ ID NO 505
<211> LENGTH: 25
<212> TYPE: DNA
<213> ORGANISM: Artificial Sequence
<220> FEATURE:
<223> OTHER INFORMATION: DNA probe

<400> SEQUENCE: 505
gccgggtaca ccgcctcgtc aactc                                    25

<210> SEQ ID NO 506
<211> LENGTH: 25
<212> TYPE: DNA
<213> ORGANISM: Artificial Sequence
<220> FEATURE:
<223> OTHER INFORMATION: DNA probe

<400> SEQUENCE: 506
ccgggtacac cgcctcgtca actct                                    25

<210> SEQ ID NO 507
<211> LENGTH: 25
<212> TYPE: DNA
<213> ORGANISM: Artificial Sequence
<220> FEATURE:
<223> OTHER INFORMATION: DNA probe

<400> SEQUENCE: 507
cgggtacacc gcctcgtcaa ctctc                                    25

<210> SEQ ID NO 508
<211> LENGTH: 25
<212> TYPE: DNA
<213> ORGANISM: Artificial Sequence
<220> FEATURE:
<223> OTHER INFORMATION: DNA probe

<400> SEQUENCE: 508
gggtacaccg cctcgtcaac tctcg                                    25

<210> SEQ ID NO 509
<211> LENGTH: 25
<212> TYPE: DNA
<213> ORGANISM: Artificial Sequence
<220> FEATURE:
<223> OTHER INFORMATION: DNA probe

<400> SEQUENCE: 509
ggtacaccgc ctcgtcaact ctcgg                                    25

<210> SEQ ID NO 510

```
<211> LENGTH: 25
<212> TYPE: DNA
<213> ORGANISM: Artificial Sequence
<220> FEATURE:
<223> OTHER INFORMATION: DNA probe

<400> SEQUENCE: 510
gtacaccgcc tcgtcaactc tcgga                                          25

<210> SEQ ID NO 511
<211> LENGTH: 25
<212> TYPE: DNA
<213> ORGANISM: Artificial Sequence
<220> FEATURE:
<223> OTHER INFORMATION: DNA probe

<400> SEQUENCE: 511
tacaccgcct cgtcaactct cggat                                          25

<210> SEQ ID NO 512
<211> LENGTH: 25
<212> TYPE: DNA
<213> ORGANISM: Artificial Sequence
<220> FEATURE:
<223> OTHER INFORMATION: DNA probe

<400> SEQUENCE: 512
acaccgcctc gtcaactctc ggatg                                          25

<210> SEQ ID NO 513
<211> LENGTH: 25
<212> TYPE: DNA
<213> ORGANISM: Artificial Sequence
<220> FEATURE:
<223> OTHER INFORMATION: DNA probe

<400> SEQUENCE: 513
caccgcctcg tcaactctcg gatgg                                          25

<210> SEQ ID NO 514
<211> LENGTH: 25
<212> TYPE: DNA
<213> ORGANISM: Artificial Sequence
<220> FEATURE:
<223> OTHER INFORMATION: DNA probe

<400> SEQUENCE: 514
accgcctcgt caactctcgg atgga                                          25

<210> SEQ ID NO 515
<211> LENGTH: 25
<212> TYPE: DNA
<213> ORGANISM: Artificial Sequence
<220> FEATURE:
<223> OTHER INFORMATION: DNA probe

<400> SEQUENCE: 515
ccgcctcgtc aactctcgga tggac                                          25

<210> SEQ ID NO 516
<211> LENGTH: 25
<212> TYPE: DNA
<213> ORGANISM: Artificial Sequence
<220> FEATURE:
<223> OTHER INFORMATION: DNA probe

<400> SEQUENCE: 516
```
cgcctcgtca actctcggat ggacc                                          25

<210> SEQ ID NO 517
<211> LENGTH: 25
<212> TYPE: DNA
<213> ORGANISM: Artificial Sequence
<220> FEATURE:
<223> OTHER INFORMATION: DNA probe

<400> SEQUENCE: 517
gcctcgtcaa ctctcggatg gacct                                          25

<210> SEQ ID NO 518
<211> LENGTH: 25
<212> TYPE: DNA
<213> ORGANISM: Artificial Sequence
<220> FEATURE:
<223> OTHER INFORMATION: DNA probe

<400> SEQUENCE: 518
cctcgtcaac tctcggatgg acctc                                          25

<210> SEQ ID NO 519
<211> LENGTH: 25
<212> TYPE: DNA
<213> ORGANISM: Artificial Sequence
<220> FEATURE:
<223> OTHER INFORMATION: DNA probe

<400> SEQUENCE: 519
ctcgtcaact ctcggatgga cctcc                                          25

<210> SEQ ID NO 520
<211> LENGTH: 25
<212> TYPE: DNA
<213> ORGANISM: Artificial Sequence
<220> FEATURE:
<223> OTHER INFORMATION: DNA probe

<400> SEQUENCE: 520
tcgtcaactc tcggatggac ctccc                                          25

<210> SEQ ID NO 521
<211> LENGTH: 25
<212> TYPE: DNA
<213> ORGANISM: Artificial Sequence
<220> FEATURE:
<223> OTHER INFORMATION: DNA probe

<400> SEQUENCE: 521
cgtcaactct cggatggacc tcccg                                          25

<210> SEQ ID NO 522
<211> LENGTH: 25
<212> TYPE: DNA
<213> ORGANISM: Artificial Sequence
<220> FEATURE:
<223> OTHER INFORMATION: DNA probe

<400> SEQUENCE: 522
gtcaactctc ggatggacct cccgt                                          25

<210> SEQ ID NO 523
<211> LENGTH: 25
<212> TYPE: DNA
<213> ORGANISM: Artificial Sequence
<220> FEATURE:

```
<223> OTHER INFORMATION: DNA probe

<400> SEQUENCE: 523
tcaactctcg gatggacctc ccgtg                                     25

<210> SEQ ID NO 524
<211> LENGTH: 25
<212> TYPE: DNA
<213> ORGANISM: Artificial Sequence
<220> FEATURE:
<223> OTHER INFORMATION: DNA probe

<400> SEQUENCE: 524
caactctcgg atggacctcc cgtgc                                     25

<210> SEQ ID NO 525
<211> LENGTH: 25
<212> TYPE: DNA
<213> ORGANISM: Artificial Sequence
<220> FEATURE:
<223> OTHER INFORMATION: DNA probe

<400> SEQUENCE: 525
aactctcgga tggacctccc gtgca                                     25

<210> SEQ ID NO 526
<211> LENGTH: 25
<212> TYPE: DNA
<213> ORGANISM: Artificial Sequence
<220> FEATURE:
<223> OTHER INFORMATION: DNA probe

<400> SEQUENCE: 526
actctcggat ggacctcccg tgcac                                     25

<210> SEQ ID NO 527
<211> LENGTH: 25
<212> TYPE: DNA
<213> ORGANISM: Artificial Sequence
<220> FEATURE:
<223> OTHER INFORMATION: DNA probe

<400> SEQUENCE: 527
ctctcggatg gacctcccgt gcacg                                     25

<210> SEQ ID NO 528
<211> LENGTH: 25
<212> TYPE: DNA
<213> ORGANISM: Artificial Sequence
<220> FEATURE:
<223> OTHER INFORMATION: DNA probe

<400> SEQUENCE: 528
tctcggatgg acctcccgtg cacgc                                     25

<210> SEQ ID NO 529
<211> LENGTH: 25
<212> TYPE: DNA
<213> ORGANISM: Artificial Sequence
<220> FEATURE:
<223> OTHER INFORMATION: DNA probe

<400> SEQUENCE: 529
ctcggatgga cctcccgtgc acgca                                     25

<210> SEQ ID NO 530
```

-continued

```
<211> LENGTH: 25
<212> TYPE: DNA
<213> ORGANISM: Artificial Sequence
<220> FEATURE:
<223> OTHER INFORMATION: DNA probe

<400> SEQUENCE: 530
tcggatggac ctcccgtgca cgcac                                        25

<210> SEQ ID NO 531
<211> LENGTH: 25
<212> TYPE: DNA
<213> ORGANISM: Artificial Sequence
<220> FEATURE:
<223> OTHER INFORMATION: DNA probe

<400> SEQUENCE: 531
cggatggacc tcccgtgcac gcacc                                        25

<210> SEQ ID NO 532
<211> LENGTH: 25
<212> TYPE: DNA
<213> ORGANISM: Artificial Sequence
<220> FEATURE:
<223> OTHER INFORMATION: DNA probe

<400> SEQUENCE: 532
ggatggacct cccgtgcacg cacct                                        25

<210> SEQ ID NO 533
<211> LENGTH: 25
<212> TYPE: DNA
<213> ORGANISM: Artificial Sequence
<220> FEATURE:
<223> OTHER INFORMATION: DNA probe

<400> SEQUENCE: 533
gatggacctc ccgtgcacgc acctc                                        25

<210> SEQ ID NO 534
<211> LENGTH: 25
<212> TYPE: DNA
<213> ORGANISM: Artificial Sequence
<220> FEATURE:
<223> OTHER INFORMATION: DNA probe

<400> SEQUENCE: 534
atggacctcc cgtgcacgca cctca                                        25

<210> SEQ ID NO 535
<211> LENGTH: 25
<212> TYPE: DNA
<213> ORGANISM: Artificial Sequence
<220> FEATURE:
<223> OTHER INFORMATION: DNA probe

<400> SEQUENCE: 535
tggacctccc gtgcacgcac ctcac                                        25

<210> SEQ ID NO 536
<211> LENGTH: 25
<212> TYPE: DNA
<213> ORGANISM: Artificial Sequence
<220> FEATURE:
<223> OTHER INFORMATION: DNA probe

<400> SEQUENCE: 536
```
ggacctcccg tgcacgcacc tcacc                                    25

<210> SEQ ID NO 537
<211> LENGTH: 25
<212> TYPE: DNA
<213> ORGANISM: Artificial Sequence
<220> FEATURE:
<223> OTHER INFORMATION: DNA probe

<400> SEQUENCE: 537
gacctcccgt gcacgcacct caccg                                    25

<210> SEQ ID NO 538
<211> LENGTH: 25
<212> TYPE: DNA
<213> ORGANISM: Artificial Sequence
<220> FEATURE:
<223> OTHER INFORMATION: DNA probe

<400> SEQUENCE: 538
acctcccgtg cacgcacctc accga                                    25

<210> SEQ ID NO 539
<211> LENGTH: 25
<212> TYPE: DNA
<213> ORGANISM: Artificial Sequence
<220> FEATURE:
<223> OTHER INFORMATION: DNA probe

<400> SEQUENCE: 539
cctcccgtgc acgcacctca ccgag                                    25

<210> SEQ ID NO 540
<211> LENGTH: 25
<212> TYPE: DNA
<213> ORGANISM: Artificial Sequence
<220> FEATURE:
<223> OTHER INFORMATION: DNA probe

<400> SEQUENCE: 540
ctcccgtgca cgcacctcac cgagg                                    25

<210> SEQ ID NO 541
<211> LENGTH: 25
<212> TYPE: DNA
<213> ORGANISM: Artificial Sequence
<220> FEATURE:
<223> OTHER INFORMATION: DNA probe

<400> SEQUENCE: 541
tcccgtgcac gcacctcacc gaggc                                    25

<210> SEQ ID NO 542
<211> LENGTH: 25
<212> TYPE: DNA
<213> ORGANISM: Artificial Sequence
<220> FEATURE:
<223> OTHER INFORMATION: DNA probe

<400> SEQUENCE: 542
cccgtgcacg cacctcaccg aggcg                                    25

<210> SEQ ID NO 543
<211> LENGTH: 25
<212> TYPE: DNA
<213> ORGANISM: Artificial Sequence
<220> FEATURE:

<223> OTHER INFORMATION: DNA probe

<400> SEQUENCE: 543
ccgtgcacgc acctcaccga ggcgt        25

<210> SEQ ID NO 544
<211> LENGTH: 25
<212> TYPE: DNA
<213> ORGANISM: Artificial Sequence
<220> FEATURE:
<223> OTHER INFORMATION: DNA probe

<400> SEQUENCE: 544
cgtgcacgca cctcaccgag gcgtc        25

<210> SEQ ID NO 545
<211> LENGTH: 25
<212> TYPE: DNA
<213> ORGANISM: Artificial Sequence
<220> FEATURE:
<223> OTHER INFORMATION: DNA probe

<400> SEQUENCE: 545
gtgcacgcac ctcaccgagg cgtct        25

<210> SEQ ID NO 546
<211> LENGTH: 25
<212> TYPE: DNA
<213> ORGANISM: Artificial Sequence
<220> FEATURE:
<223> OTHER INFORMATION: DNA probe

<400> SEQUENCE: 546
tgcacgcacc tcaccgaggc gtcta        25

<210> SEQ ID NO 547
<211> LENGTH: 25
<212> TYPE: DNA
<213> ORGANISM: Artificial Sequence
<220> FEATURE:
<223> OTHER INFORMATION: DNA probe

<400> SEQUENCE: 547
gcacgcacct caccgaggcg tctat        25

<210> SEQ ID NO 548
<211> LENGTH: 25
<212> TYPE: DNA
<213> ORGANISM: Artificial Sequence
<220> FEATURE:
<223> OTHER INFORMATION: DNA probe

<400> SEQUENCE: 548
cacgcacctc accgaggcgt ctatg        25

<210> SEQ ID NO 549
<211> LENGTH: 25
<212> TYPE: DNA
<213> ORGANISM: Artificial Sequence
<220> FEATURE:
<223> OTHER INFORMATION: DNA probe

<400> SEQUENCE: 549
acgcacctca ccgaggcgtc tatgg        25

<210> SEQ ID NO 550

```
<211> LENGTH: 25
<212> TYPE: DNA
<213> ORGANISM: Artificial Sequence
<220> FEATURE:
<223> OTHER INFORMATION: DNA probe

<400> SEQUENCE: 550
cgcacctcac cgaggcgtct atgga                                          25

<210> SEQ ID NO 551
<211> LENGTH: 25
<212> TYPE: DNA
<213> ORGANISM: Artificial Sequence
<220> FEATURE:
<223> OTHER INFORMATION: DNA probe

<400> SEQUENCE: 551
gcacctcacc gaggcgtcta tggac                                          25

<210> SEQ ID NO 552
<211> LENGTH: 25
<212> TYPE: DNA
<213> ORGANISM: Artificial Sequence
<220> FEATURE:
<223> OTHER INFORMATION: DNA probe

<400> SEQUENCE: 552
cacctcaccg aggcgtctat ggacc                                          25

<210> SEQ ID NO 553
<211> LENGTH: 25
<212> TYPE: DNA
<213> ORGANISM: Artificial Sequence
<220> FEATURE:
<223> OTHER INFORMATION: DNA probe

<400> SEQUENCE: 553
acctcaccga ggcgtctatg gacct                                          25

<210> SEQ ID NO 554
<211> LENGTH: 25
<212> TYPE: DNA
<213> ORGANISM: Artificial Sequence
<220> FEATURE:
<223> OTHER INFORMATION: DNA probe

<400> SEQUENCE: 554
cctcaccgag gcgtctatgg acctc                                          25

<210> SEQ ID NO 555
<211> LENGTH: 25
<212> TYPE: DNA
<213> ORGANISM: Artificial Sequence
<220> FEATURE:
<223> OTHER INFORMATION: DNA probe

<400> SEQUENCE: 555
ctcaccgagg cgtctatgga cctct                                          25

<210> SEQ ID NO 556
<211> LENGTH: 25
<212> TYPE: DNA
<213> ORGANISM: Artificial Sequence
<220> FEATURE:
<223> OTHER INFORMATION: DNA probe

<400> SEQUENCE: 556
```
tcaccgaggc gtctatggac ctctt                                     25

<210> SEQ ID NO 557
<211> LENGTH: 25
<212> TYPE: DNA
<213> ORGANISM: Artificial Sequence
<220> FEATURE:
<223> OTHER INFORMATION: DNA probe

<400> SEQUENCE: 557
caccgaggcg tctatggacc tcttg                                     25

<210> SEQ ID NO 558
<211> LENGTH: 25
<212> TYPE: DNA
<213> ORGANISM: Artificial Sequence
<220> FEATURE:
<223> OTHER INFORMATION: DNA probe

<400> SEQUENCE: 558
accgaggcgt ctatggacct cttgc                                     25

<210> SEQ ID NO 559
<211> LENGTH: 25
<212> TYPE: DNA
<213> ORGANISM: Artificial Sequence
<220> FEATURE:
<223> OTHER INFORMATION: DNA probe

<400> SEQUENCE: 559
ccgaggcgtc tatggacctc ttgcc                                     25

<210> SEQ ID NO 560
<211> LENGTH: 25
<212> TYPE: DNA
<213> ORGANISM: Artificial Sequence
<220> FEATURE:
<223> OTHER INFORMATION: DNA probe

<400> SEQUENCE: 560
cgaggcgtct atggacctct tgccc                                     25

<210> SEQ ID NO 561
<211> LENGTH: 25
<212> TYPE: DNA
<213> ORGANISM: Artificial Sequence
<220> FEATURE:
<223> OTHER INFORMATION: DNA probe

<400> SEQUENCE: 561
gaggcgtcta tggacctctt gccct                                     25

<210> SEQ ID NO 562
<211> LENGTH: 25
<212> TYPE: DNA
<213> ORGANISM: Artificial Sequence
<220> FEATURE:
<223> OTHER INFORMATION: DNA probe

<400> SEQUENCE: 562
aggcgtctat ggacctcttg ccctt                                     25

<210> SEQ ID NO 563
<211> LENGTH: 25
<212> TYPE: DNA
<213> ORGANISM: Artificial Sequence
<220> FEATURE:

<223> OTHER INFORMATION: DNA probe

<400> SEQUENCE: 563
ggcgtctatg gacctcttgc ccttc　　25

<210> SEQ ID NO 564
<211> LENGTH: 25
<212> TYPE: DNA
<213> ORGANISM: Artificial Sequence
<220> FEATURE:
<223> OTHER INFORMATION: DNA probe

<400> SEQUENCE: 564
gcgtctatgg acctcttgcc cttcc　　25

<210> SEQ ID NO 565
<211> LENGTH: 25
<212> TYPE: DNA
<213> ORGANISM: Artificial Sequence
<220> FEATURE:
<223> OTHER INFORMATION: DNA probe

<400> SEQUENCE: 565
cgtctatgga cctcttgccc ttcct　　25

<210> SEQ ID NO 566
<211> LENGTH: 25
<212> TYPE: DNA
<213> ORGANISM: Artificial Sequence
<220> FEATURE:
<223> OTHER INFORMATION: DNA probe

<400> SEQUENCE: 566
gtctatggac ctcttgccct tcctc　　25

<210> SEQ ID NO 567
<211> LENGTH: 25
<212> TYPE: DNA
<213> ORGANISM: Artificial Sequence
<220> FEATURE:
<223> OTHER INFORMATION: DNA probe

<400> SEQUENCE: 567
tctatggacc tcttgccctt cctct　　25

<210> SEQ ID NO 568
<211> LENGTH: 25
<212> TYPE: DNA
<213> ORGANISM: Artificial Sequence
<220> FEATURE:
<223> OTHER INFORMATION: DNA probe

<400> SEQUENCE: 568
ctatggacct cttgcccttc ctctg　　25

<210> SEQ ID NO 569
<211> LENGTH: 25
<212> TYPE: DNA
<213> ORGANISM: Artificial Sequence
<220> FEATURE:
<223> OTHER INFORMATION: DNA probe

<400> SEQUENCE: 569
tatggacctc ttgcccttcc tctgc　　25

<210> SEQ ID NO 570

```
<211> LENGTH: 25
<212> TYPE: DNA
<213> ORGANISM: Artificial Sequence
<220> FEATURE:
<223> OTHER INFORMATION: DNA probe

<400> SEQUENCE: 570
atggacctct tgcccttcct ctgcg                                         25

<210> SEQ ID NO 571
<211> LENGTH: 25
<212> TYPE: DNA
<213> ORGANISM: Artificial Sequence
<220> FEATURE:
<223> OTHER INFORMATION: DNA probe

<400> SEQUENCE: 571
tggacctctt gcccttcctc tgcga                                         25

<210> SEQ ID NO 572
<211> LENGTH: 25
<212> TYPE: DNA
<213> ORGANISM: Artificial Sequence
<220> FEATURE:
<223> OTHER INFORMATION: DNA probe

<400> SEQUENCE: 572
ggacctcttg cccttcctct gcgac                                         25

<210> SEQ ID NO 573
<211> LENGTH: 25
<212> TYPE: DNA
<213> ORGANISM: Artificial Sequence
<220> FEATURE:
<223> OTHER INFORMATION: DNA probe

<400> SEQUENCE: 573
gacctcttgc ccttcctctg cgacg                                         25

<210> SEQ ID NO 574
<211> LENGTH: 25
<212> TYPE: DNA
<213> ORGANISM: Artificial Sequence
<220> FEATURE:
<223> OTHER INFORMATION: DNA probe

<400> SEQUENCE: 574
acctcttgcc cttcctctgc gacgt                                         25

<210> SEQ ID NO 575
<211> LENGTH: 25
<212> TYPE: DNA
<213> ORGANISM: Artificial Sequence
<220> FEATURE:
<223> OTHER INFORMATION: DNA probe

<400> SEQUENCE: 575
cctcttgccc ttcctctgcg acgtc                                         25

<210> SEQ ID NO 576
<211> LENGTH: 25
<212> TYPE: DNA
<213> ORGANISM: Artificial Sequence
<220> FEATURE:
<223> OTHER INFORMATION: DNA probe

<400> SEQUENCE: 576
```
ctcttgccct tcctctgcga cgtcg					25

<210> SEQ ID NO 577
<211> LENGTH: 25
<212> TYPE: DNA
<213> ORGANISM: Artificial Sequence
<220> FEATURE:
<223> OTHER INFORMATION: DNA probe

<400> SEQUENCE: 577
tcttgccctt cctctgcgac gtcgc					25

<210> SEQ ID NO 578
<211> LENGTH: 25
<212> TYPE: DNA
<213> ORGANISM: Artificial Sequence
<220> FEATURE:
<223> OTHER INFORMATION: DNA probe

<400> SEQUENCE: 578 cttgccctt c ctctgcgacg tcgcg					25

<210> SEQ ID NO 579
<211> LENGTH: 25
<212> TYPE: DNA
<213> ORGANISM: Artificial Sequence
<220> FEATURE:
<223> OTHER INFORMATION: DNA probe

<400> SEQUENCE: 579 ttgccctt cc tctgcgacgt cgcgt					25

<210> SEQ ID NO 580
<211> LENGTH: 25
<212> TYPE: DNA
<213> ORGANISM: Artificial Sequence
<220> FEATURE:
<223> OTHER INFORMATION: DNA probe

<400> SEQUENCE: 580
tgcccttcct ctgcgacgtc gcgtg					25

<210> SEQ ID NO 581
<211> LENGTH: 25
<212> TYPE: DNA
<213> ORGANISM: Artificial Sequence
<220> FEATURE:
<223> OTHER INFORMATION: DNA probe

<400> SEQUENCE: 581
gcccttcctc tgcgacgtcg cgtgc					25

<210> SEQ ID NO 582
<211> LENGTH: 25
<212> TYPE: DNA
<213> ORGANISM: Artificial Sequence
<220> FEATURE:
<223> OTHER INFORMATION: DNA probe

<400> SEQUENCE: 582
cccttcctct gcgacgtcgc gtgcc					25

US 8,343,720 B2

METHODS AND PROBES FOR IDENTIFYING A NUCLEOTIDE SEQUENCE

This application is a Continuation application that claims priority under 35 U.S.C. §120 of U.S. application Ser. No. 12/001,027 filed on Dec. 7, 2007, now abandoned; and application Ser. No. 12/001,027 is a Continuation-in-Part of the National Phase under 35 U.S.C. §371 of International Application No. PCT/AU2006/001740 filed in Australia on Nov. 21, 2006, which claims priority to U.S. Provisional Application No. 60/738,019 filed on Nov. 21, 2005.

FIELD OF THE INVENTION

The present invention is directed to the field of molecular biology. More specifically the invention is directed to methods for generating oligonucleotide probes and uses thereof in identifying members of a group of related nucleotide sequences. The methods and probes may be used in identifying an allele of a gene in an individual.

BACKGROUND TO THE INVENTION

The Human Genome Project has highlighted the importance of single nucleotide polymorphisms (SNPs) in the genome. These polymorphisms occur on average every 100 to 300 bases throughout the genome. While the genes of all humans are known to be more than 99% identical, it is presence of SNPs that provide a major component of genetic diversity in a species. Different alleles of a gene can confer very different phenotypes on an individual including characteristics as diverse as disease resistance, the ability to respond to a pharmaceutical compound, sporting ability and the like.

Plant genomes also contain SNPs that can result in different characteristics. SNPs are increasingly becoming the marker of choice in genetic analysis and are used routinely as markers in agricultural breeding programs. SNPs cannot only be used to link a particular genotype to phenotype. They can also be used as a "fingerprint" in identifying organisms as diverse as bacteria, viruses and the like.

The ability to ascribe a genotype to an individual is of significance for a number of reasons. As a broad concept this involves identification of a nucleotide sequence of a subject gene of the organism involved. The most direct manner of providing this information is to sequence the subject gene. While automated sequencing has been possible for some years, the process is still time intensive and expensive.

As a result of the limitations to the widespread use of direct sequencing, a number of indirect methods have been advanced to identify alleles. One of the simplest is the use of Restriction Fragment Length Polymorphism (RFLP). This approach relies on the specificity of restriction endonucleases for certain nucleotide sequences. Thus, if a certain sequence is present, the endonuclease will cleave the polynucleotide, and if not no cleavage will result. Different genotypes are detected by the different pattern of restriction fragments, as detected by gel electrophoresis. The disadvantage of this method is that where there is no endonuclease specific for each and every SNP in the range of alleles, then all alleles will not be identifiable by RFLP. This is often the case, and so use of RFLP is significantly limited.

Another method to detect an allele involves the use of an oligonucleotide probe that binds specifically to sequences found in one allele, but not to other alleles. Binding of the probe to a target allele may be detected by the use of tags such as fluorescent compounds or radioisotopes. A problem of oligonucleotide probe-based methods is that to definitively ascribe a genotype it may be necessary to use a very large number of probes. Since the biophysics of polynucleotide hybridization dictate that probe length is limited (typically no more than about 65 nucleotides), where the subject gene is longer than the maximum probe length a series of different probes must be designed to cover the entire length of the gene. The number of different probes escalates greatly where the subject gene has a large number of alleles, a large number of SNPs, where the density of SNPs is high, or a combination of any of these factors.

An example of a problem in the art is the human leukocyte antigen HLA-DRB locus that is often analysed in tissue typing for organ transplantation. The locus currently has 483 identified alleles, and there are 270 nucleotides in the variable 2nd exon. Simple multiplication produces 130,410 different nucleotide sequence variations for probes that would be required to resolve a genotype at this locus. Generating such a large number of different oligonucleotide probes, and then assessing the ability of each probe to hybridise to a test sample, is clearly a significant burden. Furthermore, previously unrecognised alleles continue to be discovered thereby exacerbating the problem of providing a probe set capable of resolving an individual's HLA type.

The problems inherent in using large numbers of probes has been partially overcome by advances in solid-phase technologies that allow binding of many thousands of probes to "chips" to form a "microarray". However, microarray technology still requires the use of many probes to identify all alleles of a gene and simply provides a more convenient format for handling large probe sets. Current probes for SNP detection are directed to physically separate regions of the target DNA molecule, and often selected where the sequence flanking the SNP is monomorphic. Use of probes such as this is known in the art as "resequencing".

Resequencing relies on the use of specifically designed probes capable of identifying all possible SNPs. Guo et al (2002, Genome Research 12:447-457) address the problem of providing probes for HLA-typing by making 20-mer probes, with each probe designed to represent particular combinations of SNPs, rather than a single SNP. A problem with this approach is that it is not systematic, and it is necessary for a human to judiciously design the probes. Given the real possibility of error in this process it remains an uncertainty whether the probe set will identify all alleles at the end of the probe design process.

A further problem with the method provided by Guo et al is that it is necessary to include SNP sites over the length of the probe. Consideration of Table 1 of Guo et al shows that polymorphic sites are present from the 5' end to the 3' end of the 20-mer probes. It is known in the art that the accuracy of hybridization diminishes toward the flanks of a probe, and so it would be expected that there will be inaccuracies in the hybridization reactions using the method of Guo et al. Of particular note the probe set designed by Guo et al resulted in 32 false positive reactions among 100 hybridizations.

Accordingly, it is an aspect of the present invention to overcome or alleviate a problem of the prior art by providing a systematic method for designing probe sets capable of robustly identifying all known polymorphisms in a nucleotide sequence.

The discussion of documents, acts, materials, devices, articles and the like is included in this specification solely for the purpose of providing a context for the present invention. It is not suggested or represented that any or all of these matters formed part of the prior art base or were common general

SUMMARY OF THE INVENTION

In a first aspect the present invention provides a method for identifying a set of target nucleotide sequences capable of identifying a member of a group of related nucleotide sequences, the method comprising the step of dividing the nucleotide sequence of each member of the group into a plurality of subsequences, wherein at least two of the subsequences overlap. Applicants have found that it is possible to identify a set of target nucleotide sequences useful as targets for hybridization with oligonucleotide probes by dividing the sequences under consideration into overlapping subsequences. Preferably, at least one of the subsequences overlaps with more than one other subsequence. More preferably, at least one of the subsequences overlaps with more than 2, 3, 4 or 5 other subsequences.

Advantageously, the method is amenable to automation and is proposed to be useful for providing probes capable of resolving genes having a high number of alleles and/or a high density of SNPs such as those of the major histocompatability complex (MHC), the T-cell receptor, the B-cell receptor, immunoglobulins, the killer inhibitory receptor (KIR), and the like.

In one embodiment of the method, the number of probes required for the application can be significantly reduced by identifying redundant probes, and removing or not including the redundant probes in the probe set. It has not been appreciated in the art that when analyzing related sequences for the purposes of designing a set of oligonucleotide probes, a polymorphism in one member sequence is not necessarily present in another member sequence. Accordingly, it is unnecessary to provide probes covering every combination of every polymorphism, since not all combinations necessarily exist in the group of related sequences.

In another embodiment of the method, one or more of the subsequences (and any probes derived from the subsequences) does not contain one or more polymorphic sites at, or toward, the 5' and/or 3' ends of the one or more subsequences. In another embodiment of the method one or more of the subsequences contains one or more polymorphic sites at, or toward, the center of the one or more subsequences. The avoidance of polymorphic sites toward the flanks of the probe, and concentrating the sites to the centre of the probe overcomes the problem of probes provide by Guo et al (2002) that apparently bind inaccurately such that a large number of false positive hybridization reactions are generated.

In another aspect the present invention provides a set of probes capable of specifically hybridizing to target nucleotide sequences identified by the methods described herein. Preferably, the probes are directed to multi-exon coverage and are capable of providing total allele assignment.

In another aspect the present invention provides a method of identifying and/or recovering a member of a group of related nucleotide sequences using a set of probes as described herein. The method will typically utilise probes immobilised on microarray chip.

In another aspect the present invention provides a computer executable program (software) capable of executing the methods described herein.

BRIEF DESCRIPTION OF THE FIGURES

FIG. 1 shows hypothetical application of the method of selecting a probe set. In this case, there are three related 19-mer sequences (#1, #2 and #3). Taking the first nucleotide in the exon as 1 (i.e. the 5$^{th}$ nucleotide in), the exon has two SNPs at positions 6 and 11 (underlined). FIG. 1A shows the related sequences divided into 9-mer subsequences, with complete overlap between the subsequences. FIG. 1B shows all subsequences pooled from related sequences #1, #2 and #3. FIG. 1C shows the set of subsequences from FIG. 1B after removal of redundant subsequences. It is emphasized that this hypothetical example does not necessarily show all the advantages of the invention, but is intended to demonstrate only the operation of a preferred form the method.

FIG. 2 shows probe sequences identified by the present invention for assignment of HLA-A*0201 (exons 2 and 3). A 25-mer probe length was chosen, with maximal overlap between probes.

DETAILED DESCRIPTION OF THE INVENTION

Applicants propose a systematic method for designing probes capable of identifying the member of a group of related nucleotide sequences. Accordingly, in a first aspect the present invention provides a method for identifying a set of target nucleotide sequences capable of identifying a member of a group of related nucleotide sequences, the method comprising the step of dividing the nucleotide sequence of each member of the group into a plurality of subsequences, wherein at least two of the subsequences overlap.

Applicants have found that it is possible to identify a set of target nucleotide sequences useful for hybridization with oligonucleotide probes by dividing the sequence under consideration into overlapping subsequences. Thus, the related group of subsequences may cover a particular locus, with each member of the related group having a different nucleotide sequence. In one form of the present method, each member of the group of related sequences is divided into a number of subsequences. Within a given member sequence, the subsequences overlap each other such that a potentially large number of subsequences may be generated. This approach is clearly distinguished from methods of the prior art that are based on the use of consecutive subsequences.

Preferably, at least one of the subsequences overlaps with more than one other subsequence. More preferably, at least one of the subsequences overlaps with more than 2, 3, 4 or 5 other subsequences.

The degree of overlap used to generate the series of overlapping probe-length subsequences may be the minimum possible. An example of minimum overlap for a series of 25-mer subsequences would be where the first subsequence covers nucleotides 1 to 25, the second subsequence covers nucleotides 25 to 50, the third subsequence covers nucleotides 50 to 75, et cetera.

The overlap may be the maximum degree of overlap possible. An example for a series of 25-mer subsequences having the maximum possible overlap would be where the first subsequence covers nucleotides 1 to 25, the second subsequence covers nucleotides 2 to 26, the third subsequence covers nucleotides 3 to 27, et cetera.

The invention includes any intermediate degree of overlap between the minimum and maximum available. However, the use of substantially maximum overlap is preferred since this requires the least amount of judgement on the part of the individual designing the probe set. The higher the degree of overlap used, the greater the ability to cover more combinations of SNPs present in the related sequences.

It is not necessary for the amount of overlap to be fixed for the use of the method with any given member of the group. It is also not necessary for the length of the subsequence to be fixed. It will be possible for the skilled person to routinely investigate the effects of varying subsequence lengths and degree of overlap between the subsequences to ascertain whether any advantage is gained.

It will be understood that where a high degree of overlap is used, a very large number of subsequences will be generated. Accordingly, a very large number of probes will be included in the probe set. While microarray chips are able to carry large numbers of probes, for economic reasons at least it is desirable to limit the number of probes required for a given analysis. In one embodiment of the method, the number of probes required for the application can be significantly reduced by identifying redundant probes, and removing or not including the redundant probes in the probe set. It has not been appreciated in the art that when analyzing related sequences for the purposes of designing a set of oligonucleotide probes, a polymorphism in one member sequence is not necessarily present in another member sequence. Accordingly, it is unnecessary to provide probes covering every combination of every polymorphism, since not all combinations necessarily exist in the group of related sequences. This approach is especially useful where the related sequences are highly polymorphic, and the present state of the art predicts that a larger-than-necessary number of probes are required to identify all theoretical members of the group. Thus, in a preferred embodiment, the method includes the step of analyzing at least a portion of the subsequences for redundancy and removing at least a proportion of any subsequences identified as redundant.

Decreasing the level of redundancy may be achieved using a subtractive approach by, for example, assuming that all polymorphisms are present in all members of the group, and generating a plurality of subsequences based on that assumption. Subsequently, the plurality of subsequences is analyzed for the presence of redundant sequences, which are then removed to leave the set of unique target nucleotide sequences. It will be appreciated that the set of target nucleotide subsequences has the same capability of identifying every member of the group as the larger set of subsequences that are generated on the assumption that all polymorphisms are present in all members.

Alternatively, an additive method may be used where the plurality of probe-length sequences is incrementally generated, one by one, with each newly generated subsequence being analyzed for redundancy in light of all previously generated subsequences. If a newly generated subsequence is found to be redundant it is not added to the set of target nucleotide sequences, otherwise it is included in the set of target nucleotide sequences. Whether an additive or subtractive method is used, the end result is the same: a set of subsequences having no redundancy, or a reduced level of redundancy, is generated that is capable of identifying all members of the group of related sequences.

It is desirable to limit the number of probes required to identify a member sequence for a number of reasons. The cost of synthesizing probes and producing microarray chips to carry those probes is a significant consideration in the economic viability of implementing a method for identifying a nucleotide sequence. This is the case whether it is for purely research purposes, or for a high throughput commercial application such as in a pathology laboratory. Particularly, where a nucleotide sequence can have many alternative forms (i.e. where the number of members in the group of related sequences is high), the prior art methods require a commensurately high number of different specific probes. Thus, to screen for the presence of a single member nucleotide sequence it may be necessary to use hundreds, or even thousands of individual probes depending on the length of the sequence to be interrogated.

Another reason for limiting the number of probes necessary for identifying a member nucleotide sequence relates to the practical limits of certain probe hybridization methods. For example, a standard dot blot apparatus may have only 64 wells for sample application, thereby restricting the user to only 64 different probes, and therefore the ability to identify only 64 different nucleotide sequences per run. A further example is where a microarray system is used to identify a very large number of alternative forms of a nucleotide sequence. At present, a standard microarray chip can hold up to 500,000 different oligonucleotide probes. While this may appear to be ample, for some applications this number is insufficient and it would be necessary to prepare multiple chips to accommodate all probes.

In one embodiment of the method, one or more of the subsequences (and any probes derived from the subsequences) does not contain one or more polymorphic sites at, or toward, the 5' and/or 3' ends of the one or more subsequences. In another embodiment of the method one or more of the subsequences contains one or more polymorphic sites at, or toward, the center of the one or more subsequences. The avoidance of polymorphic sites toward the flanks of the probe, and concentrating the sites to the centre of the probe overcomes the problem of probes provide by Guo et al (2002) that apparently bind inaccurately such that a large number of false positive hybridization reactions are generated.

The related nucleic acid sequences can be genomic, RNA, cDNA, or cRNA. Genomic DNA samples are usually subject to amplification before application to an array using primers flanking the region of interest. Genomic DNA can be obtained from virtually any tissue source (other than pure red blood cells). For example, convenient tissue samples include-whole blood, semen, saliva, tears, urine, fecal material, sweat, buccal, skin and hair. Amplification of genomic DNA containing a polymorphic site generates a single species of target nucleic acid if the individual from the sample was obtained is homozygous at the polymorphic site or two species of target molecules if the individual is heterozygous.

The DNA may be prepared for analysis by any suitable method known to the skilled artisan, including by PCR using appropriate primers. Where it is desired to analyze the entire genome, the method of whole genome amplification (WGA) may be used. Commercial kits are readily available for this method including the GenoPlex® Complete WGA kit manufactured by Sigma-Aldrich Corp (St Louis, Mo., USA). This kit is based upon random fragmentation of the genome into a series templates. The resulting shorter DNA strands generate a library of DNA fragments with defined 3 primed and 5 primed termini. The library is replicated using a linear, isothermal amplification in the initial stages, followed by a limited round of geometric (PCR) amplifications. WGA methods are suitable for use with purified genomic DNA from a variety of sources including blood cards, whole blood, buccal swabs, soil, plant, and formalin-fixed paraffin-embedded tissues.

mRNA samples are also often subject to amplification. In this case amplification is typically preceded by reverse transcription. Amplification of all expressed mRNA can be performed as described in WO 96/14839 and WO 97/01603. Amplification of an RNA sample from a diploid sample can generate two species of target molecule if the individual from whom the sample was obtained is heterozygous at a polymorphic site occurring within expressed mRNA.

As will be apparent, the nucleotide subsequences identified by the method may be subsequently used to design a probe set capable of identifying all currently identified members of the group of related sequences. As used herein the term "target nucleotide sequence" means a sequence against which a substantially specific probe may be generated. The generation of probes is discussed further infra, however the probe is typically an oligonucleotide probe capable of hybridizing to the target nucleotide sequence.

Applicants have found that even where the group of related sequences has a large number of members, and/or where the members have a large number of polymorphic bases, and/or where the polymorphic bases have more than two alternative forms, it is possible to produce a probe set capable of definitively identifying any member of the group using a number of probes significantly less than that previously considered in the art to be necessary. The method may be used, for example, to produce a probe set capable of identifying any given allele of a gene locus, and is especially useful where the number of alleles is very high. By contrast, Guo et al (2002) do not disclose a practical and robust method for designing probes for multi-exon coverage capable of providing total allele assignment.

The skilled person will understand that the length of the probe-length subsequences may be any length that provides the ability to discriminate between the members of the group of related sequences.

Probes used for microarray applications are typically about 25 nucleotides in length, however longer and shorter probes are contemplated to be useful in the context of the invention. A lower useful length may be determined by the need for sufficient nucleotides to provide specificity of binding, and may be from about 10 nucleotides to about 15 nucleotides. Probes of a less than 15 nucleotides could be contemplated where a "sub-genome" is under test. An example of this is where single haploid chromosomes are under test, and sequence detection specificity does not require a probe length needed to analyze the approximately 3 billion nucleotides in the entire genome of a human. The upper limit may be determined by physical constraints relating to the need to melt double-stranded regions and anneal single strands of polynucleotide. This may be from about 30 to about 50 nucleotides. The upper limit may vary according to the proportion of C/G bases given the higher melting temperatures needed to separate these bases in a duplex, as compared with an NT pairing. While there may be practical upper and lower limits for the length of probe, these limits will vary according to the specifics of the application and the skilled person will be able to identify the probe of most appropriate length by routine empirical experimentation.

It will be understood that the method may be applied to any situation where it is necessary to discriminate between a number of related nucleotide sequences. As used herein, the term "nucleotide sequence" and variations thereof is intended to include deoxyribonucleic acid (DNA) and ribonucleic acid (RNA) sequences. The related nucleotide sequences may be any group of nucleotide sequences that exhibit a minimum level of sequence identity. Preferably the sequences have an identity of at least 50%, 60%, 70%, 80%, 90%, 95% or 99%. The identity may be even higher than 99% where, for example, the related sequences are long, and there are a series of SNPs scattered throughout.

The related sequences may be protein coding, non-protein coding, or a combination of protein coding and non-protein coding.

The related sequences may be derived from diploid, haploid, triploid or polyploid material, or provide information on the diploid, haploid, triploid or polyploid state.

Where information is sought on the haploid state, the present methods are useful for providing probes that can provide definitive DNA allele assignment to haplotype stratification. The concept of locus allelism is known in the art, however it has not previously been appreciated that allelism of loci that bound regions, including alleles that involve synonymous changes, are contributory to haplotype stratification. Thus, probes for genomic (diploid) DNA can inform about haplotypic (cis phase) multi-allele assignment. Specifically, synonymous alleles are a unit in multilocus chromosomal haplotypic segment. Probes generated by the methods described herein that characterise locus allelism contribute to revelation of patterns of multilocus co-allelism, which is haplotypy. This concept is exemplified by telomeric G and F loci. There are 23 alleles at HLA-G and 20 at HLA-F. These 43, combined with the 120 at centromeric DPB1 locus, as well as those many in between will assist in assigning the finite multi-locus allelic variations as haplotypes spanning the <4 Mb MHC region.

The related sequences may be natural or synthetic. They may be from any organism including an animal, plant, microorganism, bacterium, or virus.

In one form of the invention, the related sequences are directed to the same region of the genome. For example, the region from the first nucleotide of an exon to the last nucleotide of the exon. In this case, and where a 25-mer probe is to be used, the probe may be designed such that the $13^{th}$ nucleotide of the probe (i.e. the central nucleotide) is directed to the first nucleotide of the exon. Thus, where the first nucleotide is G, the $13^{th}$ nucleotide of the probe will be C. It will be apparent that the flanking 12-mer regions of the probe will be directed in one case to the pre-exon region and in the other case, further into the exon.

The general operation of one embodiment of the method can be demonstrated by consideration of the greatly simplified example shown in FIG. 1. This demonstration is directed to 3 related nucleotide sequences (#1, #2 and #3), with the exon starting at the $5^{th}$ nucleotide in from the left hand or 5' end (i.e. A). Taking the first nucleotide in the exon as 1, the exon has two SNPs at positions 6 and 11 (underlined). Subsequences of 9 nucleotides were used, with there being complete overlap in the subsequences. Thus, the first subsequence commences at position −4 and terminates at position +5.

As will be apparent from FIG. 1A, each related sequence is divided into 11, 9-mer subsequences. This provides a total of 33 subsequences (FIG. 1B). Duplicate subsequences are removed to leave 17 unique subsequences (FIG. 1C). The skilled person will understand that the probe sequences do not need to be complimentary if the original target molecule was a double-stranded molecule. In that case, the nucleotide sequence can be directly used as the probe sequence or complimented to ACAGGGGTGTCGTGCAAAGAACCTC, (SEQ ID NO:1) depending on the target generation strategy chosen by the skilled artisan. Thus, the probe can be directed to either strand, or both, on the array if dsDNA is used in final target generation).

It should be appreciated that this example is provided simply to demonstrate the steps required to generate a probe set capable of distinguishing the members of a group of related nucleotide sequences according to one form of the present invention. In this case, a reduction in probe number of about 50% is achieved. In more complex systems, the reduction in probe number will be significantly greater, possibly in excess of 95%.

The methods of the present invention will allow analysis of many variations in nucleotide sequences including deletions, substitutions, additions and the like. In one form of the invention the related nucleotide sequences are identical except for the presence of SNPs.

While the SNPs may be present at any density, the methods provide greater advantages where the SNPs are present at a high density. Preferably the density is such that two or more SNPs are present within a probe length region of the nucleotide sequence. The ability to distinguish related nucleotide sequences that include SNPs at high density has previously been problematic since it has hitherto been thought necessary to provide a large number of probes to cover every combination of SNPs in a given region. This has especially been an issue in designing probe sets for HLA typing where 20% to 50% of the nucleotides in HLA exons are polymorphic, and often the polymorphic sites are clustered. This has resulted in the prior art predicting that a practically infeasible number of different probes would be required to definitively ascribe an HLA type to an individual.

It will be clear that while the number of related nucleotide sequences in the group may be as low as two, the method provides an increased advantage where the number of related nucleotide sequences is high. In a preferred form of the method the number of related nucleotide sequences in the group of related nucleotide sequences is more than 100, 200, 300, 400, 500, 600, 700, 800, 900 or 1000. The present invention is particularly applicable where the number of related nucleotide sequences is high and the density of SNPs is high.

In a preferred form of the method, the related nucleotide sequences are alleles of a gene. It is known that a human gene encoding the same protein may have different sequences (alleles) in different individuals. The proportion of the gene analyzed can be any proportion capable of providing allele-specific information. For example, polymorphic sites are often distributed non-randomly across the length of exons. Thus it may be necessary to direct probes only to certain discrete regions of a gene.

While most genes have only several alleles, some genes have a very high number. Examples of genes having high numbers of alleles are mainly those involved in the immune system, where hypervariability is a common feature. Exemplary genes include those of the major histocompatability complex (MHC), the T-cell receptor, the B-cell receptor, immunoglobulins, the killer inhibitory receptor (KIR), and the like. It will be understood however, that the methods described herein will be useful for any group of related nucleotide sequences, but that a greater advantage is gained where the related nucleotide sequences are hypervariable. A greater advantage still is provided where the hypervariability exits as high density SNPs.

As mentioned supra, MHC genes are extremely polymorphic. Class I and II MHC transmembrane proteins make up the Human Leukocyte Antigen (HLA) system that is used in tissue typing for the purposes of assessing transplant compatibility. Class I proteins are encoded by three loci: HLA-A, HLA-B and HLA-C that currently recognize 309, 563 and 167 alleles respectively.

Class II proteins have an alpha and beta chain, and are encoded by the loci DR, DQ and DP. The DR loci comprise 3 alleles for alpha and 483 for the beta chain. The DQ loci comprise 25 alleles for alpha and 56 for beta. The DP loci comprise 20 alleles for alpha and 107 for beta. It will therefore be noted that for the Class I region alone, there are many combinations of alleles that provide the HLA type of an individual.

Historically, HLA-based tissue typing was performed serologically using antibodies specific for those HLA antigens that have been identified in the human population. Most HLA typing is now performed by DNA methods, for high level allele assignment by sequencing, or sequence-equivalent methods. Such DNA typing, promises to improve the sensitivity and specificity of tissue typing. However, a problem with attempting to identify all HLA alleles by DNA-based methods (involving oligonucleotide sequences as probes) is that a very large number of probes is required to cover all possible alleles. The present invention alleviates this problem by providing probe sets that are manageable in number, while still capable of identifying all known alleles.

While the HLA-DR beta loci is currently recognized to comprise 483 alleles, it may appear that only 483 probes are necessary (one for each allele) until it is understood that each allele is a unique combination/pattern of SNPs distributed across all exonic nucleotides. The art has generally considered that the presence of even di-allelic SNPs is a significant problem in probe design given that current microarray SNP detection practice in which where a 25-mer oligonucleotide probe is used, the 12-mers flank the 13th position SNP allele. Therefore, where the flanking region(s) are non-monomorphic the art has hitherto thought it necessary to include probes that cover every SNP in every known combination within the 25-mer region even though not all exist in nature. It is accepted in the art that any polymorphic site requires 4 to the power of the number of alleles known to occur at that site. Thus, if the flanking 12-mers encompass two SNPs each, in both flanks, then the number of probes required to type the 13th position SNP is at least 4 to the power of 2=16.

Applicant's approach is divergent and is based on the recognition that not all sites that are polymorphic in any probe-length subsequence is present in all alleles of a HLA locus.

Without wishing to be limited by theory in any way, it is proposed that for HLA loci the theoretical possibilities are some 5-20 fold greater than the observed allelic sequences. An example of complex high SNP density loci are the HLA-DRB region loci (Expressed DRB1, DRB3, DRB4, DRB5; pseudogenes—not expressed DRB2, DRB6, DRB7, DRB8, DRB9). There are (some) 483 identified alleles among both categories of genes in this region. There are 270 nucleotides in the variable 2nd exon. Simple multiplication produces 130,410 different probes that would be required to resolve a genotype at this locus. There may be two main reasons for this observation: (i) combinations of SNPs exhibit linkage disequilibrium because they are inherited on chromosomal lengths that ensures non-randomness of SNP association; and (ii) populations have experienced 'bottleneck', resulting in the disappearance of some multi-SNP alleles, and the relative increase in frequency of others, influenced by population genetic factors such as natural selection, propensity for recombination, et cetera.

The present invention makes it possible to reduce the number of probes necessary for the identification of a genotype in a highly polymorphic system (such as HLA loci) such that all probes required to identify every allele may be immobilized on a single typical microarray chip.

It will be understood that the final number of probes required to definitively identify an allele will depend on the locus under consideration. However, in a preferred form of the method it is expected that more than a 50%, 60%, 70%, 80%, 90% or 95% reduction in probe number may be possible relative to the theoretical number of probes thought to be necessary.

While it is contemplated that maximum advantage in terms of minimising probe number will be gained where all redundant subsequences are removed, it is not essential to the invention that all are removed. Indeed, in some instances it is advantageous for some redundancy in subsequences to be maintained, in that an internal quality control mechanism results. Redundancy in the probe set can result from the fact that redundancy occurs across loci. Redundant probes relating to redundancy across loci may therefore be maintained in a probe set provided by the present invention for the purposes of quality control. As an example, where a probe list is generated for the assignment of allele types at HLA Class I and Class II loci and of genes and allele types at the KIR loci, about 34,500 probes are identified. The list identifies variations involving hypervariable exons 2 and 3 at HLA Class I loci (A, B, C) and exon 2 at Class II loci (DRB, DQB, DPB), and all known variations at up to 10 exons at KIR loci. In the list of probes, there are 2167 duplicated sequences due to direct repeats of sequences present when comparing HLA-A, -B, and -C, or DPB, DQB, and DRB, e.g.

| Probe Tag | Probe Sequence |
| --- | --- |
| 5522A_E3_232_2_25 | TCCGCAGATACCTGGAGAACAGGAA (SEQ ID NO: 2) |
| 15458C_E3_232_4_25 | TCCGCAGATACCTGGAGAACAGGAA (SEQ ID NO: 3) |
| 9492B_E3_13_17_25 | TCCAGAGGATGTTTGGCTGCGACCT (SEQ ID NO: 4) |
| 13765C_E3_13_10_25 | TCCAGAGGATGTTTGGCTGCGACCT (SEQ ID NO: 5) |
| 22138R_E2_155_21_25 | TGTCGCCGAGTACTGGAACAGCCAG (SEQ ID NO: 6) |
| 17957Q_E2_155_9_25 | TGTCGCCGAGTACTGGAACAGCCAG (SEQ ID NO: 7) |
| 21088R_E2_105_3_25 | TTCGACAGCGACGTGGGGGAGTTCC (SEQ ID NO: 8) |
| 17442Q_E2_105_3_25 | TTCGACAGCGACGTGGGGGAGTTCC (SEQ ID NO: 9) |
| 16011P_E2_99_1_25 | TTCGACAGCGACGTGGGGGAGTTCC (SEQ ID NO: 10) |

Where probes are labelled in the following manner
a=consecutive probe number
F=either A, B, C, P, Q, R, K
E=exon
c=exon number
d=first base of 25-mer in exon
e=1-30, 1 is the reference (consensus), unique allele types follow consecutively
f=probe length.

The replicate probe sequences are retained in one form of the invention to contribute to both technical and genetic components of quality assurance. Specifically, where there is a bona fide hybridisation with one probe consistent with reactivity to all other probes identifying an allele at the first locus, but in which the same probe sequence is not an integral component of either allele at a second locus, then there will be reactivity in the replicate distinct from those reflecting the alleles at the second locus.

As an example of the operation of this internal quality control mechanism, the lowest level of resolution is the allele lineage, or family. Considering DRB there are 13 lineages (*01, *03, *04, *07, *08, *09, *10, *11, *12, *13, *14, *15, *16). By including probes for all four DRB expressed loci, the presence or absence of DRB3, DRB4 and DRB5 provides information on the lineage type of DRB1 alleles, independent of DRB1 probe reactivity.

In the context of the present invention, the term "redundant" is intended to mean that if the sequence is removed from the first set of subsequences there is no appreciable difference in the ability to identify a member of the group of related nucleotide sequences. Redundancy may be considered as complete (i.e. two subsequences are identical in nucleotide sequence) or incomplete (e.g. the two subsequences are physically non-identical, but are functionally identical). Thus, depending on the hybridisation conditions used, two different probes may bind to a single nucleotide sequence and are therefore functionally identical. This would be expected where hybridisation conditions are of a relatively low stringency.

The non-redundant or reduced redundancy sequences are generated based on the alleles previously identified using DNA sequencing. If a new allele is identified that contains a new polymorphism, then additional target sequences may need to be included in the probe set to ensure detection of that new polymorphism. If the new polymorphism occurs in a target sequence that was previously found to be redundant, then in light of the knowledge of the new polymorphism, that target sequence becomes necessary as a probe target and therefore non-redundant.

In one form of the method, the method is amenable to automation. Methods of the prior art such as Guo et al (2002) design probes based on the careful consideration of all related nucleotide sequences in an effort to identify probes that cover all observed combinations of SNPs. This is of course very labour intensive, and the success or failure dependant on the expertise of the individual performing the analysis. The task of designing probes may become practically infeasible if the number of related sequences is very large, or the number of alleles is very large. By contrast, the present methods are particularly amenable for implementation on a computer in the form of software-based probe set design.

The method may include a combination of different subsequence lengths and different levels of overlap between the subsequences. In a highly preferred form of the invention the subsequence is about 25 nucleotides in length, and the degree of overlap is maximal.

The related sequences may include sequences from all known alleles of a gene. Alternatively, the related sequences may include known and hitherto unknown sequences. For example, it may be known that a polymorphism is found at a given position in a gene, and that the position can have one of two alternative forms (e.g. A or T). It will be possible to include "hypothetical" sequences where a G or C is present in that position. Alternatively, where a given position is not known to have any polymorphisms but is suspected to, probes directed to the three alternative forms may be included in the probe set. Furthermore, the invention will allow the detection of new combinations of SNPs that result in a new allele. These approaches are very probe-demanding, and use of the present invention makes it practically feasible given the vast reduction in probe numbers required. The chance for finding new alleles will be greater where maximum overlap between the subsequences is used.

It will be appreciated that the presence of a hitherto unrecognised allele may also be discovered by the internal quality control mechanisms as discussed supra. Probe reactivity discordance with known alleles will signal the presence of either an error in assay, or the presence of a new allele.

As discussed supra, the allele analysed may be directed to protein-coding regions exclusively, or noncoding regions exclusively. Alternatively, a combination of noncoding and protein-coding regions may be used.

In another aspect the present invention provides a set of probes capable of specifically hybridizing to target nucleotide sequences identified by the methods described herein. In one form of the invention, the probe set has a lower level of redundancy than a probe set designed by methods known in the art.

Given the target subsequences, the skilled person will be capable of synthesizing probes capable of hybridising with each target subsequence. The probes are substantially complimentary to the non-redundant sequences identified. The probes may be sense or antisense if the target is generated from a double stranded template. The probes can be made by any method known to the skilled artisan, although the final use of the probes will likely dictate the most appropriate method. For example where the probes are for use in a microarray environment, they may be synthesized in situ on the glass or nylon wafer forming the array solid support matrix. For other applications, the probes may be synthesized on an automated apparatus such as the Beckman 1000M DNA synthesizer and subsequently used for methods such as PCR to detect an allele. Alternatively, the probe may be coupled to a solid support after manufacture.

It is well within the ability of the skilled person to investigate whether any advantage is gained by the use of modified nucleotides in probes designed by the instant methods, such as locked nucleic acids.

For the purposes of quality assurance, the probe set optionally includes a paired "mismatch" probe for each probe on the array that perfectly matches its target sequence. The mismatch probe contains a single mismatch located directly in the middle of the 25-base probe sequence. While the perfect match probe provides measurable fluorescence when sample binds to it, the paired mismatch probe is used to detect and eliminate any false or contaminating fluorescence within that measurement. The mismatch probe serves as an internal control for its perfect match partner because it hybridizes to non-specific sequences about as effectively as its counterpart, allowing spurious signals, from cross hybridization for example, to be efficiently quantified and subtracted from a gene expression measurement or genotype call.

The probe may include a label to facilitate detection. Exemplary labels include Cy5, Cy3, FITC, rhodamine, biotin, DIG and various radioisotopes.

A probe sequence list generated according to the present invention can be expanded to include additional allelic variation at other exons within the mRNA transcript, at sequences intervening or flanking the exons, including introns, 5' and 3' untranslated regions, and intergenic regions.

In another aspect the present invention provides a method of identifying a member of a group of related nucleotide sequences using a set of probes as described herein. One way of achieving this is using microarray technology. Thus, another aspect the invention provides a set of probes as described herein immobilized on a solid matrix. An exemplary embodiment of this form of the invention is found in the GeneChip® technology marketed by Affymetrix®. This technology relies on a photolithographic process by coating a 5"×5" quartz wafer with a light-sensitive chemical compound that prevents coupling between the wafer and the first nucleotide of the DNA probe being created. Lithographic masks are used to either block or transmit light onto specific locations of the wafer surface. The surface is then flooded with a solution containing either adenine, thymine, cytosine, or guanine, and coupling occurs only in those regions on the glass that have been deprotected through illumination. The coupled nucleotide also bears a light-sensitive protecting group, so the cycle can be repeated. Other methods of immobilizing probes are provided by a number of companies including Oxford Gene Technology (Oxford, U.K.), Agilent Technologies (Palo Alto, Calif., U.S.A.) and Nimblegen Systems Inc (Madison, Wis., U.S.A).

The probes of the present invention are useful not only for identifying a member of a group of related nucleotide sequences, but also for the recovery of the member so identified. Accordingly, one form of the method further comprises the step of recovering a member of a group of related nucleotide sequences using a probe set as described herein. In the context of the present invention, the term "recover" includes the physical separation of the member identified by (or bound to) a probe forming part of a probe set of the present invention from at least one other member of a group of related nucleotide sequences. Advantageously, the recovered member can be analysed to provide genotypic and/or phenotypic information on the subject from which the member is derived.

The method may comprise the steps of exposing the probe to the group of related nucleotide sequences under conditions allowing a probe of the probe set to bind to a nucleotide sequence of the group of related nucleotide sequences to form a probe/nucleotide sequence complex, and substantially isolating the probe/nucleotide sequence complex.

The skilled person is familiar with identifying conditions allowing binding of a nucleic acid probe to a target nucleotide sequence. It is also within the capabilities of the skilled person to identify conditions conducive to the specific binding of a nucleic acid probe to a target nucleotide sequence. Physical parameters of the reaction solution such as temperature, ionic strength and pH may be manipulated such that binding takes place on a specific or non-specific basis.

The skilled person is also aware of many methods for the substantial isolation of a probe/nucleotide sequence complex. Recovery of molecules using reagents that are chemically reciprocal to the target, such as nucleotide sequence by antisense sequence, or vice versa; are well known across many chemistries. Typically, a probe is attached to a solid phase such as a chromatographic matrix, a bead (for example, a magnetic bead), or a planar glass surfaces (such as those used microarray formats, for example SuperEpoxy, SuperAmine, SuperAldehyde and SuperNitro manufactured by Telechem International Inc). The attached probe is then exposed to a solution containing a mixture of nucleic acid sequence fragments, and binding of the probe to nucleic sequence allowed to occur. The probe/nucleic acid sequence complex is then separated from unbound molecules by a suitable method. For example, where the probe is bound to a magnetic bead, the magnetic beads (with at least some having bound nucleic acid sequence fragment) are separated by the application of a magnetic field to the reaction solution.

It will be understood that in some situations the probe/nucleotide sequence complex can be recovered without attachment of either reactant to a solid phase. For instance, probe/nucleotide sequence complexes may be separated in the fluid phase of electrophoresis. A DNA fragment bound to a probe will migrate at a different rate to a fragment of the same, or similar, electrophoretic mobility.

Once the probe/nucleotide sequence complex is substantially isolated, the nucleotide sequence may be eluted from the probe. Typically, it is the elution step that is manipulated to increase or decrease the specificity of the probe/nucleotide sequence binding reaction. Elution may be achieved by altering any one of more of the following parameters: temperature, ionic strength and pH. Elution may also be controlled with the use of detergents or other additives.

The recovered nucleotide sequence may be analyzed by any appropriate method to obtain any required information. The analysis may include any one or more of the following characteristics: nucleotide sequence, AT content, CG content, length, secondary structure, ability to bind to a protein, ability to bind to another nucleic acid sequence, ability to be cleaved by an endonuclease, methylation status, and the like. Typically, however, the analysis will be nucleotide sequence analysis.

The recovered nucleic acid sequences may be any length, but in some forms of the invention at least 10, 20, 30, 40, 50, 60, 70, 80 or 90 bases long. In other forms of the invention the recovered nucleic acid sequence is at least 100, 200, 300, 400, or 500 bases long.

The recovered nucleic acid sequence may be used for any reason, however it is typically used for providing genotypic and/or phenotypic information on a subject. The probe sets provided by the present invention are, in some embodiments, capable of binding to every known allele of a given gene. For example, if it is desired to read the nucleotide sequence of a certain fragment of genomic DNA, and that fragment of genomic DNA included a number of sites at which mutations were possible, then that fragment may be recovered from any subject irrespective of the presence or absence of any mutation(s). As discussed supra a particular advantage is gained for the recovery of fragments having a high density of SNPs, such as fragments of HLA-MHC genes, or KIR genes.

In one embodiment, the method is used for the isolation of exomic nucleic acid sequences from a subject. As is now understood, the proportion of genomic DNA that actually codes for protein is small, and the present invention may be used to extract just that exomic proportion from the whole of a subject's genomic DNA for subsequent analysis. This approach requires significantly less sequence analysis than would be otherwise required where the whole genome is sequenced.

In another aspect the present invention provides a computer executable program (software) capable of executing the methods described herein. While the present invention may be implemented manually, it is preferably performed on a personal computer under the instruction of appropriate software. Given the disclosure herein, the skilled person will be enabled to write appropriate code to execute the method. Example pseudo-code for the 0101 allele DRB1 locus follows:

```
[AWAIT USER INPUT]
(IF) Mouse_Click Event detected on the Grid interface;
    [DETERMINE] grid row and grid column of the Click;
/* Since all sequences are displayed in tabular format, they are also
stored in tabular format as a memory object according to the
following:
ReferenceNameArray[position     0]    =    "DRB10101";
ReferenceBasisArray[position 0]= "TGTCCCCA....";
which in memory forms a tabular structure like this:
        ReferenceNameArray      ReferenceBasisArray
Index 0: "DRB01*010101"             " TGTCCCCA...."
Index 1: "DRB01*010102"             " TGTCCCCC...."
Index 2: "DRB01*010103"             " TGTCCCCC...."
*/
[DETERMINE] ReferenceBasisArray base range (25 mers) using grid column
click value as index.
[DETERMINE] ReferenceNameArray using grid row click as index
/**
how to determine the range of 25?
If the ReferenceBasisArray (ie: array of all bases) contains 150
bases, then use the grid column click value to determine the middle
point.
ie;
                    1  2  3  4  5  6  7  8  9  10 11 12 13 14 15 16 20 21..n
DRB01*010101:       G  T  G  T  C  C  C  C  A  C  A  G  ...
hence if the user clicks on column 12, then our range becomes,
min = middle_point – 12, max = middle_point + 12;
**/
[EXTRACT] 25 bases from each ReferenceBasisArray Record
(IF) base is different to Reference Record
    [HIDE/DISCARD] row
else
    [DISPLAY ROW]
```

The software may have the facility to investigate the effects of a range of parameters on the number of probes required to resolve a specific allele. In this way, it may be possible to further decrease the number of probes required. For example, the software may allow the user to define the length of the probe-length subsequence, the degree of overlap of the subsequences, the rules for defining whether two subsequences are redundant and the like. Indeed, the software may include algorithms to automatically trial a range for each parameter to give the lowest number of probe-length subsequences (and therefore the number of probes in the probe set). A probe may also be removed from the probe set if it is considered likely to have significant secondary structure, or too high or too low a melting temperature such that it will not reliably hybridise to the relevant target. A probe may be removed from the probe set on the basis of empirical probe optimisation experiments demonstrating a lack of suitability.

It will be appreciated that the present invention will have application in a wide range of technical fields. It is anticipated that the field of medicine will gain particular advantage, where the method may be used for genotyping individuals. The methods will be particularly useful in transplantation tissue typing (e.g. using the HLA genes, KIR genes, minor Histocompatability loci, and the like), as well as pharmacogenomics, DNA "fingerprinting" and the like. The probes may be used for any application comprising in situ hybridisation, slot blot, dot blot, colony hybridization, plaque hybridization, Northern blotting, Southern blotting, as well as microarray applications, It is anticipated that the invention will be useful in any application where it is necessary or desirable to reduce the number of unique probes required for analysis of a nucleotide sequence, and not only in the area of microarray analysis. The invention will be applicable even where the numbers of probes required to undertake a task in identifying a particular nucleotide sequence amongst a number of others are not so great as to extend beyond the capacity of a chip. Minimisation of probe numbers will allow tests for other loci to be included on the one chip such that an increase number of loci can be tested for on the one chip. It is of course less costly to run one chip as compared with 20.

It is anticipated that applications will extend to use in non-human animals such as primates, for example in the pre-clinical pharmacogenomic assessments of candidate pharmaceuticals. The invention is also contemplated to be useful for testing of animals having economic importance (such as cattle, poultry and the like), for example in breeding programs to improve parameters such as lean muscle content.

The present invention will now be further described by reference to the following non-limiting example. The skilled person will understand that the HLA loci are some of the most variable loci found in nature. It will be appreciated that a method able to be operable for an HLA locus, then any other locus will be operable.

EXAMPLE 1

Identification of Oligonucleotide Probe Set for Definitive Genotyping of the HLA-DRB Locus Outline of Protocol The DRB locus of HLA was analyzed by the present methods to identify a probe set capable of identifying any known allele of the locus. The DRB locus has the following known alleles:
DRB1*010101, DRB1*010102, DRB1*010103, DRB1*010201, DRB1*010202, DRB1*010203, DRB1*010204, DRB1*0103, DRB1*0104, DRB1*0105, DRB1*0106, DRB1*0107, DRB1*0108, DRB1*0109, DRB1*0110, DRB1*0111, DRB1*0112, DRB1*0113, DRB1*030101, DRB1*030102, DRB1*030201, DRB1*030202, DRB1*0303, DRB1*0304, DRB1*030501, DRB1*030502, DRB1*0306, DRB1*0307, DRB1*0308, DRB1*0309, DRB1*0310, DRB1*0311, DRB1*0312, DRB1*0313, DRB1*0314, DRB1*0315, DRB1*0316, DRB1*0317, DRB1*0318, DRB1*0319, DRB1*0320, DRB1*0321, DRB1*0322, DRB1*0323, DRB1*0324, DRB1*0325, DRB1*0326, DRB1*0327, DRB1*0328, DRB1*040101, DRB1*040102, DRB1*0402, DRB1*040301, DRB1*040302, DRB1*0404, DRB1*040501, DRB1*040502, DRB1*040503, DRB1*040504, DRB1*0406, DRB1*040701, DRB1*040702, DRB1*040703, DRB1*0408, DRB1*0409, DRB1*0410, DRB1*0411, DRB1*0412, DRB1*0413, DRB1*0414, DRB1*0415, DRB1*0416, DRB1*0417, DRB1*0418, DRB1*0419, DRB1*0420, DRB1*0421, DRB1*0422, DRB1*0423, DRB1*0424, DRB1*0425, DRB1*0426, DRB1*0427, DRB1*0428, DRB1*0429, DRB1*0430, DRB1*0431, DRB1*0432, DRB1*0433, DRB1*0434, DRB1*0435, DRB1*0436, DRB1*0437, DRB1*0438, DRB1*0439, DRB1*0440, DRB1*0441, DRB1*0442, DRB1*0443, DRB1*0444, DRB1*0445, DRB1*0446, DRB1*0447, DRB1*0448, DRB1*0449, DRB1*0450, DRB1*0451, DRB1*0452, DRB1*070101, DRB1*070102, DRB1*0703, DRB1*0704, DRB1*0705, DRB1*0706, DRB1*0707, DRB1*0708, DRB1*0709, DRB1*080101, DRB1*080102, DRB1*080201, DRB1*080202, DRB1*080203, DRB1*080302, DRB1*080401, DRB1*080402, DRB1*080403, DRB1*080404, DRB1*0805, DRB1*0806, DRB1*0807, DRB1*0808, DRB1*0809, DRB1*0810, DRB1*0811, DRB1*0812, DRB1*0813, DRB1*0814, DRB1*0815, DRB1*0816, DRB1*0817, DRB1*0818, DRB1*0819, DRB1*0820, DRB1*0821, DRB1*0822, DRB1*0823, DRB1*0824, DRB1*0825, DRB1*0826, DRB1*0827, DRB1*0828, DRB1*0829, DRB1*090102, DRB1*0902, DRB1*0903, DRB1*0904, DRB1*100101, DRB1*100102, DRB1*110101, DRB1*110102, DRB1*110103, DRB1*110104, DRB1*110105, DRB1*1102, DRB1*1103, DRB1*110401, DRB1*110402, DRB1*1105, DRB1*110601, DRB1*110602, DRB1*1107, DRB1*110801, DRB1*110802, DRB1*1109, DRB1*1110, DRB1*1111, DRB1*111201, DRB1*111202, DRB1*1113, DRB1*1114, DRB1*1115, DRB1*1116, DRB1*1117, DRB1*1118, DRB1*111901, DRB1*111902, DRB1*1120, DRB1*1121, DRB11122, DRB1*1123, DRB1*1124, DRB1*1125, DRB1*1126, DRB1*112701, DRB1*112702, DRB1*1128, DRB1*1129, DRB1*1130, DRB1*1131, DRB1*1132, DRB1*1133, DRB1*1134, DRB1*1135, DRB1*1136, DRB1*1137, DRB1*1138, DRB1*1139, DRB1*1140, DRB1*1141, DRB1*1142, DRB1*1143, DRB1*1144, DRB1*1145, DRB1*1146, DRB1*1147, DRB1*1148, DRB1*1149, DRB1*1150, DRB1*1151, DRB1*1152, DRB1*1153, DRB1*1154, DRB1*120101, DRB1*120102, DRB1*120201, DRB1*120202, DRB1*120302, DRB1*1204, DRB1*1205, DRB1*1206, DRB1*1207, DRB1*1208, DRB1*1209, DRB1*1210, DRB1*1211, DRB1*130101, DRB1*130102, DRB1*130103, DRB1*130201, DRB1*130202, DRB1*130301, DRB1*130302 DRB1*1304, DRB1*1305, DRB1*1306, DRB1*130701, DRB1*130702, DRB1*1308, DRB1*1309, DRB1*1310, DRB1*1311, DRB1*1312, DRB1*1313, DRB1*131401, DRB1*131402, DRB1*1315, DRB1*1316, DRB1*1317, DRB1*1318, DRB1*1319, DRB1*1320, DRB1*1321, DRB1*1322, DRB1*1323, DRB1*1324, DRB1*1325, DRB1*1326, DRB1*1327, DRB1*1328, DRB1*1329, DRB1*1330, DRB11331, DRB1*1332, DRB1*1333, DRB1*1334, DRB1*1335, DRB1*1336, DRB1*1337, DRB1*1338, DRB1*1339, DRB1*1340, DRB1*1341, DRB1*1342, DRB1*1343, DRB1*1344, DRB1*1345, DRB1*1346, DRB1*1347, DRB1*1348, DRB1*1349, DRB1*1350, DRB1*1351, DRB1*1352, DRB1*1353, DRB1*1354, DRB1*1355, DRB1*1356, DRB1*1357, DRB1*1358, DRB1*1359, DRB1*1360, DRB1*1361, DRB1*1362, DRB1*1363, DRB1*1364, DRB1*1365, DRB1*1366, DRB1*140101, DRB1*140102, DRB1*1402, DRB1*140301, DRB1*140302, DRB1*1404, DRB1*140501, DRB1*140502, DRB1*1406, DRB1*140701, DRB1*140702, DRB1*1408, DRB1*1409, DRB1*1410, DRB1*1411, DRB1*1412, DRB1*1413, DRB1*1414, DRB1*1415, DRB1*1416, DRB1*1417, DRB1*1418, DRB1*1419, DRB1*1420, DRB1*1421, DRB1*1422, DRB1*142301, DRB1*142302, DRB1*1424, DRB1*1425, DRB1*1426, DRB1*1427, DRB1*1428, DRB1*1429, DRB1*1430, DRB1*1431, DRB1*1432, DRB1*1433, DRB1*1434, DRB1*1435, DRB1*1436, DRB1*1437, DRB1*1438, DRB1*1439, DRB1*1440, DRB1*1441, DRB1*1442, DRB1*1443, DRB1*1444, DRB1*1445, DRB1*1446, DRB1*1447, DRB1*1448, DRB1*150101, DRB1*150102, DRB1*150103, DRB1*150104, DRB1*150105, DRB1*150201, DRB1*150202, DRB1*150203, DRB1*1503, DRB1*1504, DRB1*1505, DRB1*1506, DRB1*1507, DRB1*1508, DRB1*1509, DRB1*1510, DRB1*1511, DRB1*1512, DRB1*1513, DRB1*1514, DRB1*1515, DRB1*160101, DRB1*160102, DRB1*160201, DRB1*160202, DRB1*1603, DRB1*1604, DRB1*160501, DRB1*160502, DRB1*1607, DRB1*1608, DRB2*0101, DRB3*010101, DRB3*01010201, DRB3*01010202, DRB3*010103, DRB3*010104, DRB3*0102, DRB3*0103, DRB3*0104, DRB3*0105, DRB3*0106, DRB3*0107, DRB3*0108, DRB3*0109, DRB3*0110, DRB3*0111, DRB3*0201, DRB3*020201, DRB3*020202, DRB3*020203, DRB3*020204, DRB3*0203, DRB3*0204, DRB3*0205, DRB3*0206, DRB3*0207, DRB3*0208, DRB3*0209, DRB3*0210, DRB3*0211, DRB3*0212, DRB3*0213, DRB3*0214, DRB3*0215, DRB3*0216, DRB3*0217, DRB3*0218, DRB3*0219, DRB3*030101, DRB3*030102, DRB3*0302, DRB3*0303, DRB4*01010101, DRB4*0102, DRB4*01030101, DRB4*01030102N, DRB4*010302, DRB4*010303, DRB4*010304, DRB4*0104, DRB4*0105, DRB4*0106, DRB4*0107, DRB4*0201 N, DRB4*0301 N, DRB5*010101, DRB5*010102, DRB5*0102, DRB5*0103, DRB5*0104, DRB5*0105, DRB5*0106, DRB5*0107, DRB5*0108N, DRB5*0109, DRB5*0110N, DRB5*0111, DRB5*0112, DRB5*0113, DRB5*0202, DRB5*0203, DRB5*0204, DRB5*0205, DRB6*0101, DRB6*0201, DRB6*0202, DRB7*010101, DRB7*010102, DRB8*0101, and DRB9*0101.

A subsequence length of 25 nucleotides was selected, and maximal sequential overlap was used to provide the series of subsequences. The second exon was chosen as the starting point for the analysis, with the first 25-mer subsequence positioned such that the 13$^{th}$ nucleotide of the subsequence (underlined, see below) aligned with the first base of the second exon. This is shown below using a reference sequence typical of many DRB alleles as follows:

```
intron 1____exon 2_____ . . .
GTGTCCCCACAGCACGTTTCTTGTG . . .   (SEQ ID NO: 11)
```

Step 1: Defining Subsequences for Selecting Probes Centered on the First Nucleotide of the Second Exon.

The first subject subsequence is the 25 nucleotide subsequence of the DRB locus about the interface of intron 1 and exon 2. This first subsequence is generated against the first nucleotide in exon 1 (the underlined "C" residue): GTGTCCCACAGCACGTTTCTTGTG (SEQ ID NO:12) (this sequence is a reference sequence found in 26 alleles).

Step 2: Defining Subsequences for Selecting Probes Centered on the Second Nucleotide of the Second Exon.

The protocol of step 1 is repeated, except that 25-mer subsequence is centered on the second nucleotide. Again, considering a reference sequence the 25-mer is: TGTCCCCACAGCACGTTTCTTGTGG (SEQ ID NO:13).

Steps 3 to 284. Defining Subsequences for Selecting Probes Centered on the 3$^{rd}$ to 284$^{th}$ Nucleotide of the Second Exon.

The protocol of step 1 is repeated for each nucleotide in the exon.

Step 285: Pooling of 25-Mer Subsequences

All 25-mer subsequences for each allele of the locus are combined to form a set of target nucleotide sequences capable of identifying all alleles of the locus.

Step 286: Removal of Redundant Subsequences

All subsequences are analyzed, and redundant sequences (exact matches) are removed to leave only unique subsequences. It is estimated that if the process was carried out for all 270 nucleotides of the second exon, only about 5,500 unique subsequences would be generated. This is a significant reduction in probe number predicted in the prior art.

EXAMPLE 2

Production of Microarray Chip

The 5,500 target nucleotide sequences in the pool are synthesized directly onto a microarray chip by Affymetrix Inc who provide a custom gene chip array service.

EXAMPLE 3

Use of Probes to Assign Identify Drb Allele for an Individual

Patient Sample.

DNA extraction of peripheral blood or buccal smear is standard practice. Approx. 1,000 ng of DNA is recommended for microarray assay.

Long PCR.

Primers can be located in introns, exons or a combination. For instance, for HLA-DRB typing, primers are selected upstream in intron 1, and downstream in exon 6. The amplicon is approx. 5.1 kb. The disadvantage of using intron sequences as primer sites is that there is usually less sequence data, and absence of data corresponding to exon alleles, than for corresponding exon sequence. For HLA-DRB, published data provides sufficient intron 1 data for primer selection. However, even in this case, further sequencing is near certain to reveal new SNPs. If they occur in the primer sequence, it can be expected to complicate amplification of sequences bearing that new variant. The alternative is to utilise exon sequences since these have been more extensively studied. For HLA-DRB there are sites suitable as primers further upstream, in exon 1, Since amplicons using exon 1 and exon 6 primers span the full length of the 8 kb intron 1, the resulting amplicon is over 13 kb in length. Applicants have confirmed the suitability of the commercial Long PCR kit for amplification of 17 kb, so the exon only primered amplicon is also suitable.

Fragmentation of Amplicons.

The protocol process is non-specific, resulting in the shearing of the amplicons into fragments of tens to low hundreds of nucleotides required for efficient hybridisation to the chip-adherent probes. Details provided in the following document GeneChip® CustomSeg™ Resequencing (Array Protocol) Version 2.0, 701231 Rev. 3; the entire contents of which is incorporated by reference. This document can be obtained from Affymetrix Inc (Technical Support) 3380 Central Expressway Santa Clara, Calif. 95051 U.S.A.

Hybridisation.

Details are provided in GeneChip® CustomSeg™ Resequencing (Array Protocol) Version 2.0, 701231 Rev. 3

Allele Assignment.

Allele assignment is achieved by relating the probe hybridisation patterns to allele sequence variation by an iterative reduction algorithm (Helmberg W, Lanzer G, Zahn R, Weinmayr B, Wagner T, Albert E. Virtual DNA analysis—a new tool for combination and standardised evaluation of SSO, SSP and sequencing-based typing results. Tissue Antigens. 1998 June; 51(6):587-92.)

EXAMPLE 4

Generation of Probe Set for Assignment of Allele Types at HLA-A*0201 (Exons 2 and 3)

The following exon sequences of HLA*0201 were used to generate a probe set for assignment of HLA-A*0201. For the purposes of probe generation, the exon sequences were extended by 12 nucleotides in both 5' and 3' directions into the adjacent intronic regions.

Exon2:
(SEQ ID NO: 14)
GCTCCCACTCCATGAGGTATTTCTTCACATCCGTGTCCCGGCCCGGC

CGCGGGGAGCCCCGCTTCATCGCCGTGGGCTACGTGGACGACACGCA

GTTCGTGCGGTTCGACAGCGACGCCGCGAGCCAGAGGATGGAGCCGC

GGGCGCCGTGGATAGAGCAGGAGGGTCCGGAGTATTGGGACGGGGAG

ACACGGAAAGTGAAGGCCCACTCACAGACTCACCGAGTGGACCTGGG

GACCCTGCGCGGCTACTACAACCAGAGCGAGGCCG

Exon 3
(SEQ ID NO: 15)
GTTCTCACACCGTCCAGAGGATGTATGGCTGCGACGTGGGGTCGGAC

TGGCGCTTCCTCCGCGGGTACCACCAGTACGCCTACGACGGCAAGGA

TTACATCGCCCTGAAAGAGGACCTGCGCTCTTGGACCGCGGCGGACA

TGGCAGCTCAGACCACCAAGCACAAGTGGGAGGCGGCCCATGTGGCG

GAGCAGTTGAGAGCCTACCTGGAGGGCACGTGCGTGGAGTGGCTCCG

CAGATACCTGGAGAACGGGAAGGAGACGCTGCAGCGCACGG

A subsequence length of 25 was chosen, and maximum overlap utilized.

Probe sets that are capable of identifying the above hypervariable Exon 2/3 regions are shown in FIG. 2. Where it is desired to identify hypervariable regions other than that shown above, the probe generation process is repeated for each hypervariable region. The redundant probe sequences may then be removed.

Finally, it is to be understood that various other modifications and/or alterations may be made without departing from the spirit of the present invention as outlined herein.

The invention claimed is:

1. A method for identifying a set of target nucleotide sequences capable of identifying a member of a group of related-nucleotide sequences related by sequence identity and having at least 50% sequence identity, the method comprising the step of dividing the nucleotide sequence of each member of the group into a plurality of subsequences, wherein at least two of the subsequences overlap and each of the subsequences is from about 10 to about 50 nucleotides in length;
   analyzing at least a portion of the subsequences for redundancy; and
   removing or not including at least one redundant sequence from the set of target nucleotide sequences.

2. The method according to claim 1 wherein at least three of the subsequences overlap with each other.

3. The method according to claim 1 wherein the overlap is complete overlap.

4. The method according to claim 1 wherein one or more of the subsequences does not contain one or more polymorphic sites at, or toward, the 5' and/or 3' ends of the one or more subsequences.

5. The method according to claim 1 wherein one or more of the subsequences contains one or more polymorphic sites at, or toward, the center of the one or more subsequences.

6. The method according to claim 1 wherein one or more of the subsequences contain one polymorphic site at the center of the one or more subsequences.

7. The method according to claim 1 wherein the subsequences are from about 15 to about 35 nucleotides in length.

8. The method according to claim 1 wherein the subsequences are about 25 nucleotides in length.

9. The method according to claim 1 wherein all subsequences are of the same or similar length.

10. The method according to claim 1 wherein the related nucleotide sequences have a sequence identity of at least 80%.

11. The method according to claim 1 wherein the related sequences exhibit SNPs at a density of at least two SNP sites within the span of at least one subsequence.

12. The method according to claim 1 wherein the related sequences are protein coding or non-coding.

13. The method according to claim 1 wherein the related sequences are directed to the same region of a genome.

14. The method according to claim 1 wherein the related nucleotide sequences are alleles of a gene.

15. The method according to claim 1 wherein the number of related nucleotide sequences in the group of related nucleotide sequences is more than 100.

16. The method according to claim 1 wherein the related nucleotide sequences are part of a gene locus involved in the immune system.

17. The method according to claim 16 wherein the locus is a locus of the Major Histocompatability Complex (MHC), the T-cell receptor, the B-cell receptor, the Killer Inhibitory Receptor, or an immunoglobulin.

18. The method according to claim 16 wherein the locus is a locus of the Human Leukocyte Antigen (HLA) system.

19. The method according to claim 16 wherein the wherein the locus is a Class I or Class II MHC transmembrane protein.

20. The method according to claim 16 wherein the locus is a DR, DQ or DP locus.

21. The method according to claim 1 wherein the method reduces the number of sequences in the set of target nucleotide sequences to at least one-fifth the number of target nucleotide sequences expected by multiplying the number of nucleotides in the locus analyzed by the number of known alleles of the locus.

22. The method according to claim 1 wherein the method reduces the number of target nucleotide sequences to at least $\frac{1}{20}$ the number of target nucleotide sequences expected by multiplying the number of nucleotides in the locus analyzed by the number of known alleles of the locus.

23. The method according to claim 1 wherein the set of target nucleotide sequences includes only one occurrence of any subsequence.

24. The method according to claim 1, that is automated.

25. The method according to claim 1 wherein the number of related nucleotide sequences in the group of related nucleotide sequences is more than 500.

26. The method according to claim 1 that further comprises synthesizing the set of target nucleotide sequences.

27. The method according to claim 1 that further comprises immobilizing the set of target nucleotide sequences on a substrate.

28. The method according to claim 1 wherein the related sequences are a combination of protein coding and non-coding sequences.

* * * * *